(12) United States Patent
Kelliher et al.

(10) Patent No.: US 9,516,824 B2
(45) Date of Patent: Dec. 13, 2016

(54) METHOD FOR MODULATING THE NUMBER OF ARCHESPORIAL CELLS IN A DEVELOPING ANTHER

(71) Applicant: The Board of Trustees of the Leland Stanford Junior University, Palo Alto, CA (US)

(72) Inventors: Timothy Kelliher, Durham, NC (US); Virginia Walbot, Palo Alto, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 21 days.

(21) Appl. No.: 14/373,319

(22) PCT Filed: Feb. 13, 2013

(86) PCT No.: PCT/US2013/025940
§ 371 (c)(1),
(2) Date: Jul. 18, 2014

(87) PCT Pub. No.: WO2013/123051
PCT Pub. Date: Aug. 22, 2013

(65) Prior Publication Data
US 2014/0359897 A1    Dec. 4, 2014

Related U.S. Application Data

(60) Provisional application No. 61/598,544, filed on Feb. 14, 2012.

(51) Int. Cl.
*A01H 3/04* (2006.01)

(52) U.S. Cl.
CPC ...................................... *A01H 3/04* (2013.01)

(58) Field of Classification Search
None
See application file for complete search history.

(56) References Cited

U.S. PATENT DOCUMENTS

| | | |
|---|---|---|
| 6,297,194 B1 | 10/2001 | Miller et al. |
| 6,407,311 B1 * | 6/2002 | Feldman .................. A01H 1/04 800/260 |
| 7,109,149 B2 | 9/2006 | Palanivelu et al. |
| 7,132,590 B2 | 11/2006 | Feyereisen et al. |
| 2008/0233058 A1 | 9/2008 | Maitra et al. |
| 2009/0038028 A1 | 2/2009 | Albertsen et al. |
| 2010/0098645 A1 | 4/2010 | Barrett et al. |
| 2011/0117071 A1 | 5/2011 | Barrett et al. |

OTHER PUBLICATIONS

Jiang et al, Plant Cell Rep (2007) 26:1627-1634.*
Acquaah, Principles of Plant Genetics and Breeding (2007) pp. 334-349, Blackwell Publishing, 350 Main Street, Malden, MA 02148-5020, USA.*
Ambrus et al, Protoplasma (2006) 228: 87-94.*
Sheoran et al, Journal of Proteomics (2009) 71: 624-636.*
Canales; et al., "EXS, a putative LRR receptor kinase, regulates male germline cell number and tapetal identity and promotes seed development in Arabidopsis.", Current Biol. (Oct. 2002), 12(20):1718-27.
Hong; et al., "Somatic and Reproductive Cell Development in Rice Anther is Regulated by a Putative Glutaredoxin.", Plant Cell (Feb. 2012), 24(2):577-88.
Kelliher; et al., "Hypoxia triggers meiotic fate acquisition in maize.", Science (Jul. 2012), 337(6092):345-8.
Roschina; et al., "Pollen Chemosensitivity to Ozone and Peroxides", Russian Journal of Plant Physiology (Jan. 2001), 48(1):74-83.
Sheridan; et al., "The mac1 mutation alters the developmental fate of the hypodermal cells and their cellular progeny in the maize anther.", Genetics (Oct. 1999), 153(2):933-41.
Wang; et al., "Maize multiple archesporial cells 1 (mac1), an ortholog of rice TDL1A, modulates cell proliferation and identity in early anther development.", Development (Jul. 2012), 139(14):2594-603.
Xing; et al., "ROXY1 and ROXY2, two Arabidopsis glutaredoxin genes, are required for anther development.", Plant J (Mar. 2008), 53(5):790-801.
Zhao, "Control of anther cell differentiation: a teamwork of receptor-like kinases.", Sex Plant Reprod. (Dec. 2009), 22(4):221-8.

* cited by examiner

*Primary Examiner* — Stuart F Baum
(74) *Attorney, Agent, or Firm* — James S. Keddie; Bozicevic, Field & Francis LLP

(57) ABSTRACT

Certain embodiments provide a method of altering the number of archesporial cells in a developing anther of a plant in certain embodiments, the method comprises exposing the anther to redox-modulatory conditions prior to differentiation of germline cells in the anther, thereby changing the redox potential of cells in the anther and altering the number of archesporial cells in the anther. This method may be employed to increase or decrease the number of archesporial cells in a developing anther, and may be employed to produce male sterile plants.

19 Claims, 51 Drawing Sheets

FIGURE 1
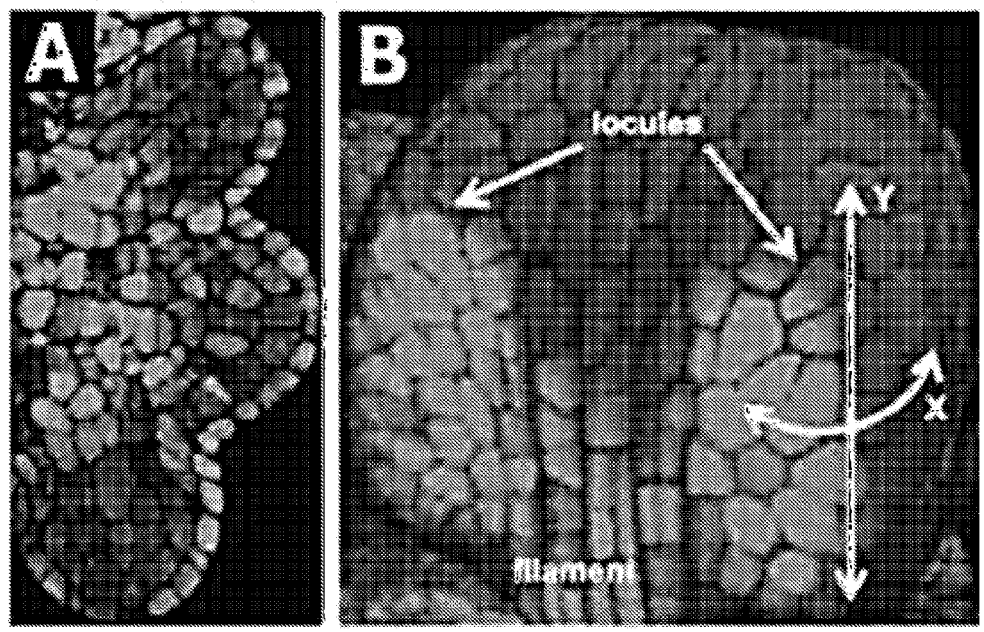
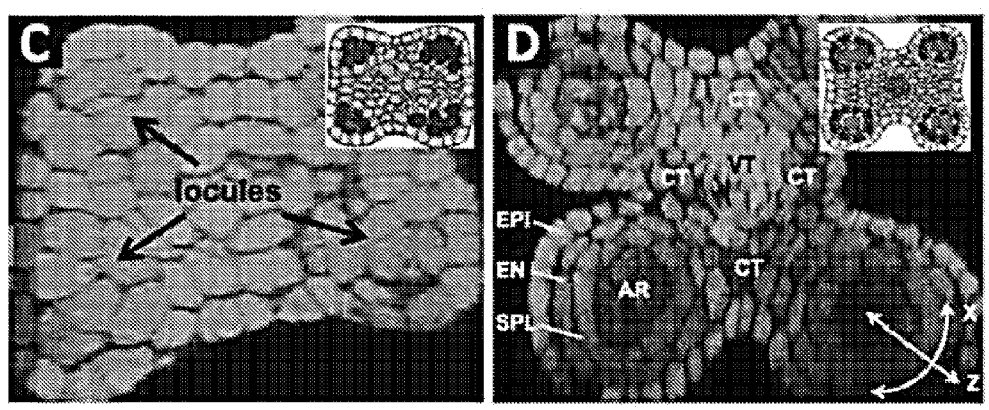

FIGURE 3
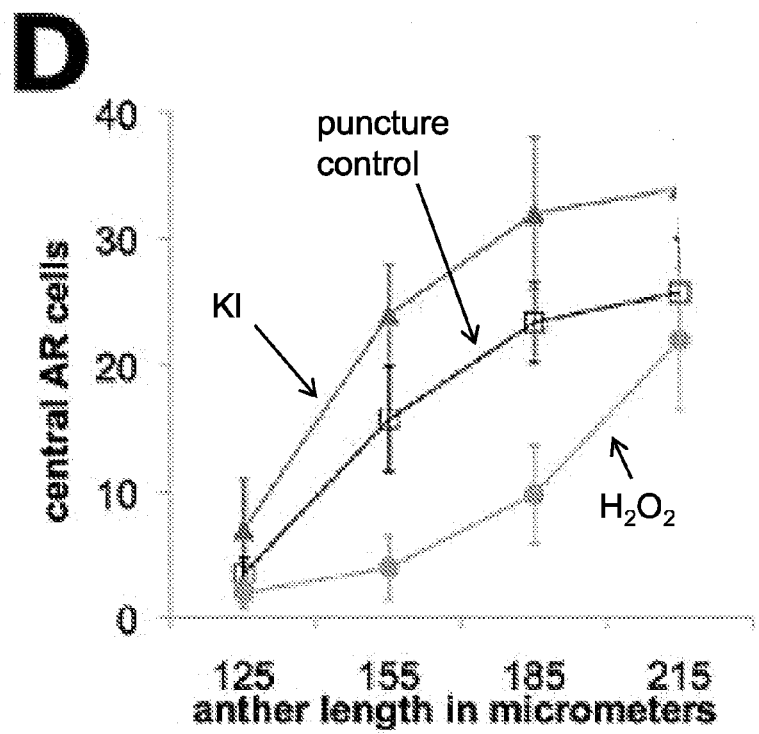
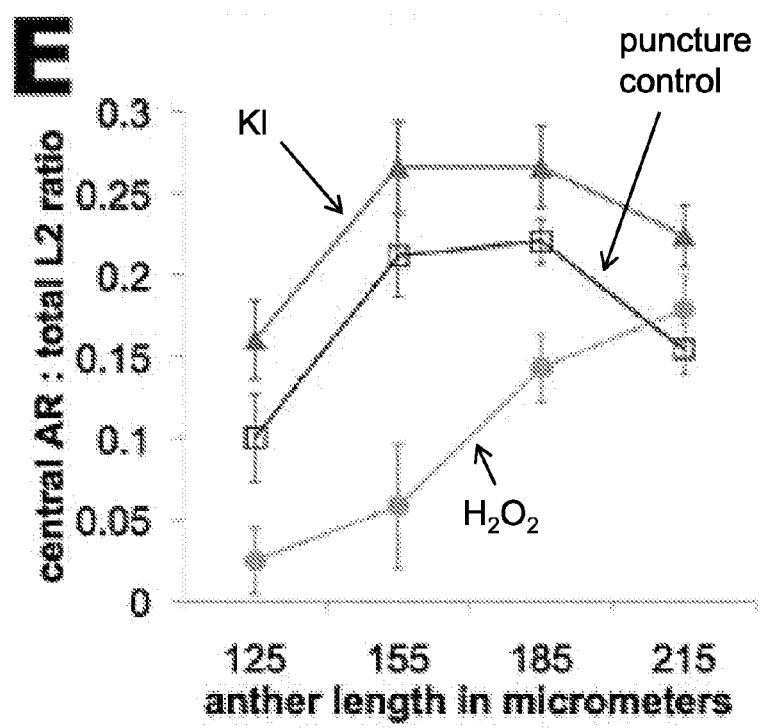

24 h period of AR specification
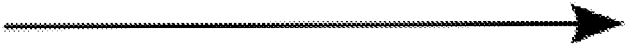

RULE: all hypoxic (inner) cells
differentiate as AR until MAC1 represses
pluripotency in surrounding ring

- MAC1 represses AR cell division until
  column of AR specified from base to tip
- Continued anticlinal division in L2-d

- Reducing environment ($N_2$, KI) -->
  excess AR and precocious periclinal
  division in L2-d cells

- Oxidizing environment ($O_2$, ROS) -->
  few AR and delayed periclinal
  division in L2-d cells

- *mac1* all internal cells differentiate
  as AR plus excess AR proliferation

FIGURE 11
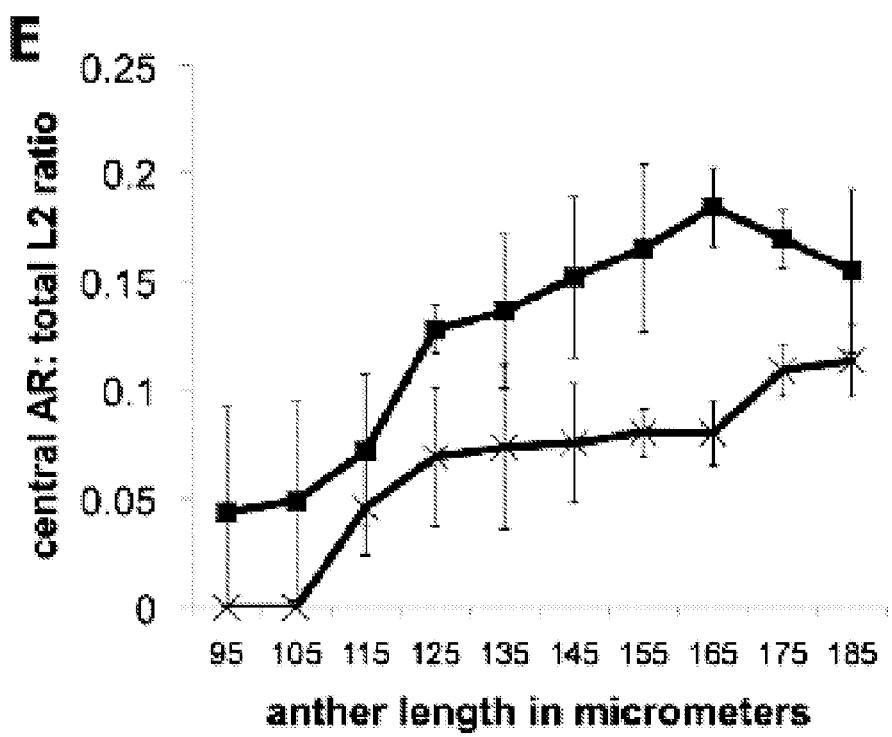
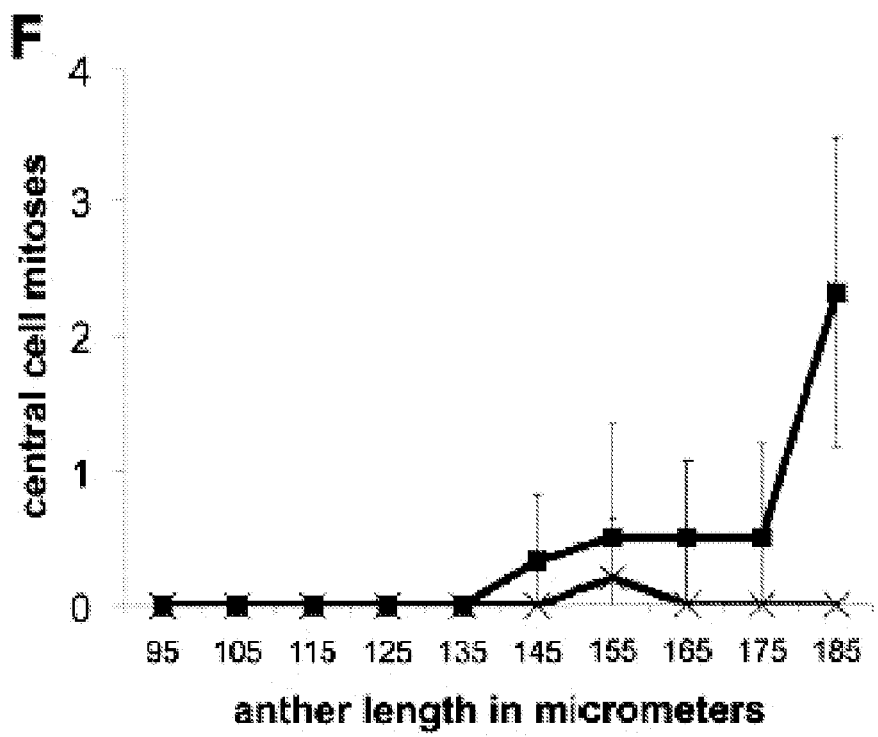

FIGURE 20

| Anther length (mm) | < 0.15 | 0.15-0.20 | 0.20-0.30 |
|---|---|---|---|
| Days following primordia stage | | 1 | 2 |
| Somatic progression | L2-d | L2-d | L2-d → SPL & EN |
| Germinal progression (count / lobe) | L2-d (0) | Specification (0 - 12) | Expansion (12 - 30) |
| Graphic depiction of a single lobe | | | |

L2-d cell
Hypoxia
MSCA1 glutaredoxin
→ AR cell fate

AR cell
MAC1 ligand

L2-d cell
→ Somatic fate

| 0.30-0.60 | 0.60-0.75 | 0.75-1.50 | 1.50-2.20 | 2.20-5.00 |
|---|---|---|---|---|
| 3-5 | 6 | 7-8 | 9 // | 30 |
| Clonal mitoses | SPL → T & ML | Clonal mitoses | Unknown role | Tapetum delivers pollen coat |
| Mitoses (30 - 100) | Mitoses (100 - 120) | Final mitoses (120 - 150) | Meiosis (150 → 600) | Maturing pollen (600) |

- Epidermis (EPI)
- Endothecium (EN)
- Middle layer (ML)
- Tapetum (T)
- Archesporial (AR) (germinal) cells Secondary parietal layer (SPL)

FIGURE 20
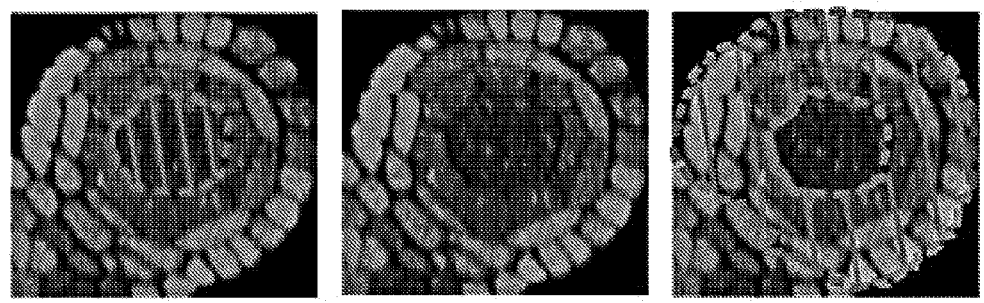
b
LCM Germinal cells
Stage: 0.30 - 0.35 mm
2500 cells / replicate
50 pg RNA / cell
LCM Somatic cells
Stage: 0.30 - 0.35 mm
40,000 cells / replicate
10 pg RNA / cell
c
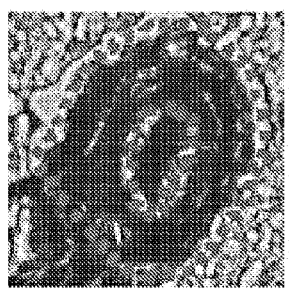
Tissue types
Somatic (EPI, EN, SPL)
Germinal (AR)
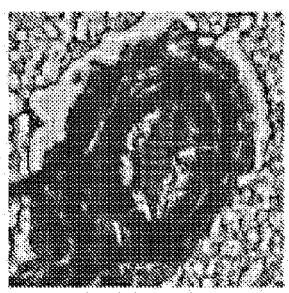
AR cell
marking
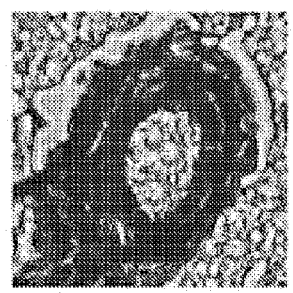
Cell removal

FIGURE 21
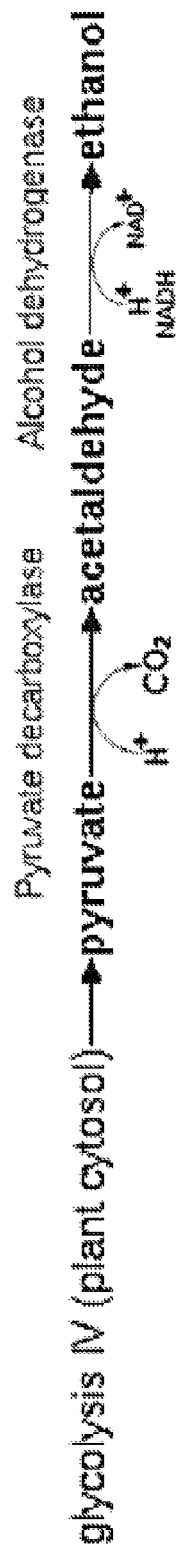
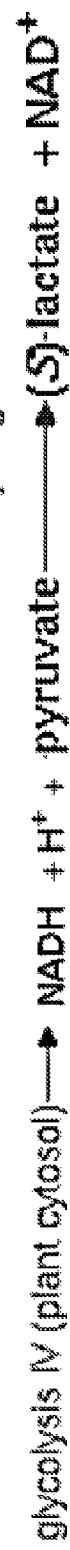

SEQUENCE LISTING

<160> NUMBER OF SEQ ID NOS: 4

<210> SEQ ID NO 1
<211> LENGTH: 20
<212> TYPE: DNA
<213> ORGANISM: Artificial sequence
<220> FEATURE:
<223> OTHER INFORMATION: Synthetic nucleotide sequence

<400> SEQUENCE: 1
aaccctactg cgaaacaact                                                   20

<210> SEQ ID NO 2
<211> LENGTH: 20
<212> TYPE: DNA

```
<213> ORGANISM: Artificial sequence
<220> FEATURE:
<223> OTHER INFORMATION: Synthetic nucleotide sequence

<400> SEQUENCE: 2
cgagaatcct gcgtcctgat                                            20

<210> SEQ ID NO 3
<211> LENGTH: 19
<212> TYPE: DNA
<213> ORGANISM: Artificial sequence
<220> FEATURE:
<223> OTHER INFORMATION: Synthetic nucleotide sequence

<400> SEQUENCE: 3
ggtggtcaca tttgatggg                                             19

<210> SEQ ID NO 4
<211> LENGTH: 18
<212> TYPE: DNA
<213> ORGANISM: Artificial sequence
<220> FEATURE:
<223> OTHER INFORMATION: Synthetic nucleotide sequence

<400> SEQUENCE: 4
ctgagcccga taccaacc                                              18
```

METHOD FOR MODULATING THE NUMBER OF ARCHESPORIAL CELLS IN A DEVELOPING ANTHER

CROSS-REFERENCING

This application claims the benefit of provisional application Ser. No. 61/598,544, filed on Feb. 14, 2012, which application is incorporated by reference herein.

GOVERNMENT RIGHTS

This invention was made with Government support under contract PGRP07-01880 awarded by the National Science Foundation. The Government has certain rights in this invention.

BACKGROUND

Sexual reproduction in multi-cellular organisms entails generation of meiotically competent germ cells within a somatic body. Developmental mechanisms responsible vary among taxa, however, most animals exhibit continuous production from stem cells specified during embryogenesis. In contrast, angiosperms are strictly vegetative until intrinsic and environmental cues trigger flowering. Within anther and carpel primordia, indeterminate floral progenitor cells differentiate as pre-meiotic archesporial (AR) cells and somatic parietal cells, but the morphogenetic mechanisms responsible remain unclear. The nature of the somatic to germinal switch, and the degree to which it is under developmental or physiological control, has until now been a botanical mystery.

SUMMARY

A method of altering the number of archesporial cells in a developing anther of a plant is provided. In certain embodiments, the method comprises exposing the anther to redox-modulatory conditions prior to differentiation of germline cells in the anther, thereby changing the redox potential of cells in the anther and altering the number of archesporial cells in the anther. This method may be employed to increase or decrease the number of archesporial cells in a developing anther In one embodiment the treatment may comprise exposing the anther to hypoxic conditions or to a reducing agent at a concentration that lowers the amount of reactive oxygen species in the cells of the anther, thereby lowering the amount of reactive oxygen species in the cells and increasing the number of archesporial cells. Increasing the number of archesporial cells in the anther may result in a plant having larger anther size and/or higher pollen production, relative to a control plant that has not been exposed to hypoxic conditions or to a reducing agent. In one case, this method may be done by placing the anther in an environment that contains less than 1% oxygen, e.g., in a gas containing at least 99% nitrogen. Alternatively the developing tassel can be immersed in redox-modulating chemical solutions by injecting fluid into the airspace surrounding the immature tassel at the stage just prior to or during archesporial cell formation.

In another embodiment, the exposing may comprise contacting the anther with an oxidizing agent (such as pure oxygen gas or chemicals) at a concentration that increases the amount of reactive oxygen species in the cells, thereby increasing the amount of reactive oxygen species in the cells and decreasing the number of archesporial cells. In certain cases, decreasing the number of archesporial cells in the anther results in a plant having smaller anther size and/or lower pollen production than a control plant that has not been subjected to the applying. In other cases, decreasing the number of archesporial cells may result in a male sterile plant. In particular cases, the oxidizing agent may be a peroxide, although any other suitable oxidizing agent may be applied.

A developing anther may be exposed to redox-modulatory conditions in a variety of different ways. For example, in one embodiment, the exposing may comprise exposing the developing anther to a gas. In another embodiment, the exposing may comprise contacting the developing anther with a liquid or gel that comprises a redox-modulatory compound, e.g., by spraying the anther or contacting the anther with a droplet. In this embodiment, the redox-modulatory compound may be dissolved in the liquid or gel, or the redox-modulatory compound is in or on a particle that is present in the liquid or gel. In particular cases, the particle may provide for extended release of the redox-modulatory compound over a period of, e.g., 1 to 5 days. In other embodiments, the applying may comprise placing a solid form of a redox-modulatory compound on the developing anther.

The method summarized above finds use in a variety of applications, such as, e.g., to increase anther size and/or increase the number of pollen produced by a plant or to make plants with a decrease in anther size and/or a decreased number of pollen. In one example, the method may be used to make a male sterile plant. This method may comprise: exposing the developing anthers in an anther of a plant, prior to differentiation of germline cells, to an oxidizing agent at a concentration that increases the amount of reactive oxygen species in cells in the anthers, thereby increasing the amount of reactive oxygen species in the cells and decreasing the number of archesporial cells in the anthers; and cultivating the plant to produce a male sterile plant. This method may further comprise crossing the male sterile plant with a another plant to produce an hybrid plant, e.g., a plant that has hybrid vigor relative to its parents. This method, as will be discussed below has significant utility in the production of hybrid monocots, e.g., corn and rice.

Also provided is a plant comprising a pre-meiotic anther having a non-heritable increase in the number of archesporial cells, relative to a plant of the same germplasm grown in air with out an application of an oxidizing agent.

BRIEF DESCRIPTION OF THE FIGURES

FIG. 20. Timeline of maize anther development and experimental design. (a) Pre-meiotic maize anther development beginning with primordia (day one), through the synchronous start of meiosis (day nine), and ending with pollen release (day 30). Cartoons diagram developmental processes for a single anther lobe. Anther primordia (<0.15 mm anther length) consist of presumptive vasculature, epidermis, and pluripotent L2-d cells. The central L2-d cells differentiate into AR during germinal specification, dependent on a positional cue triggered by hypoxia, and characterized by cell enlargement, first visible in 0.16 mm long anthers (late day one) and completed by 0.22 mm (early day two)[3]. Differentiating AR cells secrete MAC1 protein, which results in the single layer of surrounding L2-d pluripotent cells dividing periclinally to generate two somatic layers, the endothecium (EN) and secondary parietal layer (SPL), as the anther grows from 0.20-0.28 mm. These cell types proliferate for seven days prior to meiotic initiation; at 0.6 mm the SPL divides periclinally to generate the middle layer and tapetum. (b) Confocal reconstructions illustrating target tissues and hybridization strategy with balanced dye swap. (c) Demonstration of LCM Dissection of the Germinal Cells.

DEFINITIONS

Figure 1:
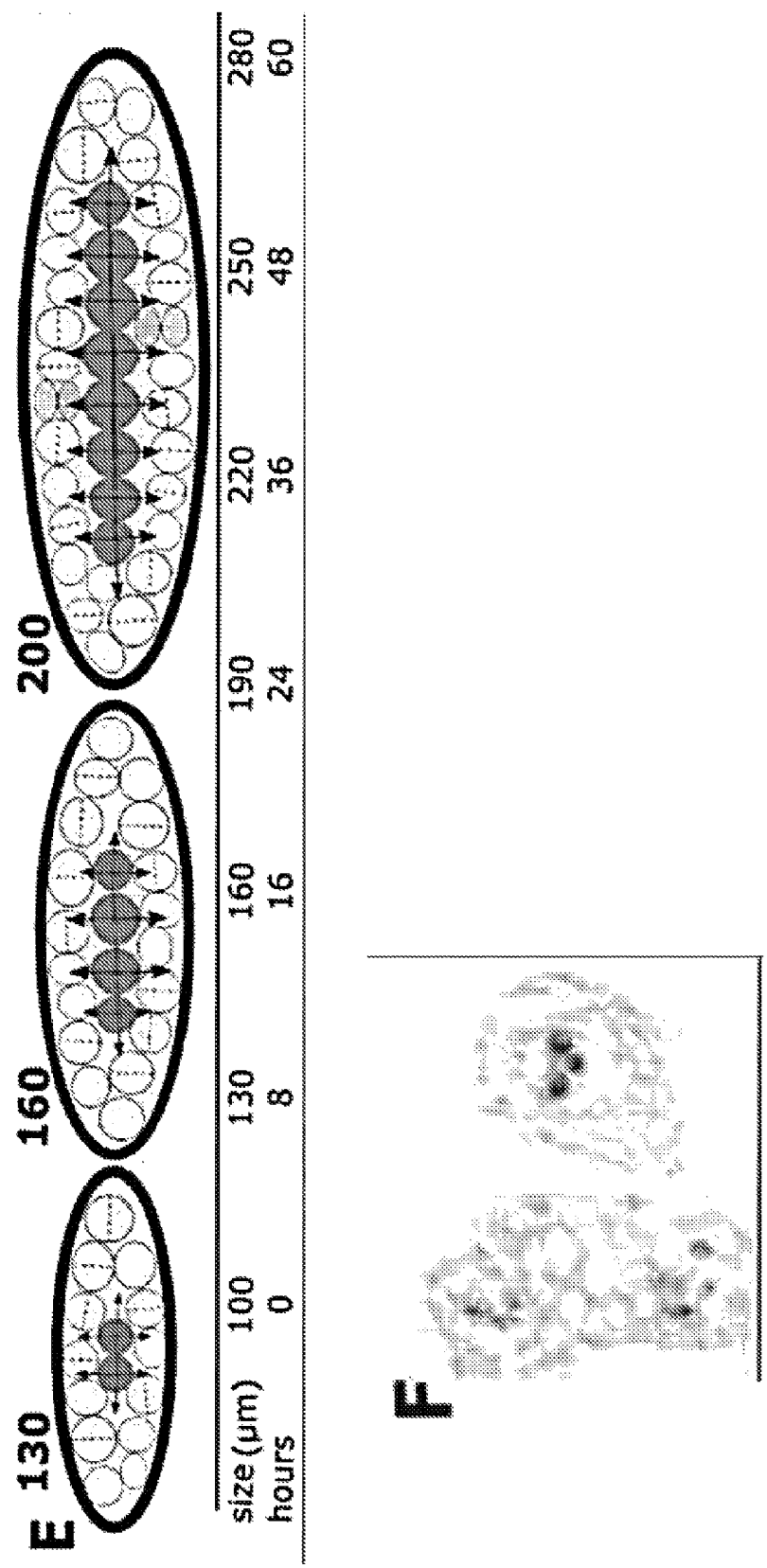
FIG. 1. Anther development in fertile and mac1. (A) Three 55 µm stamen primordial in floret. (B) 3D composite of 100 µm anther. (C,D) Transverse reconstructions bracketing period studied. Insets: representative diagrams. (C) Budding locules at 110 µm. D) Four locule cell types at 300 µm. (E) Longitudinal diagrams and timeline; arrows indicate MAC1 signaling. (F) MAC1 immunohistolocalization during (left) and post (right) AR specification. (G) Transverse reconstructions of fertile and mac1 locules. Arrows indicate AR births. Arrowheads indicate SPL/EN generative divisions. (H) AR counts in W23 and A619 inbred locules. "Both" indicates locules containing differentiated and presumptive AR. (I) AR counts in mac1 and fertile (stars: $p<0.05$). (J) Quantification of mac1 by qRT-PCR. Inset: Cellular composition of laser microdissected anthers. (K) Longitudinal section of fertile W23 anther. Green arrowheads indicate anticlinal divisions. (Pink=presumptive AR, archesporial cell; red=differentiated AR; EPI, epidermis; CT, connective tissue; VT, vascular tissue.)
Figure 1:
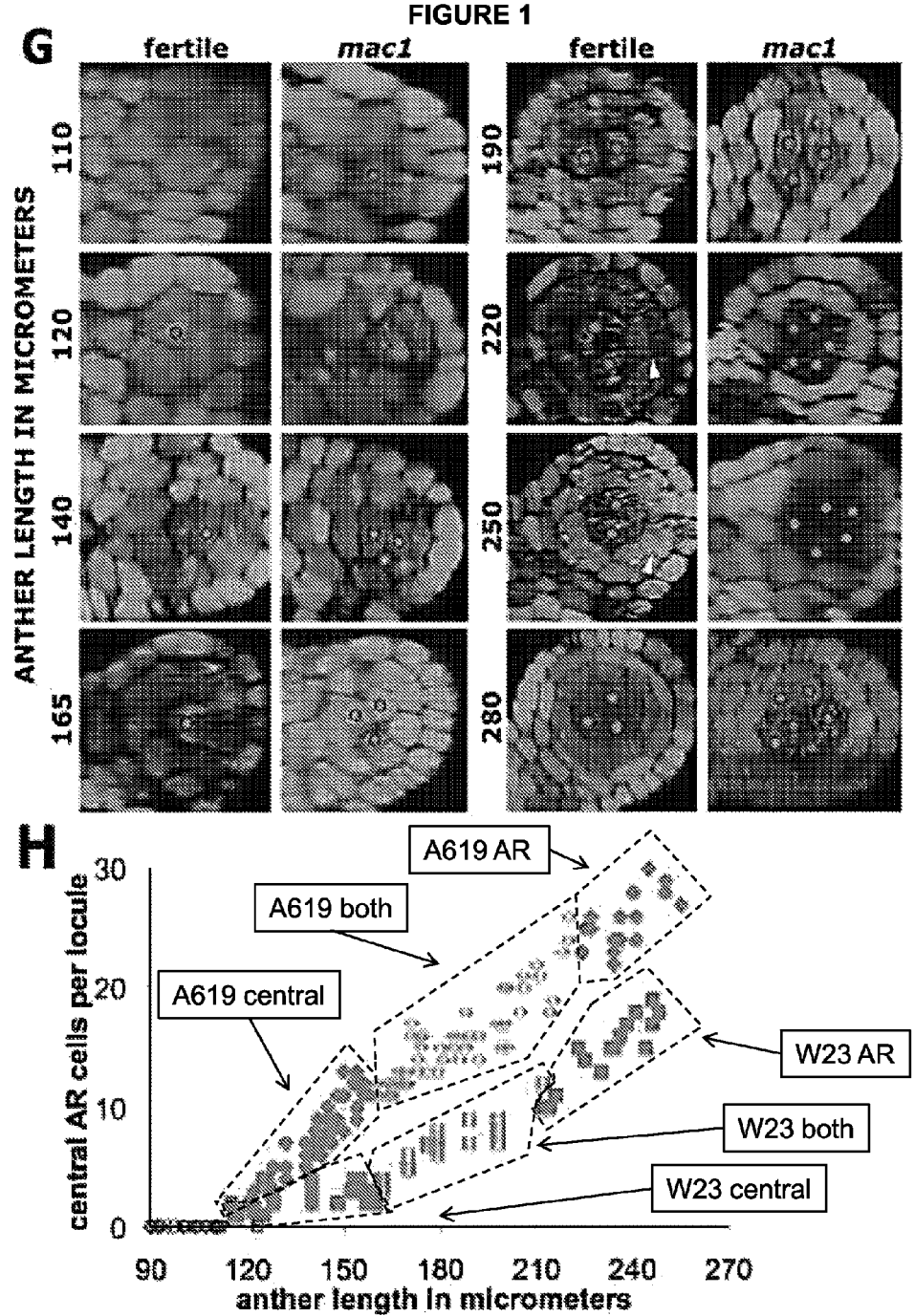
Figure 1:
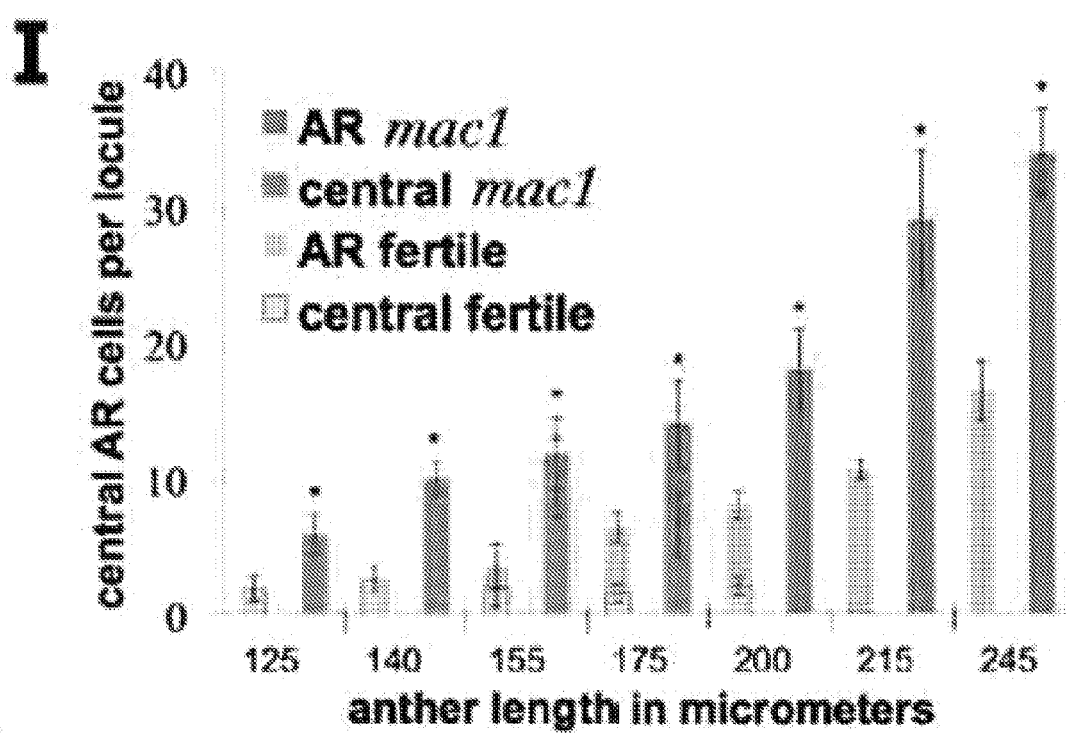
Figure 1:
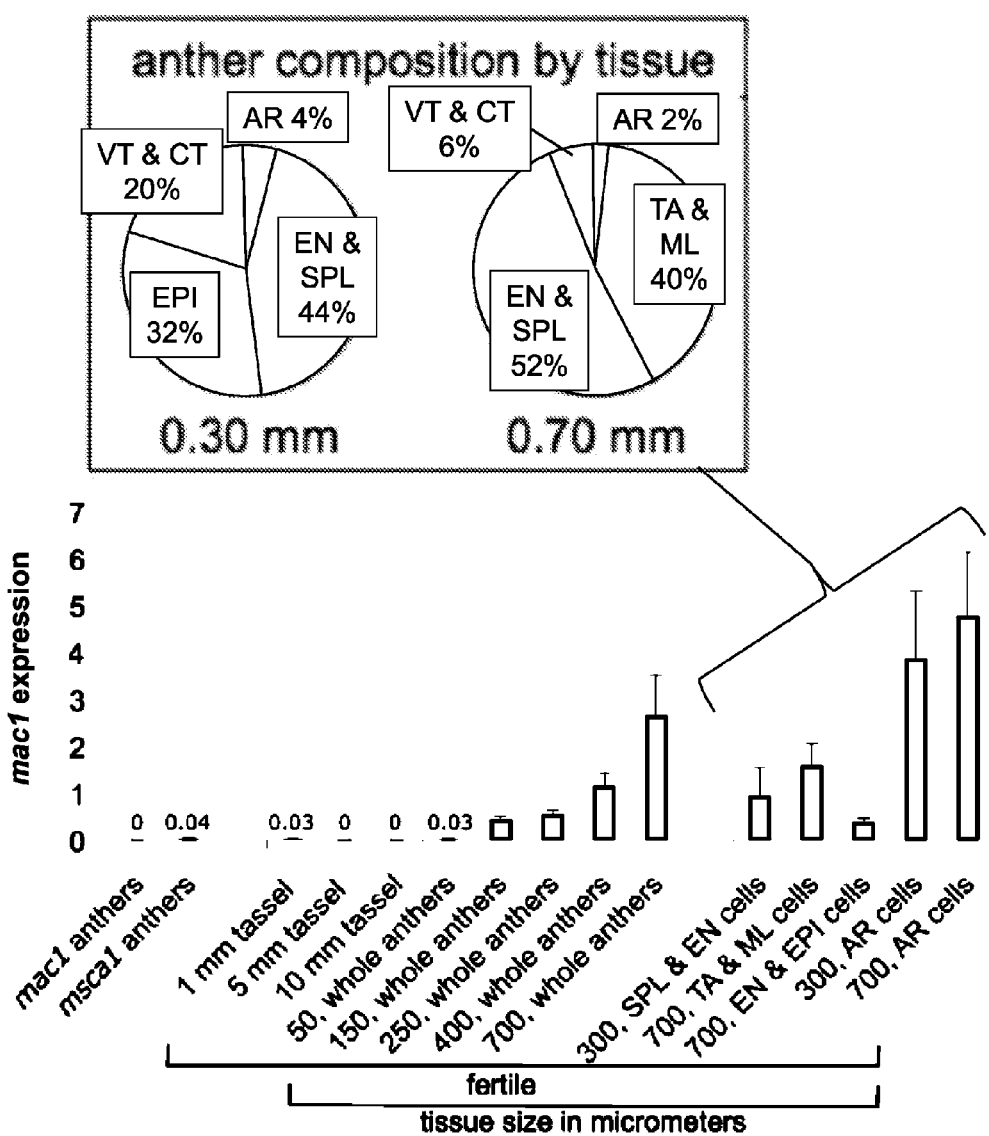
Figure 1:

Unless defined otherwise herein, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described.

All patents and publications, including all sequences disclosed within such patents and publications, referred to herein are expressly incorporated by reference.

The headings provided herein are not limitations of the various aspects or embodiments of the invention which can be had by reference to the specification as a whole. Accordingly, the terms defined immediately below are more fully defined by reference to the specification as a whole.

As used herein, the term "archesporial cell" refers to an cell in an anther primordium from which the microsporocytes of a flowering plant develop. Archesporial cells from a variety of different model monocot and dicot species are described in, e.g., Raghavan (J. Cell Sci. 1989 92:217-2; rice); Sheridan et al (Genetics. 1996 142:1009-20; maize), Sheridan et al (Genetics 1999 153: 933-41; maize); Feng et al (Development 2010 137:2409-1; Arabidopsis); Ma et al (Plant J. 2007 50:637-48; maize) and Cnudde et al (Chromosome Res. 2006 14: 919-32; petunia). These references are incorporated by reference for a description of those cells.

As used herein, the term "prior to differentiation of germline cells" refers to a stage in anther development after the stamen primordia have been initiated from a meristem and prior to the production of meiotically competent germ cells within a somatic body. This stage is considered to be early in anther development.

As used herein, the term "redox-modulatory conditions" refers to the conditions that increase the amount of reactive oxygen species in a cell relative to the same type of cell that is grown under equivalent conditions in air, i.e., the earth's atmosphere, at ground level. In other words, under this definition, air (which is composed of approximately 79% nitrogen, 20% oxygen, and 1% other gases) is not considered a redox-modulatory condition. However, air may contain components, e.g., nitrogen and oxygen, which, if they are applied at a concentration that is different their concentration in air (e.g., less then 1-% oxygen, at least 90% nitrogen, at least 30% oxygen or less than 70% nitrogen, etc.), can be considered redox-modulatory because they can increase or decrease the amount of reactive oxygen species in a cell. Redox modulator conditions can be created by exposing a developing anther to hypoxic conditions (e.g., an environment containing less than 1% oxygen), by contacting a developing anther with a redox-modulatory compound, e.g., a reducing agent or oxidizing agent, at a concentration that alters the amount of reactive oxygen species in the cells of the anther.

As used herein, the term "reducing agent" refers to a compound that donates an electron to another species within a cell, thereby reducing the oxidation state of a cell.

As used herein, the term "oxidizing agent" refers to a compound that removes electrons from another reaction in a cell, thereby increasing the oxidation state of a cell. Oxygen is a type of oxidizing agent. However, as noted above, if oxygen is used as an oxidizing agent, it must be applied at an amount that is greater than its concentration in the earth's atmosphere.

DETAILED DESCRIPTION OF EXEMPLARY EMBODIMENTS

As noted above, a method of altering the number of archesporial cells in a developing anther of a plant is provided. In general terms, the method comprises exposing the anther to redox-modulatory conditions prior to differentiation of germinal cells in the anther, thereby changing the redox potential in precursor L2-d cells (layer 2 derived cells tracing back to the floral meristem) and altering the number of archesporial cells in the anther. Because the archesporial cells develop into microsporangia cells, an increase in the number of archesporial cells leads to larger anthers and/or more pollen, and a decrease in the number of archesporial cells leads to smaller anthers and/or less pollen, or male sterility.

In certain embodiments an anther may be contacted with a reducing agent at concentration that lowers the amount of reactive oxygen species in the cells of the anther, thereby lowering the amount of reactive oxygen species in the cells and increasing the number of archesporial cells. The same effect may be obtained by subject the anther to hypoxic conditions, using, e.g., an inert gas at a concentration that makes the cells hypoxic, which lowers the amount of oxygen, and hence produces lower amounts of reactive oxygen species in the cell. In these embodiments, the concentration of oxygen in the inert gas may be less than 15%, less than 10%, less than 5%, or less then 1%. In particular cases, the gas may be composed of a single element (e.g., $N_2$ gas), although the gas may be a mixture of elements in certain cases. For example, if $N_2$ gas is used, then the $N_2$ may be present in the gas at a concentration that is greater than 80%, e.g., at least 85%, at least 90% or at least 95%, thereby creating hypoxic conditions. Several reducing agents are known in the art and include Na, Cr, Cu and Cl$^-$. Common reducing agents contain potassium, calcium, barium, sodium and magnesium, and also compounds that contain an H$^-$ ion, including NaH, LiH, LiAlH$_4$ and CaH$_2$. Reducing agents that are suitable for use in this embodiment of the method include lithium aluminium hydride (LiAlH$_4$), sodium amalgam, sodium borohydride (NaBH4), compounds containing the Sn2+ ion, such as tin(II) chloride, sulfite compounds, hydrazine (Wolff-Kishner reduction), zinc-mercury amalgam (Zn(Hg)) (Clemmensen reduction), diisobutylaluminum hydride (DIBAH), lindlar catalyst, oxalic acid ($C_2H_2O_4$), formic acid (HCOOH), ascorbic acid ($C_6H_8O_6$), phosphites, hypophosphites, phosphorous acid, dithiothreitol (DTT) and several compounds containing $Fe^{2+}$, such as iron(II) sulfate. Lowering the amount of reactive oxygen species increases the number of archesporial cells in the anther results in a plant having larger anther size and/or higher pollen production, relative to a control plant that has not been subjected to the applying, i.e., a control plant that has not been exposed to the reducing agent or to a gas or hypoxic conditions. An increase in the number of archesporial cells is desirable for production of products that are made from pollen and/or anthers. For example, an or decrease increase in the number of archesporial cells is desirable in saffron production (which is produced from carpels), for the production of pollen that can be used in dietary supplements, for the production of medicinal compounds, or to produce allergen for inoculations and testing.

In other embodiments, an anther may be contacted with an oxidizing agent at a concentration that increases the amount of reactive oxygen species in cells of the anther. This decreases the number of archesporial cells. Several oxidizing agents are known in the art and include oxygen ($O_2$), ozone ($O_3$), peroxide such as hydrogen peroxide ($H_2O_2$) and inorganic peroxides, fluorine ($F_2$), chlorine ($Cl_2$), and other halogens, nitric acid ($HNO_3$) and other nitrates, sulfuric acid ($H_2SO_4$), persulfuric acids ($H_2SO_5$ and $H_2SO_8$), chlorite, chlorate, perchlorate, and other analogous halogen compounds, hypochlorite and other hypohalite compounds, including bleach (NaClO), hexavalent chromium compounds such as chromic and dichromic acids and chromium trioxide, pyridinium chlorochromate (PCC), and chromate/dichromate compounds, permanganate compounds, sodium perborate, nitrous oxide ($N_2O$). Increasing the amount of reactive oxygen species decreases the number of archesporial cells in the anther results in a plant having smaller anther size and/or lower pollen production or male sterility, relative to a control plant that has not been subjected to the applying, i.e., a control plant that has not been exposed to the oxidizing agent. Again, if oxygen is used as an oxidizing agent, it is used at a concentration that provides an increased concentration of oxygen in the cells relative to cells in a control plant grown in the earth's atmosphere, which leads to more reactive oxygen species in the cells of the developing anther.

A developing anther of a plant may be exposed to redox-modulatory conditions in a variety of different ways. For example, in one embodiment, the exposing may comprise exposing the developing anther to a gas. In this embodiment, at least part of a plant (e.g., the entire plant or an inflorescence) may be enclosed in an enclosure (e.g., in a bag or, if many plants are being treated, in a tent) and a gas (e.g., nitrogen, oxygen, or another gas) may be added to the interior of the enclosure, thereby increasing or decreasing the oxygen concentration in the enclosure relative to the outside air. In another embodiment, the exposing may comprise contacting the developing anther with a liquid (e.g., by spraying the liquid) or gel that contains a redox-modulatory compound. Alternatively the developing tassel can be immersed in redox-modulating chemical solutions, e.g., by dipping or injecting fluid into the airspace surrounding the immature tassel at the stage just prior to or during archesporial cell formation.

The redox-modulatory compound may be dissolved in a medium that is applied to the anther, or it may be present in or on a particle that is present in the medium that is applied to the anther. In another embodiment, the exposing may by placing a solid form of the redox-modulatory compound on the developing anther, e.g., a crystal or particle containing the redox-modulatory compound. As would be apparent, the redox-modulatory compound should be applied so that decrease or increase in reactive oxygen species occurs at an appropriate time in anther development, i.e., after anther primordia have formed but prior to differentiation of germinal cells. The optimal time frame for altering the number or presence of germinal cells is to initiate treatments just before or at the onset of germ cell specification. This period occurs in 100-200 micrometer length maize anthers (Kelliher & Walbot 2012). In other species, anther size is smaller at the comparable stage: stage 5 of *Arabidopsis* floral development (Smyth, D. R., Bowman, J. L., and Meyerowitz, E. M. (1990). Early flower development in *Arabidopsis*. Plant Cell 2, 755-767) or tobacco (*Nicotiana tabacum* Goldberg, R. B., Beals, T. P., and Sanders, P. M. (1993). Anther development: Basic principles and practical applications. Plant Cell 5, 1217-1229 In rice (Itoh, J-I. et al. 2005. Rice plant development: from zygote to spikelet. Plant & Cell Physiol. 46: 23-47) the correct stage is designated as stage Sp6 formation of stamen primordia extending into stage SP7. In lily, the stage is prior to the 1 mm length anther (Wang et al. 1992. Patterns of protein accumulation in developing anthers of *Lilium longiglorum* correlate with histological events. Amer. J. Botany 79: 118-127. In *Petunia hybrida*, the appropriate stage is Stage 1 (Gillman et al. 2009, chapter 6 in Petunia: Evolutionary, Developmental and Physiological Genetics, ed. T. Gerats and J. Strommer). Information on early anther development is available for additional species in D'Arcy, W. G. and R. C. Keating's 1996 book The anther: form, function, and phylogeny. This period of time may vary from plant to plant. However, because similar morphological events occur in all plants, the appropriate time period for application of the redox-modulatory compound may be readily determined. The optimal period may be experimentally determined. In particular cases, the entire plant may be exposed to the redox-modulatory conditions. In other embodiments, only an inflorescence (e.g., the tassel of a maize plant or other monocot) may be exposed to the redox-modulatory conditions. In particular cases, the anther may be exposed to the redox-modulatory conditions more than once. In certain cases, an exposure may be for extended for a period of time, e.g., 6 hr to 1 week, or 1 to 5 days, as desired.

A redox-modulatory compound can be applied to a plant either by itself or as a formulation that also contains an agronomically acceptable carrier and, optionally, other active ingredients. By "agronomically acceptable carrier" is meant any liquid or solid substance that can be used to dissolve, disperse, or diffuse a redox-modulatory compound without impairing the effectiveness of the compound and which by itself has no significant detrimental effect on the soil, equipment, crops, or agronomic environment. Such compositions include liquid or solid formulations or solutions, including wettable powders, emulsifiable concentrates, dusts, granules, pellets, aerosols, flowable emulsion concentrates, suspensions, and solutions, which may be prepared according to any suitable method. A formulation containing a redox-modulatory compound can be diluted with an agronomically suitable liquid or solid carrier. Such compositions can also include one or more agronomically acceptable adjuvants such as anionic, cationic, or nonionic surface-active agents (wetting agents, spreading agents, dispersing agents, suspending agents, and emulsifying agents), conditioning agents, sticking agents, adhesives, etc. Examples of useful adjuvants can be found in "Detergents and Emulsifier's Annual" (John W. McCutcheon, Inc.).

A redox-modulatory compound may in certain cases be administered as a liquid or wettable powder, containing as a conditioning agent one or more surface-active agents in amounts sufficient to render the redox-modulatory compound readily dispersible in water or in oil. The incorporation of a surface-active agent into the compound can enhance its efficacy. Suitable wetting agents include but are not limited to alkyl benzene and alkyl naphthalene sulfonates, sulfonated fatty alcohols, amines or acid amides, long chain acid esters of sodium isothionate, esters of sodium sulfonsuccinate, sulfated or sulfonated fatty acid esters, petroleum sulfonates, sulfonated vegetable oils, ditertiary acetylenic glycols, polyoxyethylene derivatives or alkylphenyls (particularly isooctylphenol and nonylphenol) and polyoxyethylene derivatives of the nono-higher fatty acid esters of hexitol anhydrides (e.g., sorbitan). Surfactants include, but are not limited to, the dihexyl ester of sodium sulfonsuccinic acid, POE 20 sorbitan monolaurate, and octylphenoxy polyethoxy ethanol. Wettable powders or dispersable granules are water-dispersible compositions containing one or more active ingredients, an inert solid extender, and one or more wetting and dispersing agents. The inert solid extenders may be of mineral origin such as the natural clays, diatomaceous earth, salts and synthetic minerals, derived from silica and the like. Examples of such extenders include kaolinites, attapulgite clay, salts and synthetic magnesium silicate.

A redox-modulatory compound can also be dissolved in any suitable solvent, including but not limited to one or a mixture of the following: water, alcohols, ketones, aromatic hydrocarbons, halogenated hydrocarbons, dimethylformamide, dioxane, and dimethylsulfoxide. The concentration of the redox-modulatory compound in the resulting solution may be in the range of about 2% to about 98% by weight, e.g., from about 20% to about 75% by weight.

Wettable powders suitable for spraying are mixtures of a redox-modulatory compound, a finely divided solid (such as a clay, an organic silicate or carbonate, or a silica gel), and a wetting agent, sticking agent, and/or dispersing agent. The concentration of the active ingredient(s) in such powders is generally between about 20% and about 98% by weight, e.g., between about 40% and about 75% by weight. A dispersion agent is optionally present in a concentration of about 0.5% to about 3% by weight of the composition. A wetting agent may constitute from about 0.1% to about 5% by weight of the composition.

A dust containing a redox-modulatory compound may also be employed, e.g., one made from a finely divided inert organic or inorganic solids such as a botanical flour, farina, diatomite, silicas, silicates, carbonates, and clays. One method for preparing a dust is to dilute a wettable powder with a finely divided carrier. A dust concentrate containing from about 20% to about 80% of the redox-modulatory compound can be diluted to a final concentration of about 1% to about 10% by weight of the dust.

Particulate (e.g., granular) formulations can be prepared by impregnating the active ingredient(s) into a solid material. A solution of a formulation in a volatile organic solvent is sprayed or mixed with the granular solid and the solvent may be removed by evaporation. The granular material can have any suitable size, e.g., 11 to about 60 mesh. The redox-modulatory compound may represents about 2% to about 15% by weight of the formulation. Alternatively, the formulation can be incorporated into controlled-release particulate formulations by standard methods, e.g., by encapsulation by interfacial polymerization and coacervation; dissolving the active ingredient in a solution together with a polymer followed by solvent evaporation; by mixing the active ingredient with a wax or polymer (by mixing dry ingredients followed by melting the mixture or by mixing the active ingredient with a molten wax or polymer, followed by solidification of the mixture), then producing particles of the mixture by prilling, milling, extrusion, spray chilling, etc. The active ingredient generally represents between about 5% and about 50% of such a controlled-release formulation.

If a salt is employed, the salt may be formulated and applied as an aqueous solution at a concentration of between about 0.05% to about 50% by weight, e.g., from about 0.1% and about 10% by weight and applied to plants in this form. Such solutions can be prepared as concentrates that are diluted with an aqueous solvent or other appropriate solvent to the desired concentration for use. Such solutions optionally include a surface active agent and/or one or more auxiliary materials to increase the activity of the active ingredient, such as glycerin, methylethylcellulose, hydroxyethyl cellulose, polyoxyethylenesorbitan monooleate, polypropylene glycol, polyacrylic acid, polyethylene sodium malate, or polyethylene oxide, etc.

The formulation described above of the invention can be applied by conventional method, including, but not limited to mechanical application and manual application. For low-volume applications a solution of the compound may be used. In one embodiment, each inflorescence is individually sprayed with a controlled release formulation such that the redox-modulatory compound is released over a period of time, e.g., over 1-5 days, thereby changing the redox potential of cells at the appropriate period of development. An anther may also receive multiple doses of the compound, if necessary. The optimum formulation, volume, concentration, application rate, timing of application (including stage of plant development), and method of application will depend on a variety of factors such as plant type, soil type, fertility, environmental factors, etc.

As noted above, the subject method may be used to induce male sterility in plants in a method that comprises applying a redox-modulatory compound to an anther of a plant prior to differentiation of germline cells in the anther, thereby changing the redox potential of cells and altering the number of archesporial cells in the anther; and cultivating the plant to produce a male sterile plant. The plants made by this method generally comprise a pre-meiotic anther having a non-heritable increase in the number of archesporial cells, relative to plant of the same germplasm grown in air without an application of an oxidizing agent. The method may further comprise crossing the male sterile plant with another plant to produce a hybrid plant. The ability to produce male sterile plants is particularly valuable for the production of seed that give rise to hybrid plants that have greater vigor than its inbred parents.

For hybrid seed production in the field, the two parent strains to be crossed may be planted in alternate sections, rows, or groups of rows. The female parent is treated as described above in order to render the female parent male sterile. Pollen from the male (untreated) parent then fertilizes the female parent, either by means of human intervention or by a natural process, such as wind-borne pollination. The seed produced by the female parent is an $F_1$ hybrid, which is then collected by any suitable means. Plants can be crossed by either natural or mechanical techniques. Natural pollination occurs when pollen is transported by gravity, wind, pollinating insects or animals or other natural vectors from the male reproductive parts of a flower to the receptive portions of the flower. In monoecious crops, such as maize, the male and female flower parts are positioned at different locations on the same plant. In dioecious plants, there are separate male and female plants.

In one embodiment, seed produced is a first generation seed capable of being grown into an $F_1$ hybrid plant, where both the first and second parents of the hybrid are inbred plants. In another embodiment, one or both of the first and second parent plants are themselves hybrids. In one embodiment, this method comprises: (a) planting seeds of a first and a second parent plant; (b) growing the first and second parent plants; (c) treating at least the first plant so as to make it male sterile, as described above; and (d) cross-pollinating the treated plant with pollen from the second parent plant. Both parental plants may be allowed to continue to grow until maturity or the male rows may be destroyed after flowering is complete. Therefore, in certain embodiments, this method may include the next step of: (e) harvesting seeds resulting from the cross-pollinating. Only seeds from the female parental plants are generally harvested to obtain outcrossed seeds. The collected seed represents a valuable commercial product which can be sold to farmers, processed, or employed in further breeding programs.

The method described above and exemplified below may be readily adapted for use in the production of hybrid dicotyledonous crops (including, but not limited to, sugar beet, sugarcane, potato, sweet potato, lettuce cabbage, tea, radish, turnips, garlic and onion) and monocotyledonous crops, including, but not limited to, graminaceous crops such as wheat, barley, maize, rice, sorghum, millet, oats, rye, triticale, turf and forage grasses, etc.

In order to further illustrate the present invention, the following specific examples are given with the understanding that they are being offered to illustrate the present invention and should not be construed in any way as limiting its scope.

EXAMPLES

Maize anthers consist of four pollen-containing sacs, called lobes, surrounding a central vasculature (VT); together these form a butterfly shape in transverse-section. Anther development begins with three stamen primordia initiating from a floret meristem (FIG. 1A) and transitioning to the butterfly shape with locule protrusion (FIGS. 1, B and C). After two days and a 3-fold increase in anther length and girth accomplished by cell division with a constant average cell size, differentiated AR cells are located in the center of locules, surrounded by two concentric rings of somatic cells, the secondary parietal layer (SPL) and endothecium (EN), enclosed by the epidermis (EPI) and connective tissue (CT) (FIG. 1D). Over seven days AR cells proliferate, differentiate as pollen mother cells (PMC), and initiate meiosis. Meanwhile each somatic cell type exhibits a distinctive pattern of proliferation and expansion. Multi-potent SPL cells divide periclinally once and daughter cells terminally differentiate into middle layer (ML) and tapetum (TA), which surrounds the PMCs to support later pollen maturation.

Figure 6:
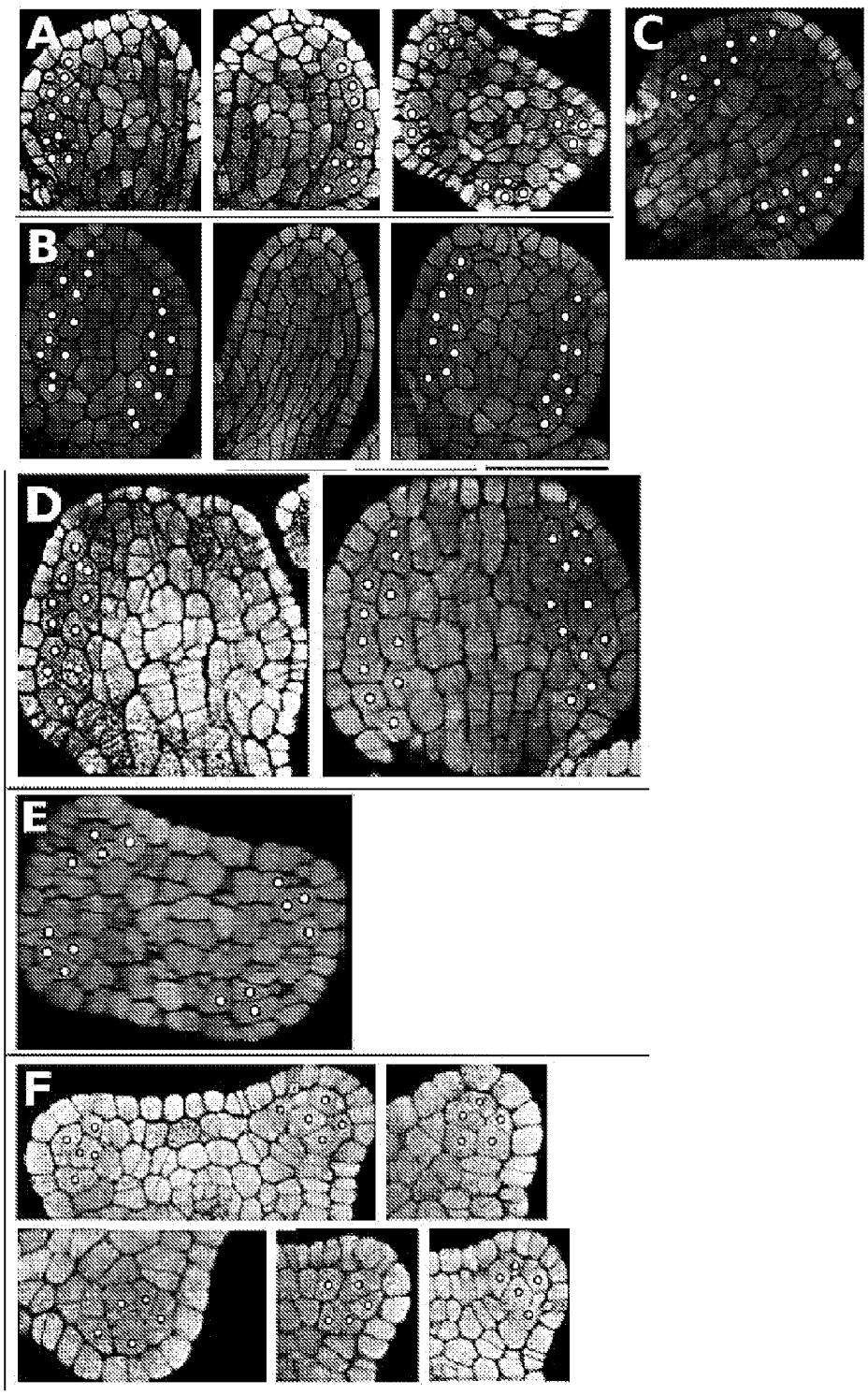
FIG. 6. L2-d progenitor cells (white dots) in W23 and A619 fertile anthers. The cells in these images reside in budding locules and will give rise to either somatic or germinal cell types or both. (A) 90 µm anther: longitudinal images (left, center) and transverse reconstruction (right). Cells were only marked that were within or very nearby the locule bulge in all views. (B) 105 µm anther with adaxial locules (left), central vasculature, which is composed of organized cell columns (center), and abaxial locules (right). Below, three transverse reconstructions of the same anther showing single locules. (C) Longitudinal image of 108 µm anther. (D) Two longitudinal images of 110 µm anthers. (E) 115 µm anther transverse reconstruction with 3-4 L2-d cells in each budding locule. (F) 118 µm anther, transverse images of different parts of the four locules. One of the locules (top left) contains a single presumptive AR cell (pink) derived from division of an internal L2-d progenitor. This cell was designates an AR cell because of its position surrounded completely by other L2-d locule cells in the complete series of confocal images.

Based on microscopic evaluation, it was believed that archesporial and parietal cells arise simultaneously from an asymmetric cell division (ACD) of an enlarged hypodermal cell at the apex of each locular arch when locules contain few Layer 2-derived cells (L2-d cells, tracing back to the second meristematic layer). Because rigid walls prohibit plant cell movement, these two cell types establish the lineages ultimately resulting in anther functional anatomy with further differentiation requiring continuing positional cues. Despite widespread invocation of lineage, hypodermal cells and ACD have not been rigorously documented. At the budding stage, there are 15-20 haphazardly arranged globular L2-d cells in a maize locule (FIG. 1C and FIG. 6). Locular arch regions (opposite connective tissue) grow rapidly with cellular volume doubling before division; consequently, enlarged cells are expected in the arch keystone position from the growth pattern. Direct measurement of division planes and frequency plus cell numbers and volumes during fate setting is required to assess the lineage model. Maize anthers were selected because fate decisions occur when anthers are large enough to dissect, hundreds of near-synchronous anthers occur on the male-only tassel, anther length correlates well with developmental stage, and it is a key agricultural crop.

Example 1

The Multi-Clonal Germline Emerges Centrally from a Field of Pluripotent Progenitors Fertile W23 inbred anthers were stained with propidium iodide and imaged in Z-stack using a Leica SP5 confocal microscope (6). The ontogeny of locular cell types was cataloged over ~2.5 days as anthers grew in length from 100 to 300 µm. From reconstructions summarized in longitudinal perspective (FIG. 1E) it was immediately clear that germinal cells are multiclonal: divisions generating AR cells occur in multiple progenitors first found centrally proceeding towards anther tip and base; ultimately 8-12 AR cells are born in just 30 hours (FIG. 1E, 1H, 1K, and FIG. 7). The morphological characteristics of pre-meiotic cells are well established (18). These traits are not visible in the first presumptive AR cells seen in ~120 m anthers, but ~10 h later starting at 160 m these definitive characteristics distinguish AR from the surrounding ring of L2-d: enlargement, non-rectilinear shape, a mottled, dark cytoplasmic stain, and a 2 µm-wide unstained boundary. A molecular marker for AR fate acquisition, MAC1 protein becomes highly elevated in AR cells (FIG. 1F)[1].

Figure 8:
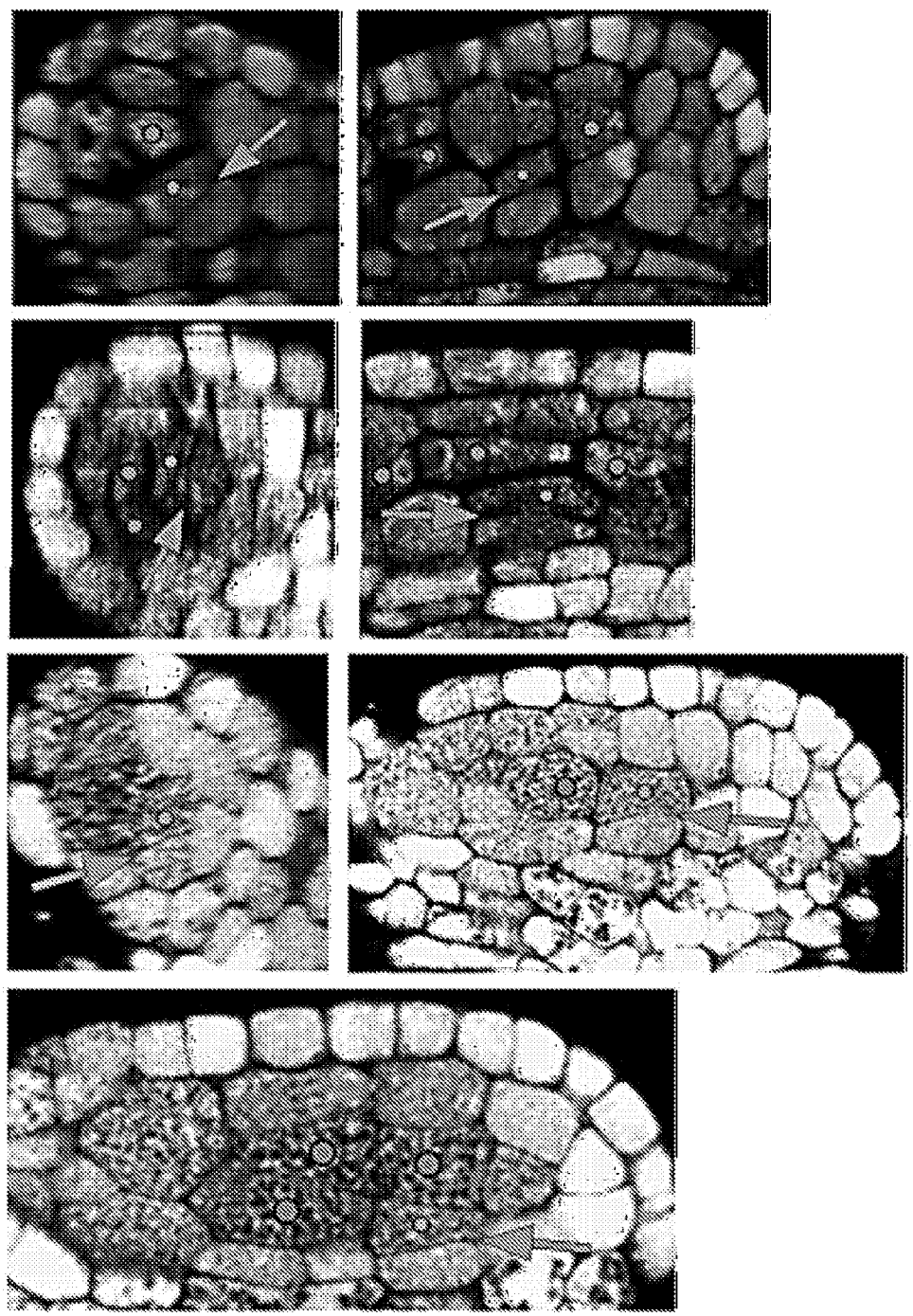
FIG. 8. Lineage does not dictate somatic/germinal fate, because AR-generative divisions occur in internal progenitor cells as well. Here we show divisions in internal or "basal" (distant from the locular arch) progenitor cells giving rise to central AR and subtending somatic daughter cells adjacent to the connective tissue. Images are from A619 inbred anthers. A619 anthers ultimately produce two columns of AR cells before forming a full SPL/EN bilayer, and the divisions that place those AR centrally come from different parts of the locule, showing that all locule initials have the capacity to generate AR in this inbred line. Left, longitudinal section with presumptive AR born from an internal progenitor that is also giving rise to a daughter within the somatic column. Differentiated AR are visible above and to the right of the presumptive AR. Top, three transverse reconstructions with internal AR births into columns that already contain at least 1 AR. Bottom, three longitudinal images with internal AR births into columns that already contain AR.
Figure 9:
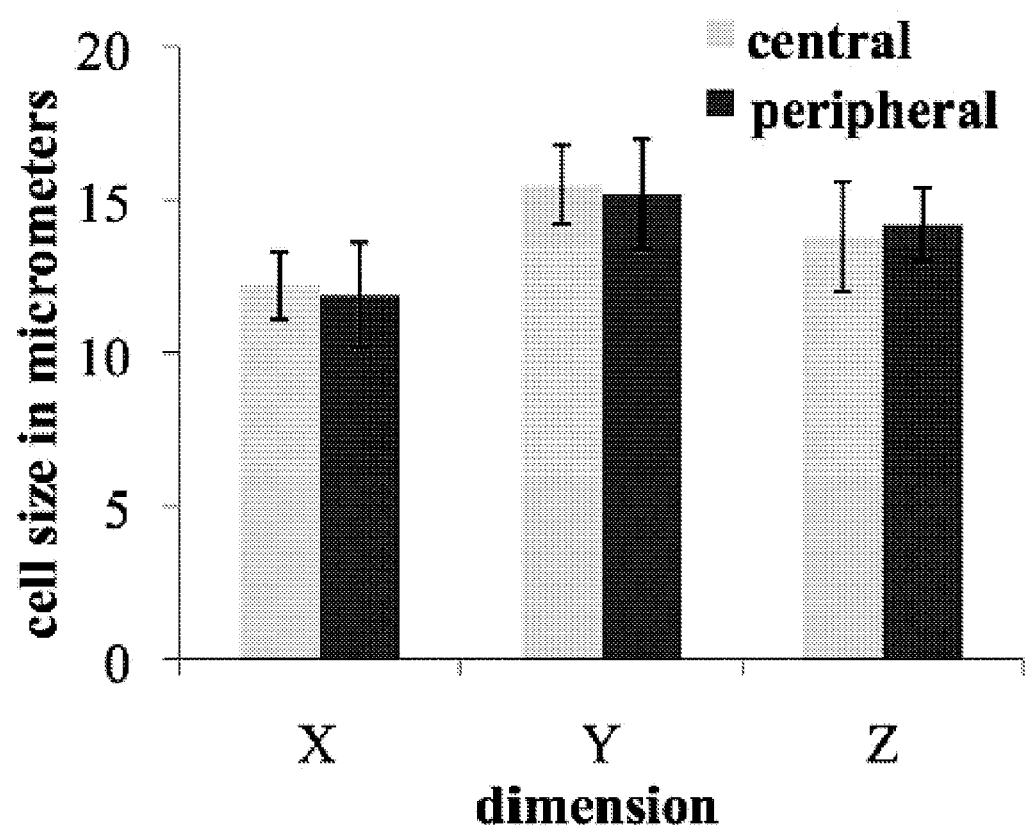
FIG. 9. AR-generative divisions are symmetric. The dimensions of presumptive AR cells and somatic peripheral sisters are equal in W23. Measurements were made with the length tool in the Volocity software package (Perkin Elmer, version 5.1.1) in the circumferential (X), longitudinal (Y), and radial (Z) dimensions (N=48). Values are averages+/− SD indicated by the error bars. There was no significant difference in any dimension.

For each AR birth, the pluripotent parent cell was identified by the thin wall shared with a sister L2-d. In W23 most progenitors were located at the keystone position viewed transversely (63%, 67/106), as posited in the lineage model, 21% were lateral (22/106), and 16% were basal (17/106) (FIG. 8). These observations suggested that all L2-d locule cells are competent to differentiate as germinal or somatic. The defining AR characteristic is walls that are shared only with L2-d neighbors, while these neighbors share walls with either the EPI or CT. There was no evidence for ACD (FIG. 9), but this does not rule out a molecular asymmetry.

Figure 7:
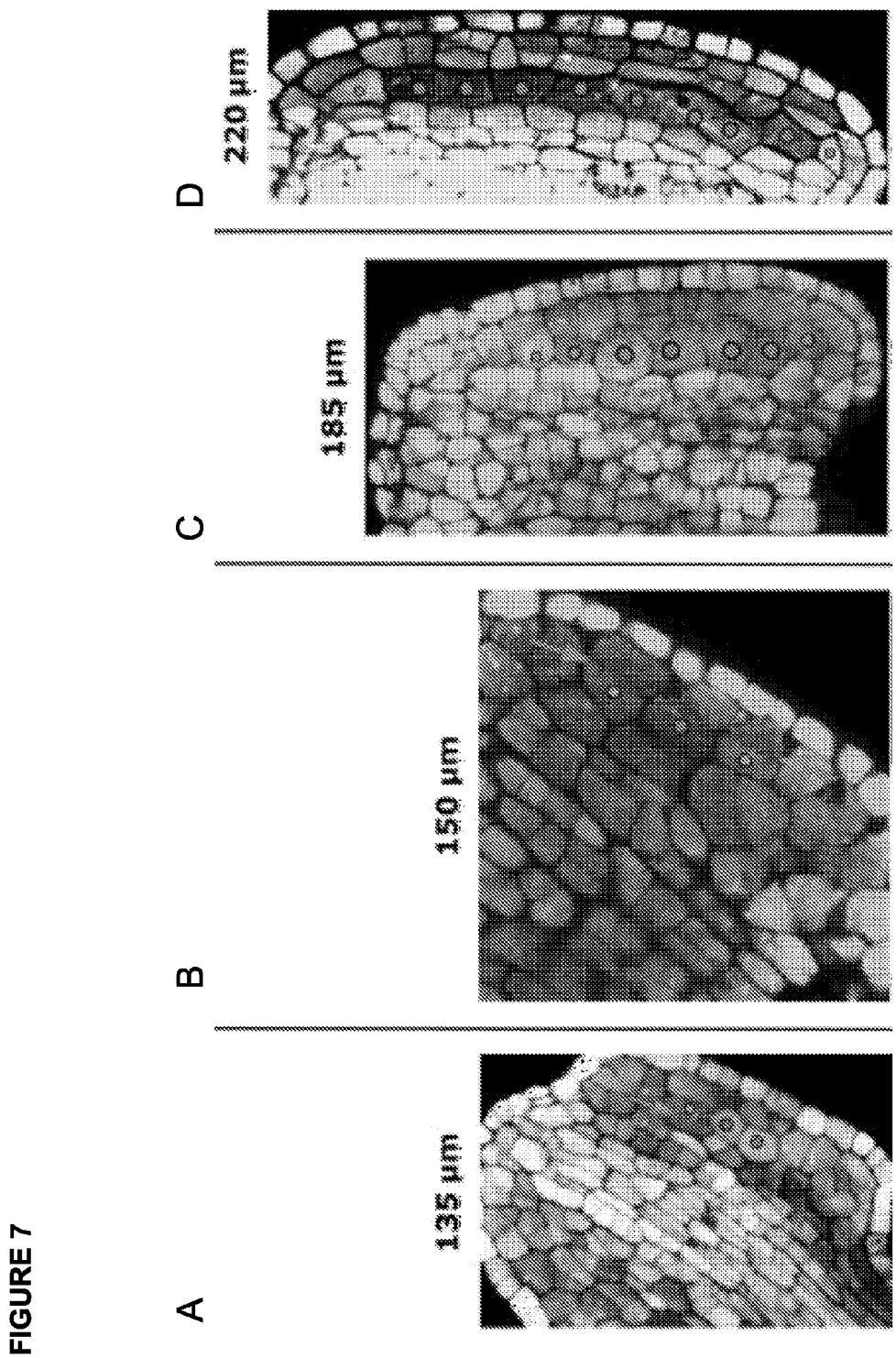
FIG. 7. AR specification in W23 fertile anthers. (A-D) Specification of AR cells initiates in the center of the locule viewed longitudinally and proceeds towards the tip and base. AR-generating divisions appear symmetric and the morphological characteristics of AR cells are not apparent at first. The defining characteristics of AR cells with our stain under confocal microscopy are slight enlargement, amorphous shape, a small gap between cells, and a dark, diffuse cytoplasmic stain. In transverse sections for light microscopy, there is no gap: AR cells have thin adjoining walls. The difference between the two types of microscopic observation probably results from the fixative used (ethanol in the propidium iodide/confocal protocol; formaldehyde for light microscopy). For all supplemental figures: Pink dots: presumptive AR cells; red dots: differentiating AR cells; pink arrows: cell walls separating presumptive AR and somatic sister cell; white arrowheads: somatic periclinal divisions generating EN and SPL; green arrowheads: somatic length-adding anticlinal divisions in the presumptive endothecium. (A) The two AR cells (red dots) do not have the normal characteristics of AR cells yet, but they are in the center of the locule and are slightly larger than neighbors. The pink dot marks a presumptive AR derived from division of an internal progenitor cell. (B) Two new presumptive AR cells are recently born above and below a differentiating AR cell. (C) Four AR with characteristic enlargement with three new presumptive AR recently born above and below the column. (D) Eight AR cells with characteristic dark stain and unstained boundary with newborn AR cells born at the base and tip. Most of the L2-d peripheral cells have differentiated as somatic cells and undergone a periclinal division to generate SPL and EN initials (white arrowheads mark recent divisions), and some of the EN initials have divided anticlinally to add length (green arrows).

AR specification is a dynamic process that initiates centrally and proceeds towards the base and tip, ending by ~220 µm (FIG. 1H and FIG. 7). Also commencing centrally, periclinal divisions generating SPL and EN begin in L2-d neighbors at ~180 µm, with a biased start in the locule arch, and are completed by ~275 µm (FIG. 1G). The combination of oriented cell divisions and expansion creates columnar organization over time, converting the locule from a field of globular progenitors into a dartboard anatomy in transverse view with four coherent rings surrounding the central AR column.

Figure 10:
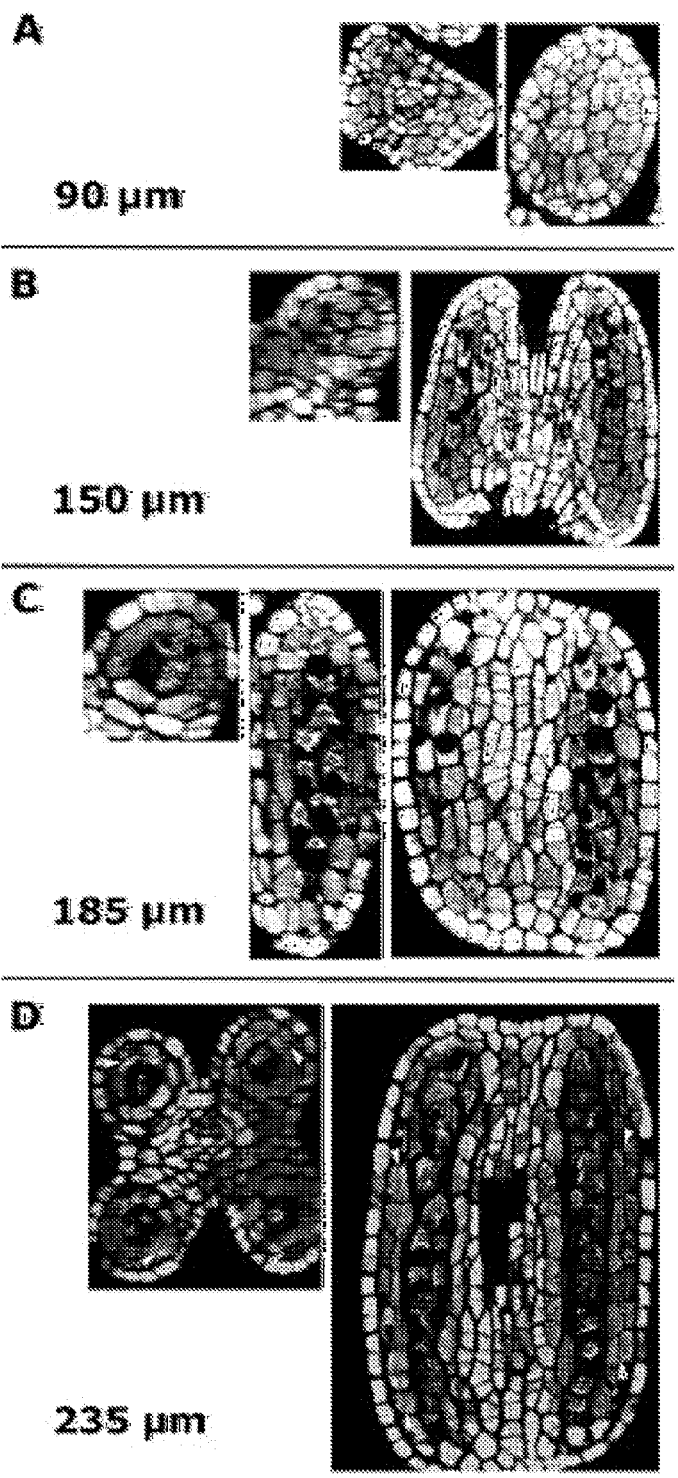
FIG. 10. AR specification in A619 fertile anthers, which generate two AR columns in each locule. (A) 90 µm anther. Left, transverse reconstruction of the anther. Two or three L2-d cells (white dots) can be seen in each corner where the locules are budding. Right, longitudinal image with subepidermal L2-d cells visible towards the right side of the image. (B) 150 µm anther. Left, transverse reconstruction. Two AR cells are visible encircled by a single cell layer wide ring of presumptive somatic cells. Right, 1-2 columns of AR cells, encased in somatic support tissue with presumptive AR cells being born at the base and tip. (C) 185 µm anther. Left, transverse reconstruction, with two AR cells visible inside the somatic ring. Center, longitudinal reconstruction with two columns of AR cells centrally and one presumptive AR near the tip and one near the base. Right, two new AR are observed by the tip in this longitudinal image, along with two nearly full columns of differentiated AR. (D) 235 µm anther. Left, transverse reconstruction with somatic bilayer formation on the arch and 1 or 2 AR cells visible in the center of each of the four locules. Right, longitudinal image showing full AR columns and somatic bilayer formation.

For comparison, morphometric analysis was performed on inbred A619, which has a slower flowering progression and fewer flowers than W23. Despite these differences, the developmental stages were identical. As in W23, AR specification lasted from 120 to 220 µm with morphological differentiation apparent at 160 µm. Notably, A619 locules averaged twice as many AR cells as W23 (FIG. 1H; FIG. 8; FIG. 10).

Example 2

AR Cells Direct Somatic Differentiation Via MAC1

Figure 11:
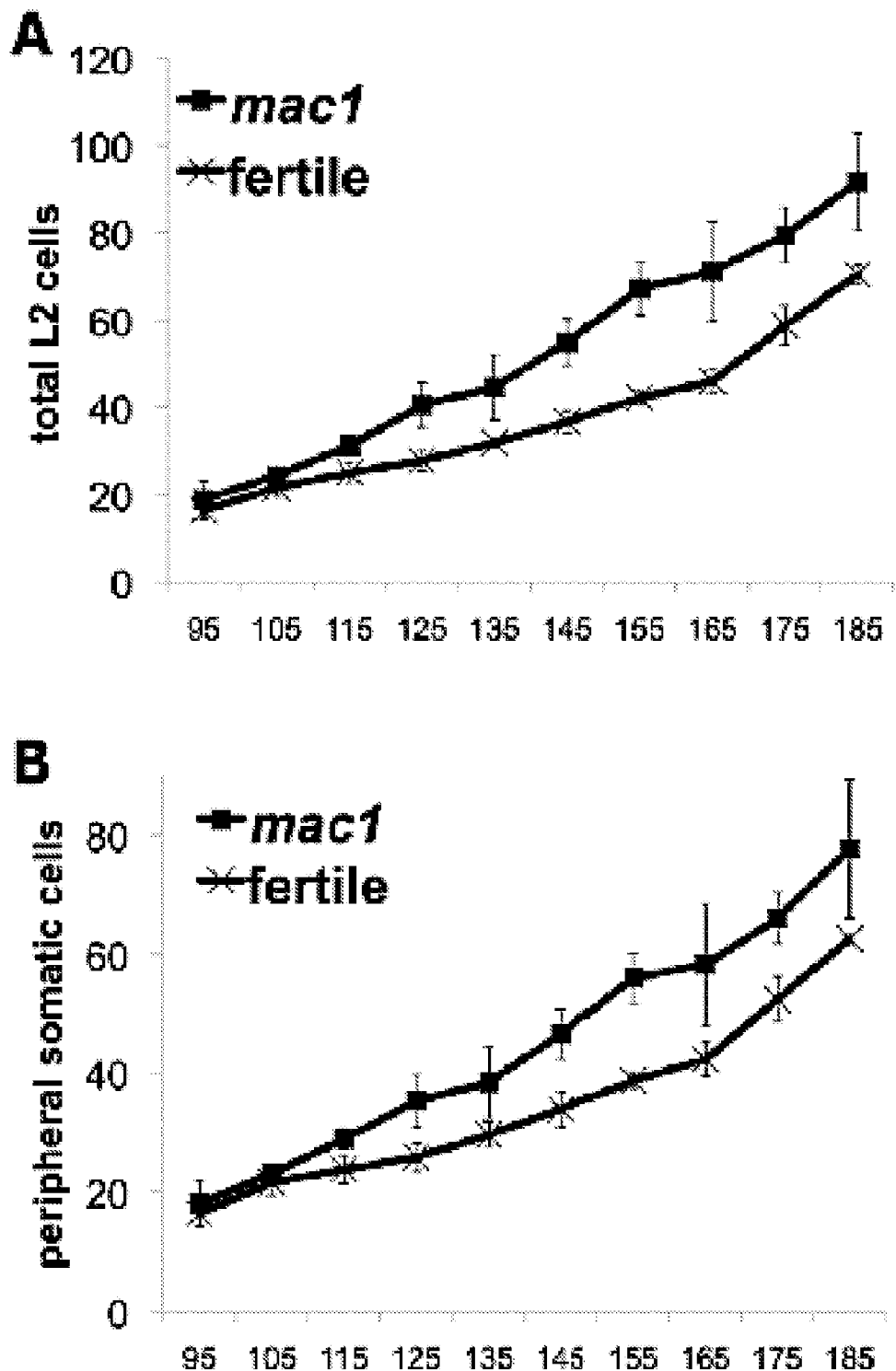
FIG. 11. Male sterile mac1 and fertile sib cell counts, per locule. Each point represents the average counts of at least 16 locules+/−SD. (A) mac1 has supernumerary L2-d cells in the smallest anthers imaged, and the gap between sterile and fertile widens until 165 when it begins to close. Excess cells are located peripherally (B) as well as centrally (C). (B) As the somatic bilayer forms in fertile anthers (>180 μm) the difference in cell number decreases, and fertile overtakes mac1 in somatic count by ~230 μm (not shown). The increased cell count in fertile results from the periclinal division of the peripheral L2-d cells to form EN and SPL while mac1 locules continue to contain only a single L2-d layer. (C) Central AR cells are found in smaller anthers in mac1 than in fertile (including in some 95 μm anthers). This is a consequence of excess L2 progenitor proliferation (these cells are also smaller than in fertile (data not shown), resulting in more cells positioned internally surrounded completely by L2 neighbors. (D) Furthermore, more additional AR births occur in mac1 than in equivalently sized fertile anthers in 125-185 μm locules. Many of the extra AR-generative divisions are periclinal divisions in the ring surrounding differentiated AR, a case rarely found in fertile anthers. (E) The ratio of AR:total L2 is indicative of excessive proliferation (given the circular architecture of the tissue in cross-section, additional cells must be located in the middle, becoming a higher fraction of the total cells in mac1 than in fertile). (F) mac1 AR cells are mitotic at early stages, a trait observed only rarely in fertile locules.
Figure 11:
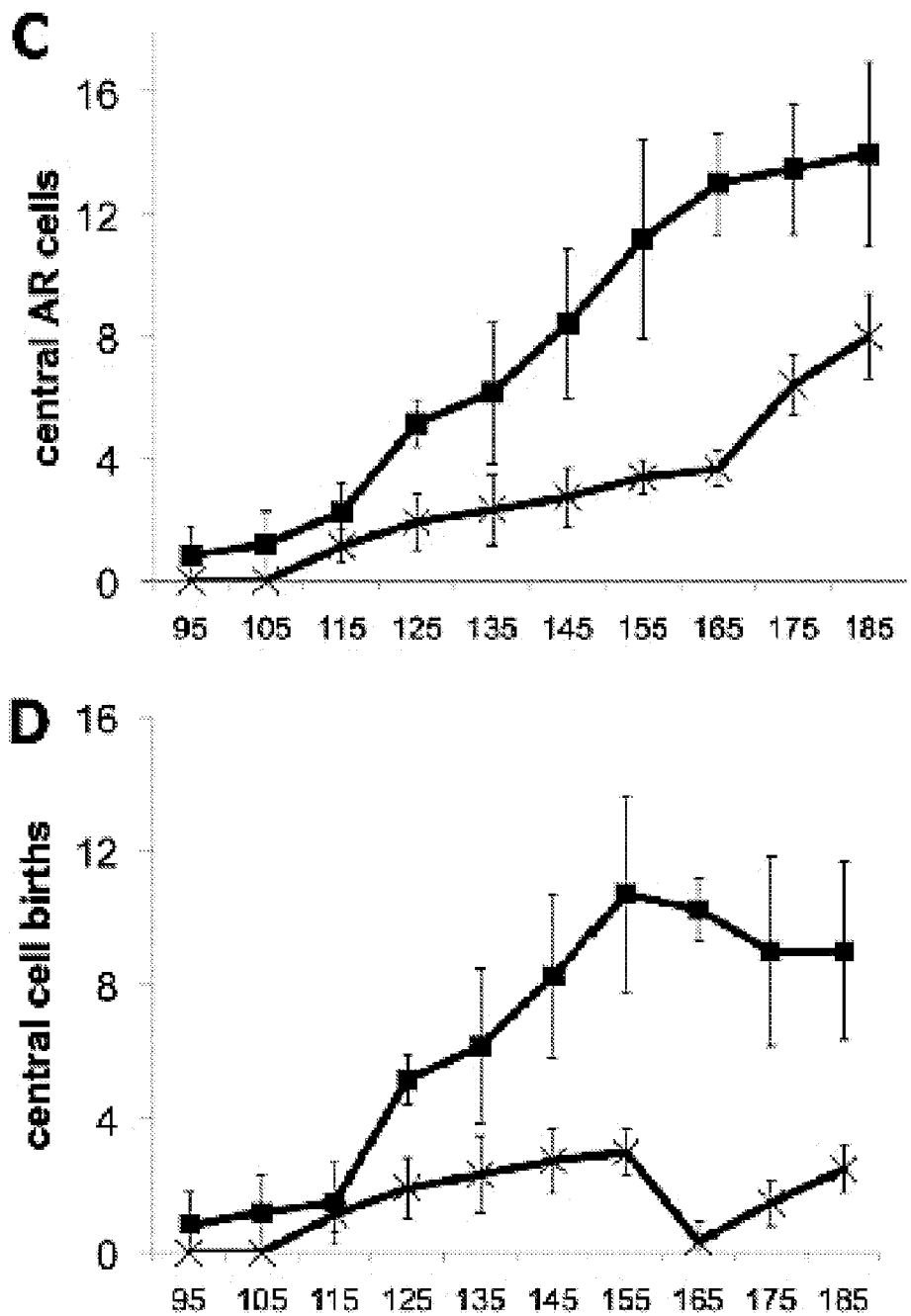

At 300 µm multiple archesporial cells1 (mac1) locules contain only a single somatic layer surrounding excess AR (19). The mutant was introgressed into W23 and compared to fertile siblings. From the onset (<120 µm) and subsequently, locules had extra L2-d cells (FIG. 11A). More L2-d resulted in more cells centrally positioned at an earlier stage than fertile (FIG. 1G). Additionally, supernumerary AR are born because peripheral L2-d cells continue to generate new AR even after an AR column is present, including long after the normal cessation at 220 m, contributing to a growing gap in mac1 and fertile AR counts (FIG. 1I and FIG. 11C). No somatic bilayer is formed. These morphological data define two roles for MAC1: (1) limiting proliferation of progenitor cells and (2) causing the periclinal division necessary to establish the SPL and EN layers.

Two *Arabidopsis* mutants are similar to mac1: the LRR receptor kinase EXS/EMS1 and its putative secreted ligand TPD1, a homolog of rice OsTDL1A. These molecules are proposed to define a signaling module responsible for tapetal specification. Alternatively mutants in this module may suffer from a failure to thrive syndrome of TA initials because unlike mac1, tpd1 and ems1 mutants typically form EN and SPL but ML and TA specification is faulty, except in the C24 background exs phenocopies mac1. MAC1 contains a predicted cleavable signal peptide.

Figure 12:
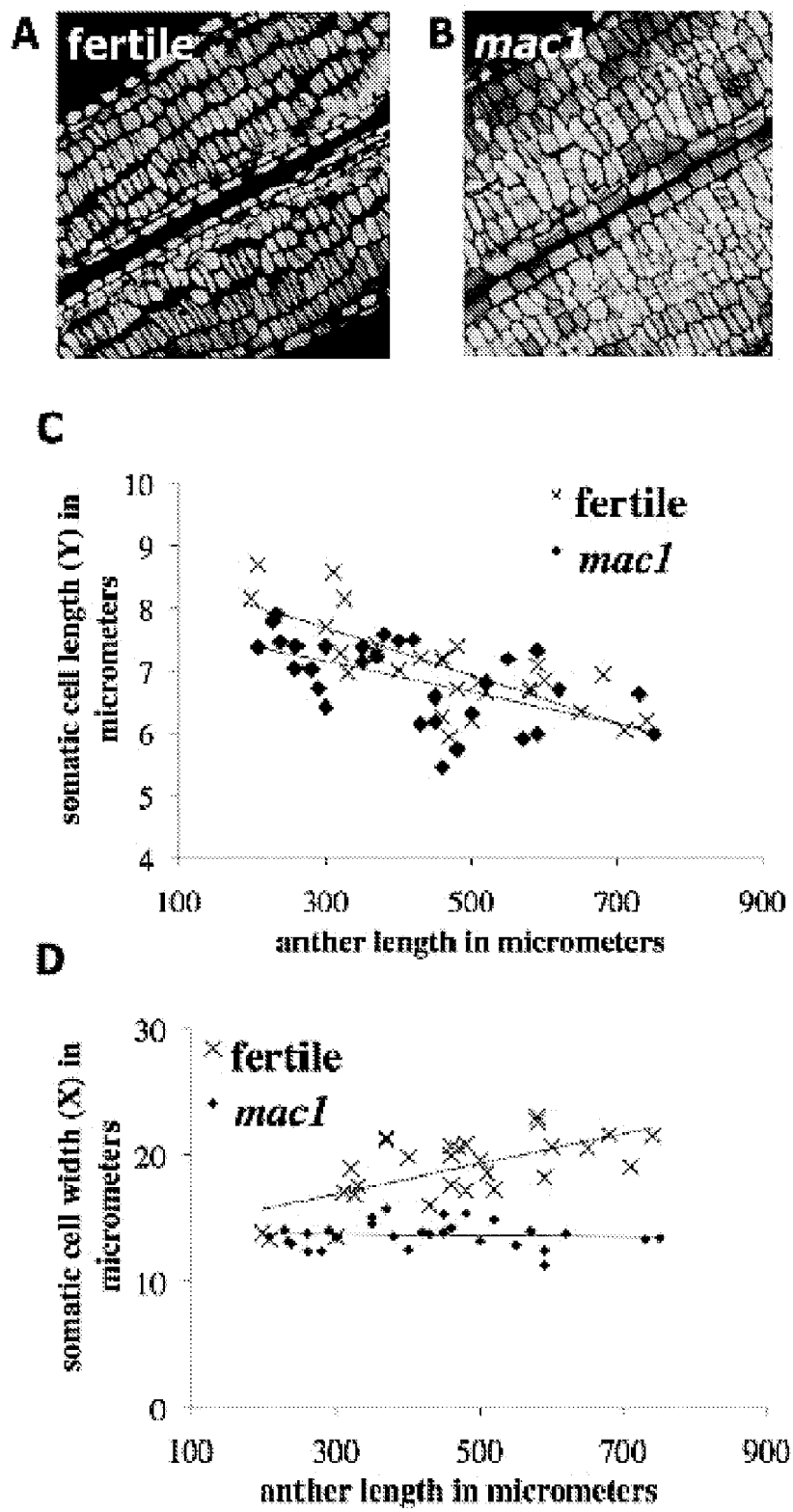
FIG. 12. MAC1 controls division orientation, not division rate, in somatic tissues. Fertile EN illustrating normal cell numbers (A) and mac1 subepidermal (B) layers containing excessive cells. (C,D) Each point represents the average of least 50 cells in a single locule. (C) EN/subepidermal cell length (distance along longitudinal (Y) axis) is equivalent. (D) Somatic cell width (circumferential (X) axis) is smaller in mac1, as a result of excessive anticlinal divisions. The endothecial layer in fertile has ~12-14 very wide cells around the locule at reproductive maturity (Kelliher and Walbot 2011). In mac1 ~20-25 somatic cells occupy this circumference. Eventually, a partial second layer forms in mac1 around 700 five days late, but it bears no resemblance to the SPL, ML, or TA. This is similar to aspects of TPD1/EMS1 phenotypes in Arabidopsis, but in those mutants a full SPL is present initially, while in mac1 no SPL is ever formed. Interestingly, the exs mutant in the C24 background has only a single somatic layer as is found in mac1. (E-F) EdU stain in fertile (E) and mac1 (F) anthers showing excessive staining in mac1 AR cells, indicative of a faster mitotic rate. 10 uM EdU was injected into the tassel airspace six hours before dissection of 200-600 μm anthers. Red, propidium iodide; green, EdU. (G-H) Quantification of EdU staining in fertile and mac1 somatic layer(s). Each dot represents a single locule, from which all the cells were counted. EdU staining was even and distributed equivalently along the length of the locule, because anthers lack an intercalary meristem. The bars represent averages of the locules examined +/−SD. (G) Combining the cell counts for the EN and SPL layers together for fertile, the percentage of somatic cells that are EdU positive is slightly greater than in mac1 but the difference is not significant. (H) The percentage of EdU+AR cells was significantly greater in mac1 than in fertile.
Figure 12:
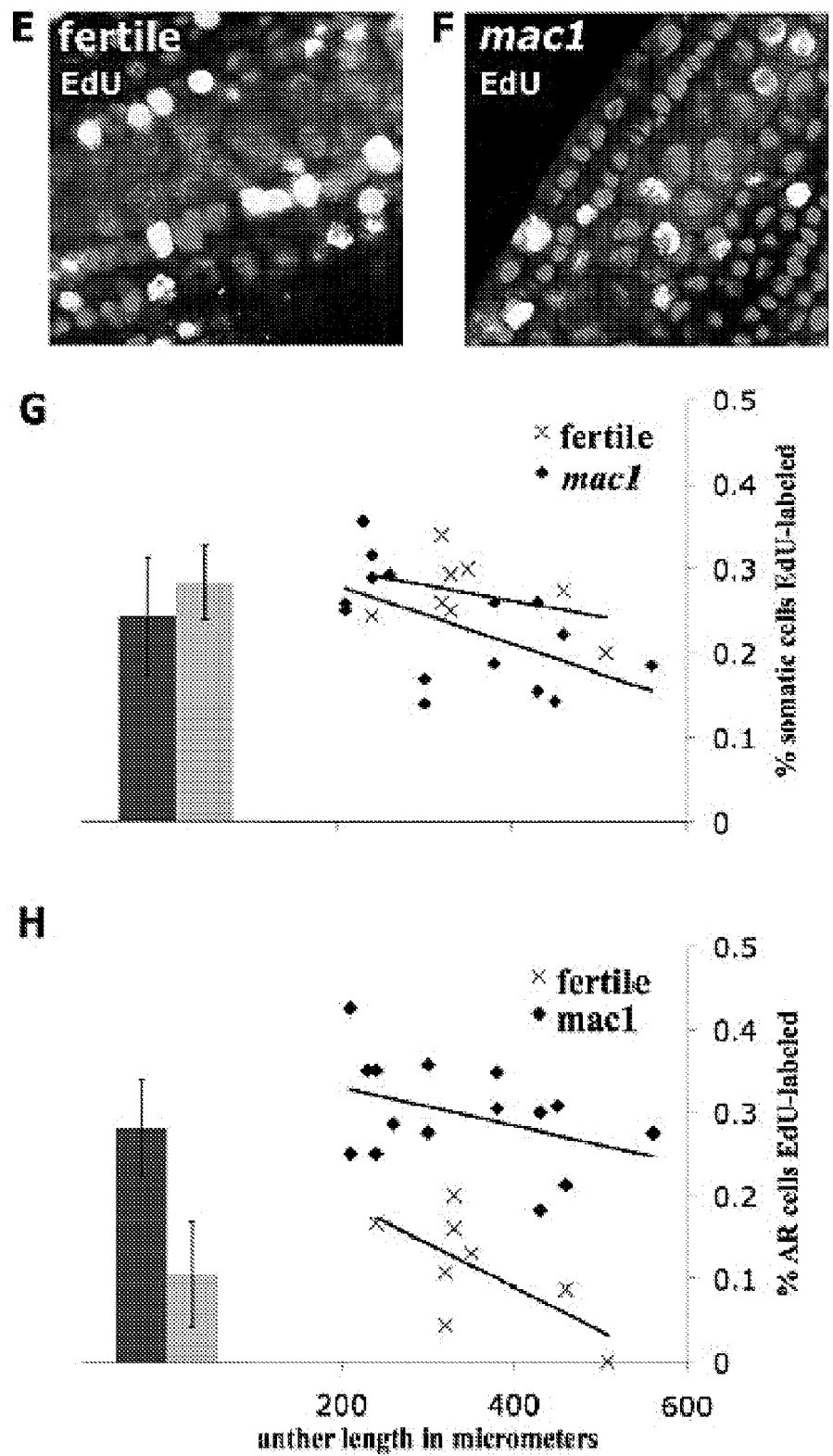

The single layer mac1 soma has a cell census similar to the sum of EN and SPL in fertile siblings; mac1 somatic cells are smaller than either SPL or EN reflecting increased anticlinal division to sustain anther elongation (FIG. 12A-D). 10 µM EdU was injected into tassels during the phenocritical period, and 6 hours later anthers were stained (FIGS. 12, E and F). The frequency of EdU+ somatic cells was slightly but not significantly less in mac1 than fertile (FIG. 12G). Therefore, MAC1 does not influence somatic proliferation rate per se, but rather directs the singular periclinal division of L2-d neighbors.

AR proliferation dramatically increased: 30% of mac1 AR cells were EdU+ compared to 12% in fertile (FIG. 12H). Despite excess proliferation and absence of normal soma, transcriptome profiling demonstrates normal gene expression in preparation for meiosis. Of the 297 genes identified as AR-enriched in fertile anthers, 96.7% had parallel expression in laser microdissected AR from mac1 compared to fertile siblings (Table 1). Mirroring fertile PMC, mac1 PMC start meiosis, but arrest in Prophase 1.

Mac1 expression is low in tassel and anther primordia; there is a burst of expression in ~150 µm anthers, when the first AR cells morphologically differentiate with increases at subsequent stages. Mac1 is also significantly enriched in laser-microdissected AR cells at both the 300 µm and 700 µm stages compared to the EN, SPL, ML, and TA layers (FIG. 1J). We conclude that MAC1 limits proliferation of pluripotent progenitor cells and mitotic AR cells; AR cells preferentially express Mac1 to direct differentiation of surrounding pluripotent L2-d into the multipotent somatic pathway (represented by arrows, FIG. 1E), directing periclinal divisions orthogonal to the MAC1 signal source. The normal maturation of mac1 AR cells indicates independence from somatic tissues during progression from AR specification, mitotic proliferation, transition to PMC, and meiotic entry. Furthermore, csmd1 defective in the soma completes meiosis. Germinal independence contrasts with animal spermatogenesis, where meiotic entry depends upon a functional somatic niche.

Example 3 msca1 Blocks AR Differentiation

Figure 13:
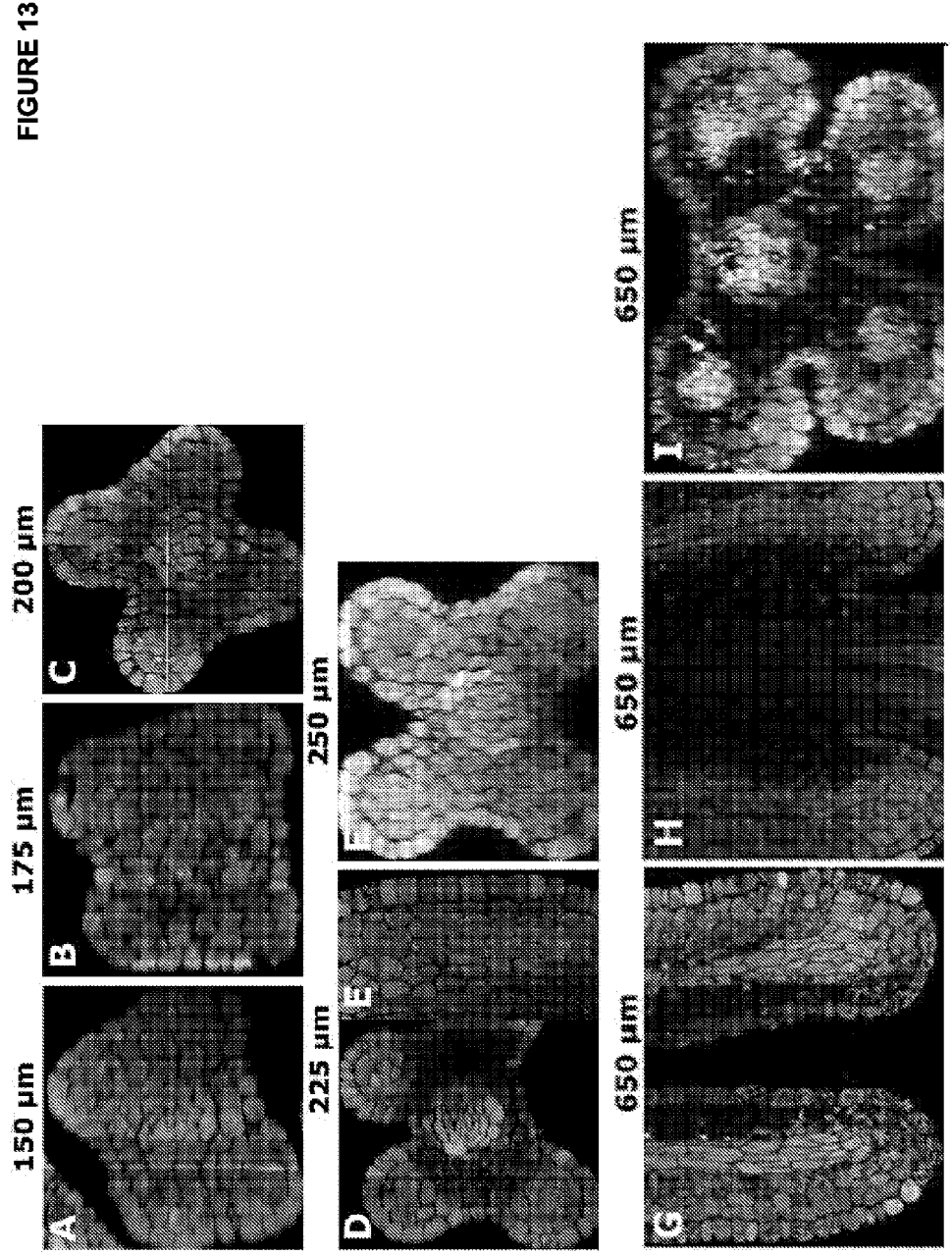
FIG. 13. Sterile msca1 anthers have none of the normal locule cell types. Initially, anthers appear normal (A,B), but central cells never differentiate as AR (C-F). They instead continue to proliferate and create long, columnar cells that differentiate as vascular bundles (E,G,I). These bundles do not connect with the central vasculature of the stamen, but instead terminate at the tips and base into a mass of parenchyma-like cells (H).
Figure 14:
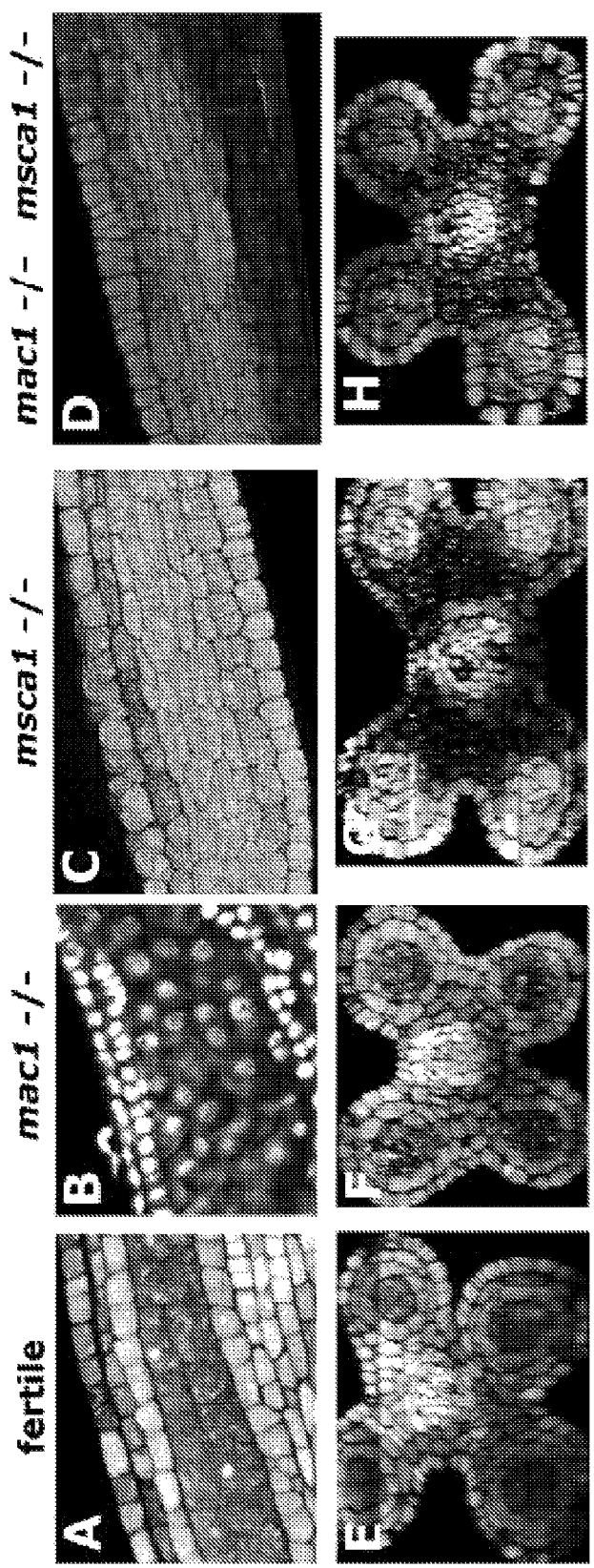
FIG. 14. Fertile, mac1, msca1, and mac1 msca1 double mutant anthers in longitudinal images and transverse reconstructions at the four cell layer stage. (A-D) Longitudinal images of single locules. (E-H) Transverse Z-stack reconstructions of the butterfly cross-section. (A,E) Fertile anther at 400 μm with EPI, EN, SPL, and AR cell layers and central CT and VT. (B,F) mac1 anther with EPI, a faulty somatic layer with occasional periclinal division resulting in a one cell wide bilayer, and excess AR. The longitudinal image is from a 600 μm anther while the transverse is from a 280 μm anther. (C,G) msca1 anthers lack all normal internal cell types and instead locules contain vascular bundles and parenchyma-like cells. (D,H) The double mutant looks just like msca1.

Anatomically normal msca1 anthers contain none of the correct cell types. During locule budding msca1 anthers are identical to fertile, however, globular progenitor cells surrounded by L2-d continue to proliferate then differentiate as columnar vasculature (FIG. 13). Vascular bundles were also observed in mac1 msca1 (FIG. 14). Mac1 transcript was barely detectable in 200 μm msca1 anthers confirming that increased expression is an AR cell attribute (FIG. 1J). MSCA1 is a glutaredoxin, a redox regulator that reduces disulfide bridges, and belongs to a plant-specific Glade that regulates transcription factor activity.

Example 4

The Tassel Airspace is Hypoxic During Cell Fate Setting

Reactive oxygen species (ROS) affect many plant developmental processes, including root hair elongation, leaf growth, and root transition zone placement. During AR specification, the tassel is tightly encased within a whorl of not yet photosynthetic leaves. As a sink tissue undergoing rapid growth, the tassel and surrounding leaves have high metabolic demand, and we reasoned oxygen could be depleted in the small air space (~1 cm$^3$) between the tassel and innermost leaf. To determine oxygen concentration, we inserted a needle-borne probe at several developmental stages (FIG. 15A). After measuring percent $O_2$, plants were opened to confirm needle position in the airspace and measure anther size. During AR specification, the airspace was hypoxic at 1.2-1.4% $O_2$ (N=5). Measurements at 12 cm increments above the tassel were 4%, 8%, 16% and finally 20% $O_2$ near the top. Thus, there is an oxygen gradient in the whorl, with a hypoxic atmosphere surrounding the tassel. This condition is transient, because there is >5% $O_2$ around 10 cm tassels 5 days after AR specification.

Example 5

Figure 15:
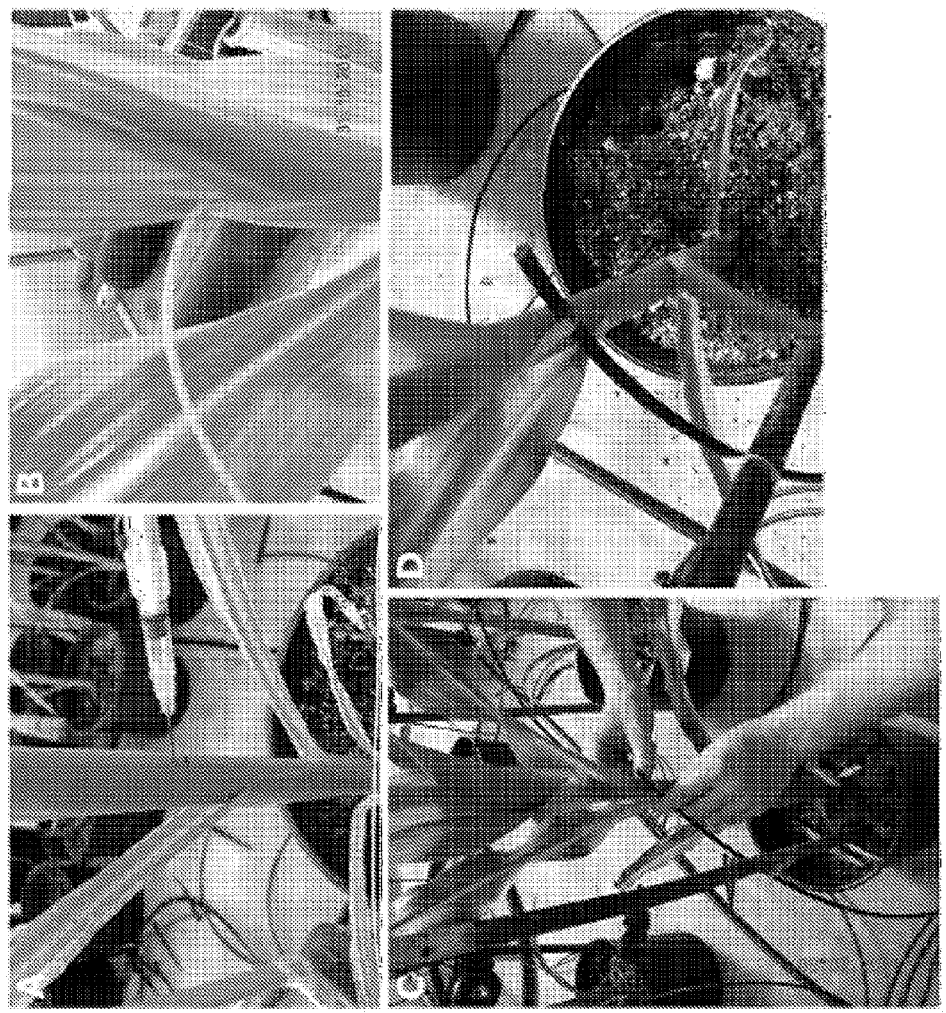
FIG. 15. Photographs of oxygen measurement and manipulation protocols. (A) Oxygen probe set up with needle inserted through the leaf whorl at the level of the tassel and positioned within the internal airspace. (B) Hose threaded down into leaf whorl for $N_2$ or $O_2$ administration. (C,D) Gas delivery through a 26 gauge needle.

Oxygen Manipulation Alters Developmental Pace and Pattern $N_2$ or $O_2$ gas was administered through hoses threaded into the leaf whorl (FIG. 15B). The $O_2$ probe responded within 2 min, dropping to 0% with nitrogen and exceeding 30% with oxygen (maximal probe capacity). Alternatively, nitrogen, oxygen, or compressed air (20% $O_2$) were administered by connecting gas lines to a needle inserted into the tassel airspace (FIGS. 15, C and D). In all experiments, a low flow of gas was administered over a 24 (A619) or 48 hour period (W23). Total locule cells (FIGS. 2, B, H, and M), peripheral somatic cells (FIGS. 2, C, I, and N), and central AR cells (FIGS. 2, D, J, and O) were quantified.

Figure 16:
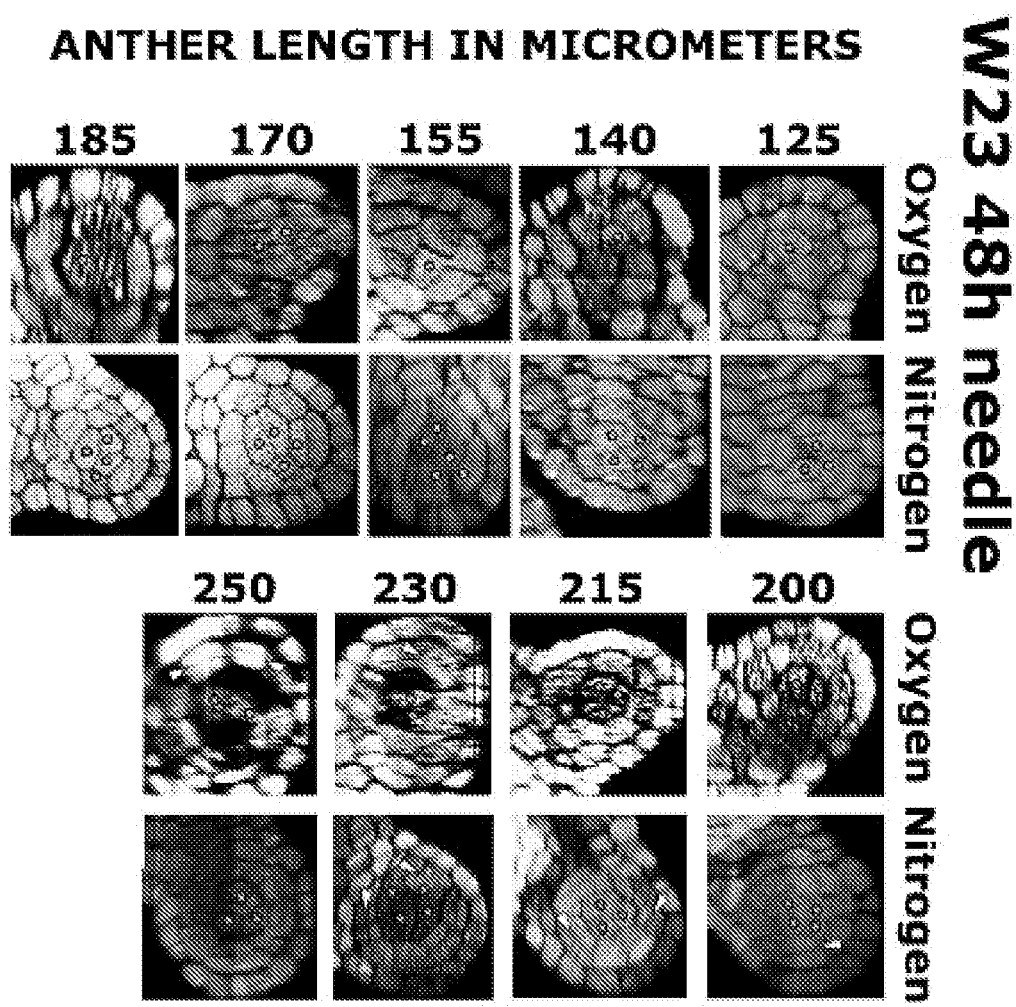
FIG. 16. Transverse reconstructions of 48 h gas treatments delivered through a needle. Excess presumptive AR cells are present in $N_2$ treated locules starting in the earliest anthers checked (125 μm) and at subsequent stages. The SPL/EN bilayer is also formed early in nitrogen but delayed in oxygen, confirming results from the hose delivery protocol.

Compared to untreated fertile anthers, all three $N_2$ protocols resulted in early specification and excess AR cells, phenocopying the first component of mac1 development (FIGS. 2A, 2D, 2G, 2J, and 2O; FIG. 16). The $N_2$ treatment also increased peripheral somatic cell counts later after 48 hour exposure (FIGS. 2C and 2N). AR:total L2 ratios were calculated (FIGS. 2, E, K, and P). Nitrogen-treated anthers had elevated ratios—up to 25% are central AR at early stages, dropping late due to precocious bilayer formation (FIGS. 2, F, L, and Q).

Figure 2:
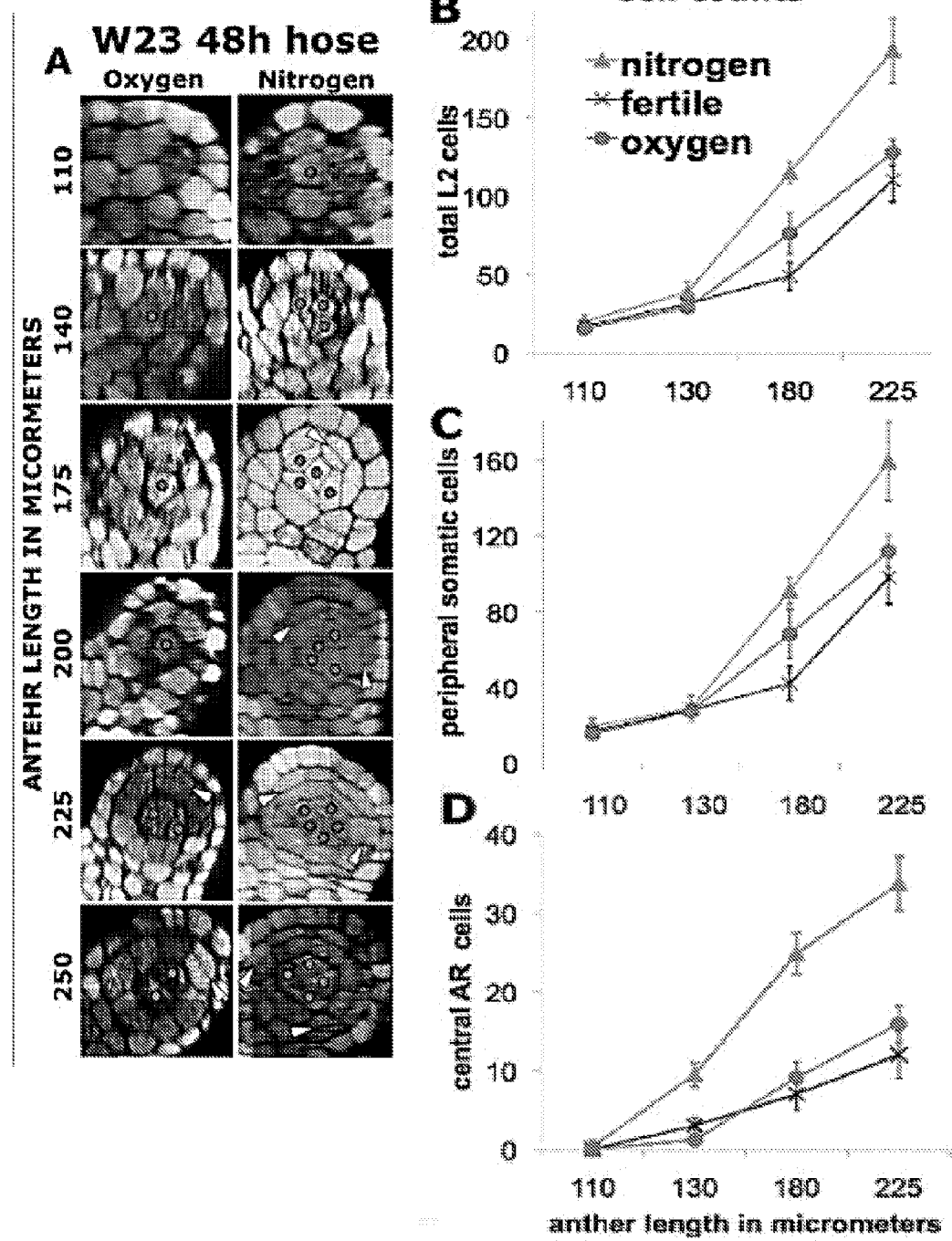
FIG. 2. Oxygen tension manipulation. (A,G) Transverse reconstructions of single locules in gas treatments (dots indicate AR cells; arrowheads indicate somatic divisions). (B,H,M) Total L2 counts. (C,I,N) Peripheral counts. (D,J,O) AR counts. (E,K,P) AR:total L2 ratio. (F,L,Q) Progression of SPL/EN bilayer formation on locule arch.
Figure 2:
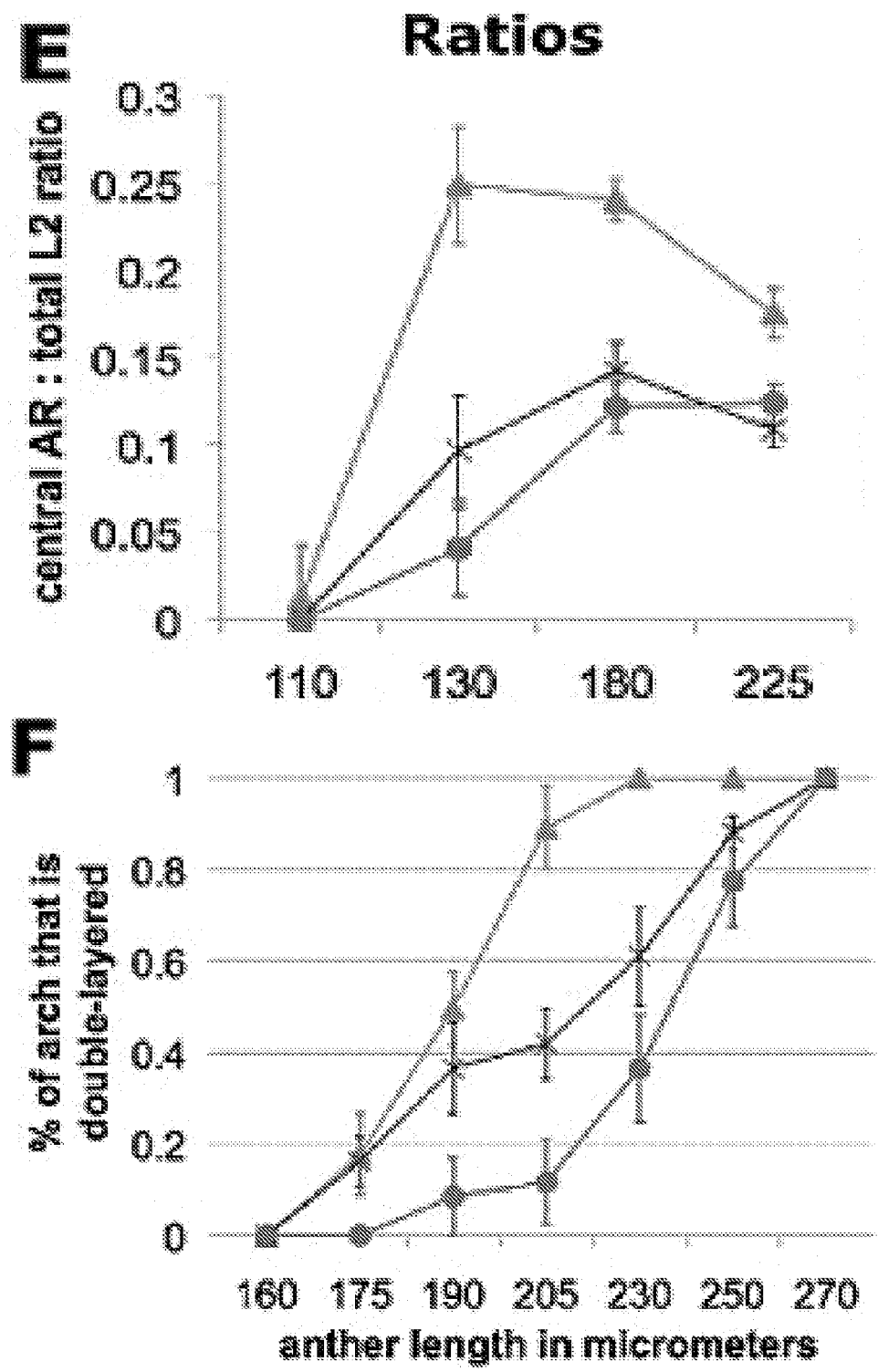
Figure 2:
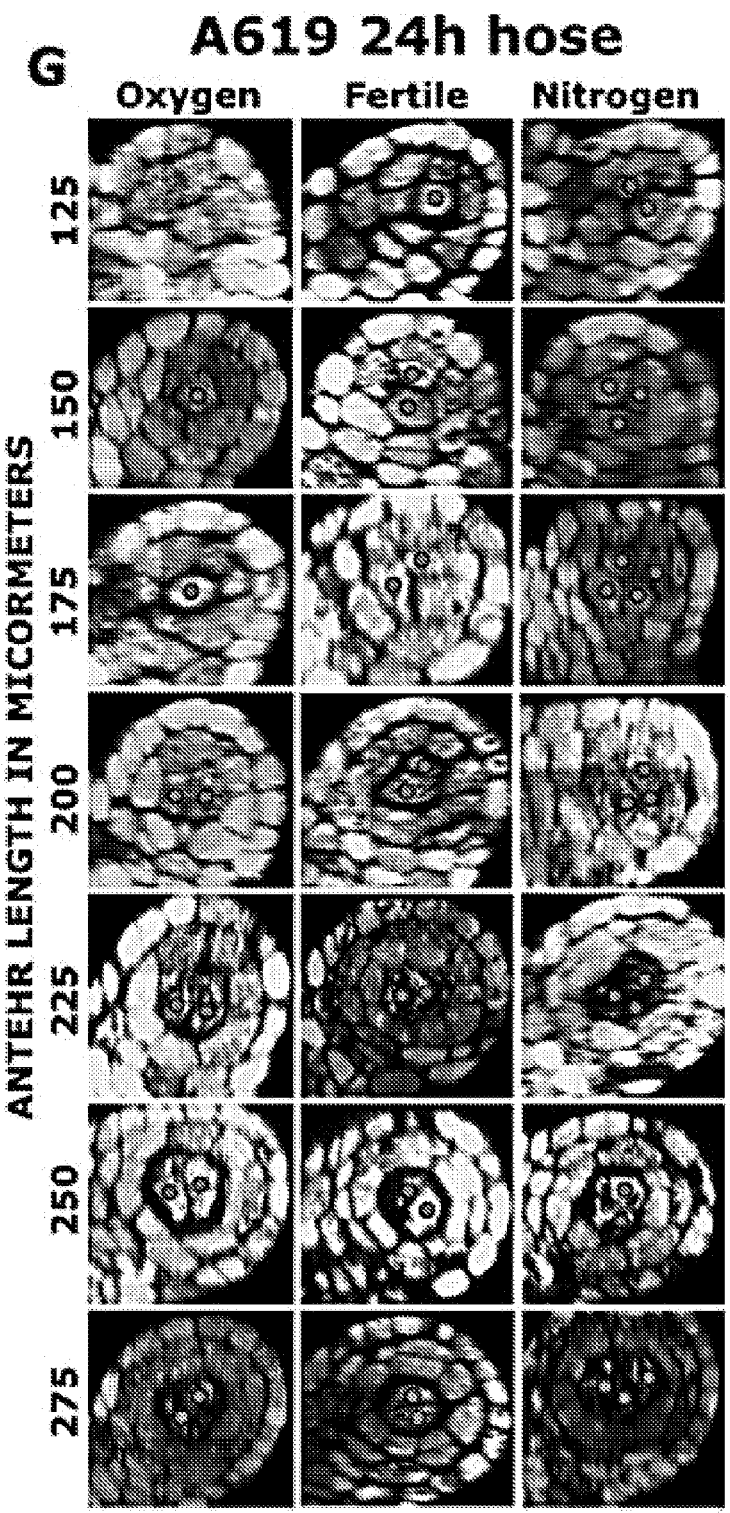
Figure 2:
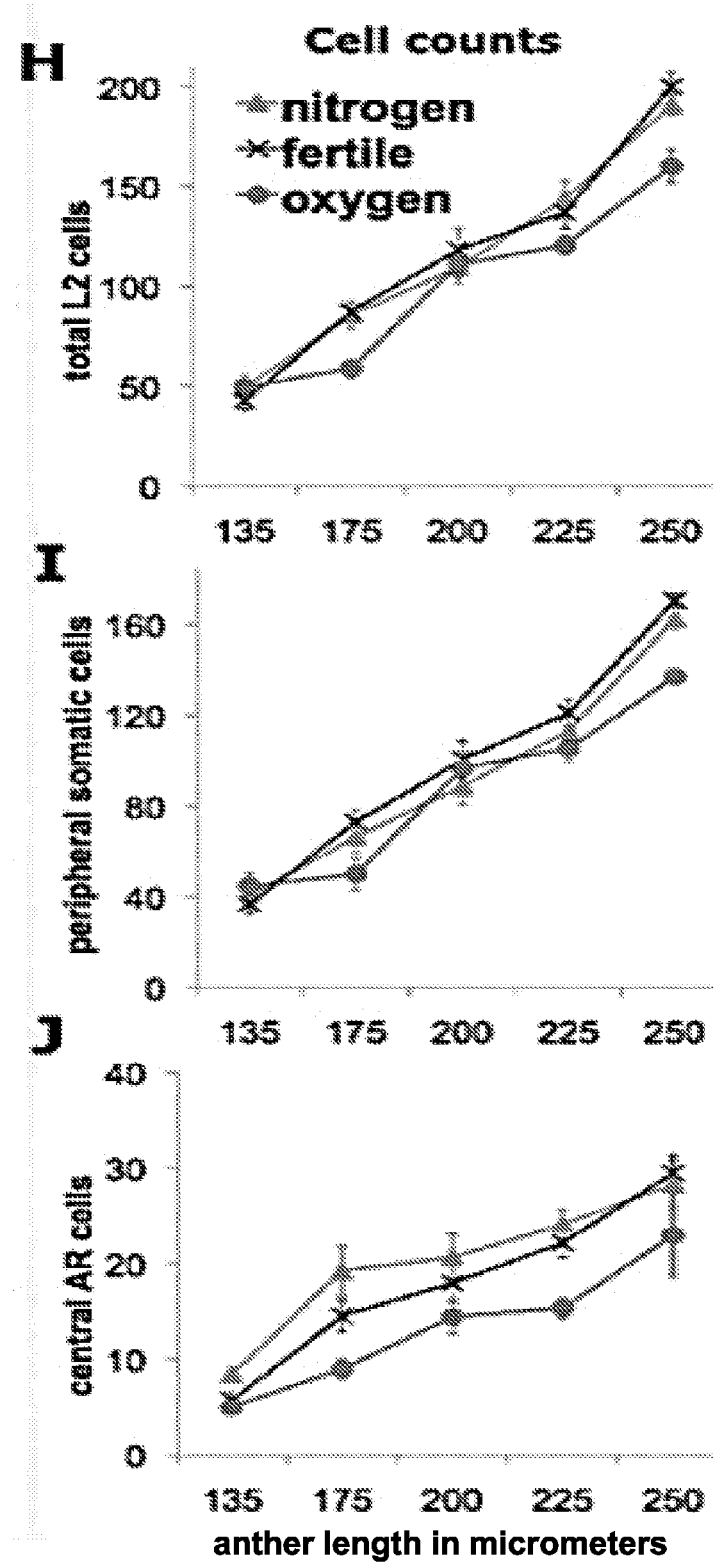
Figure 2:
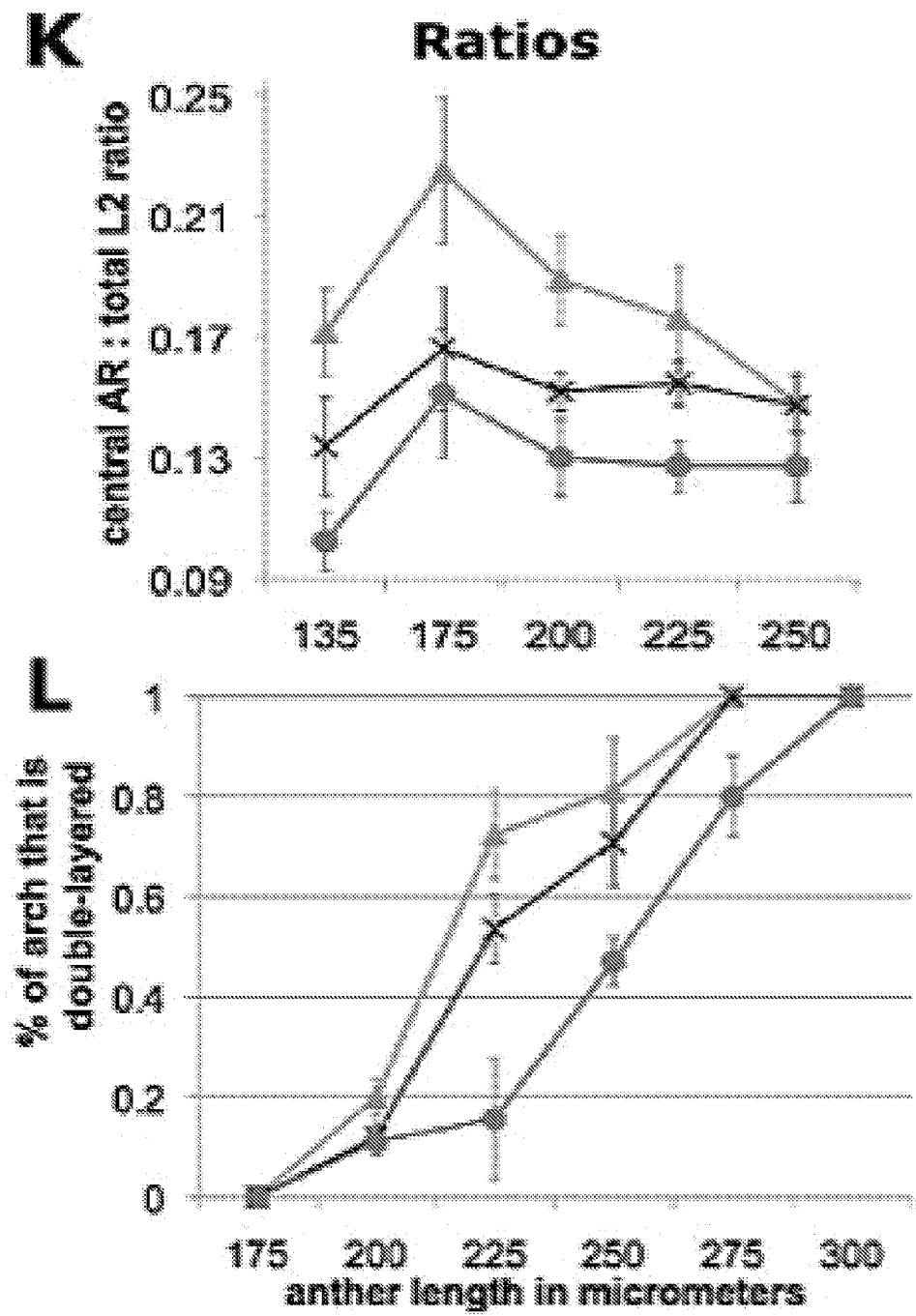
Figure 2:
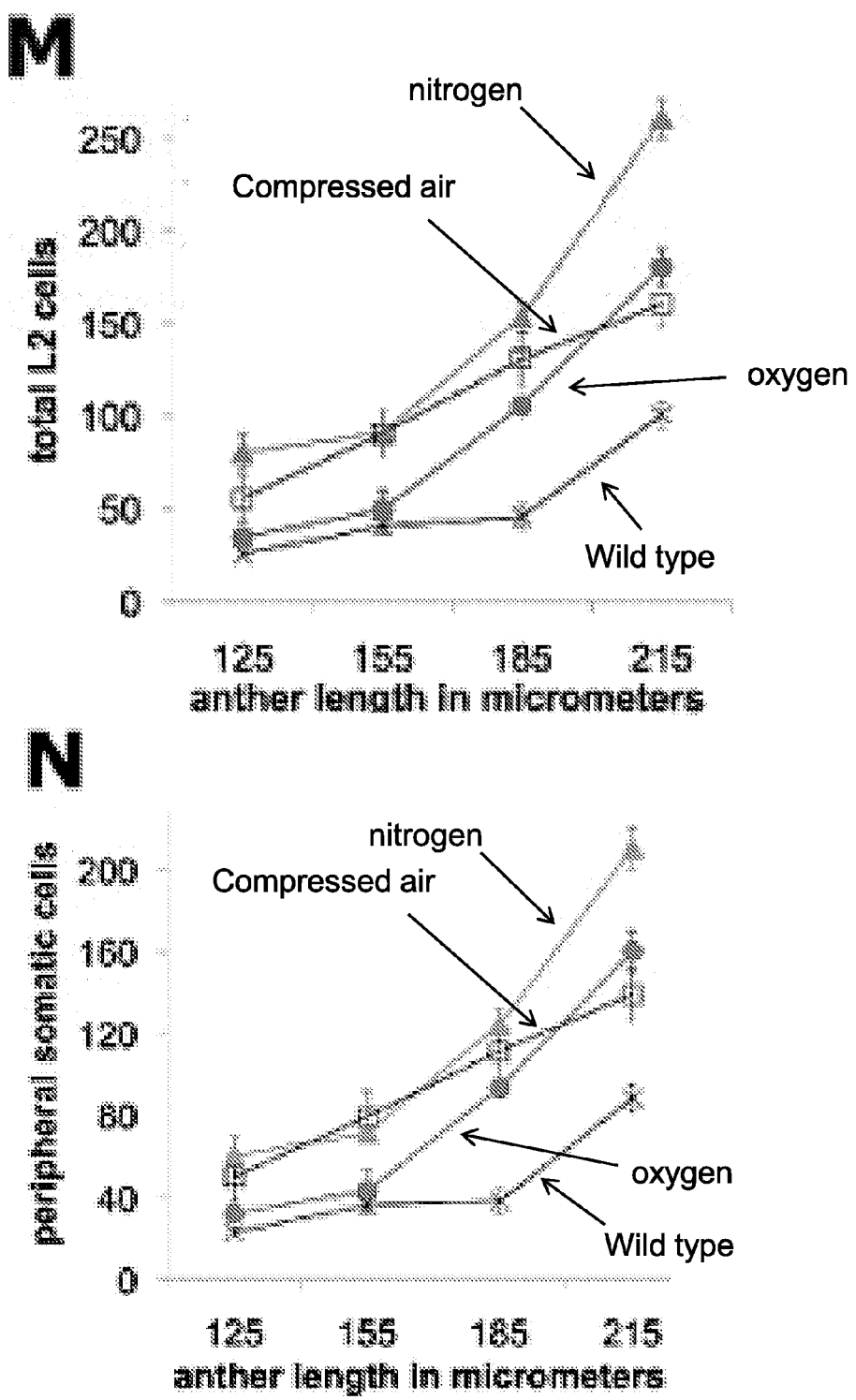
Figure 2:
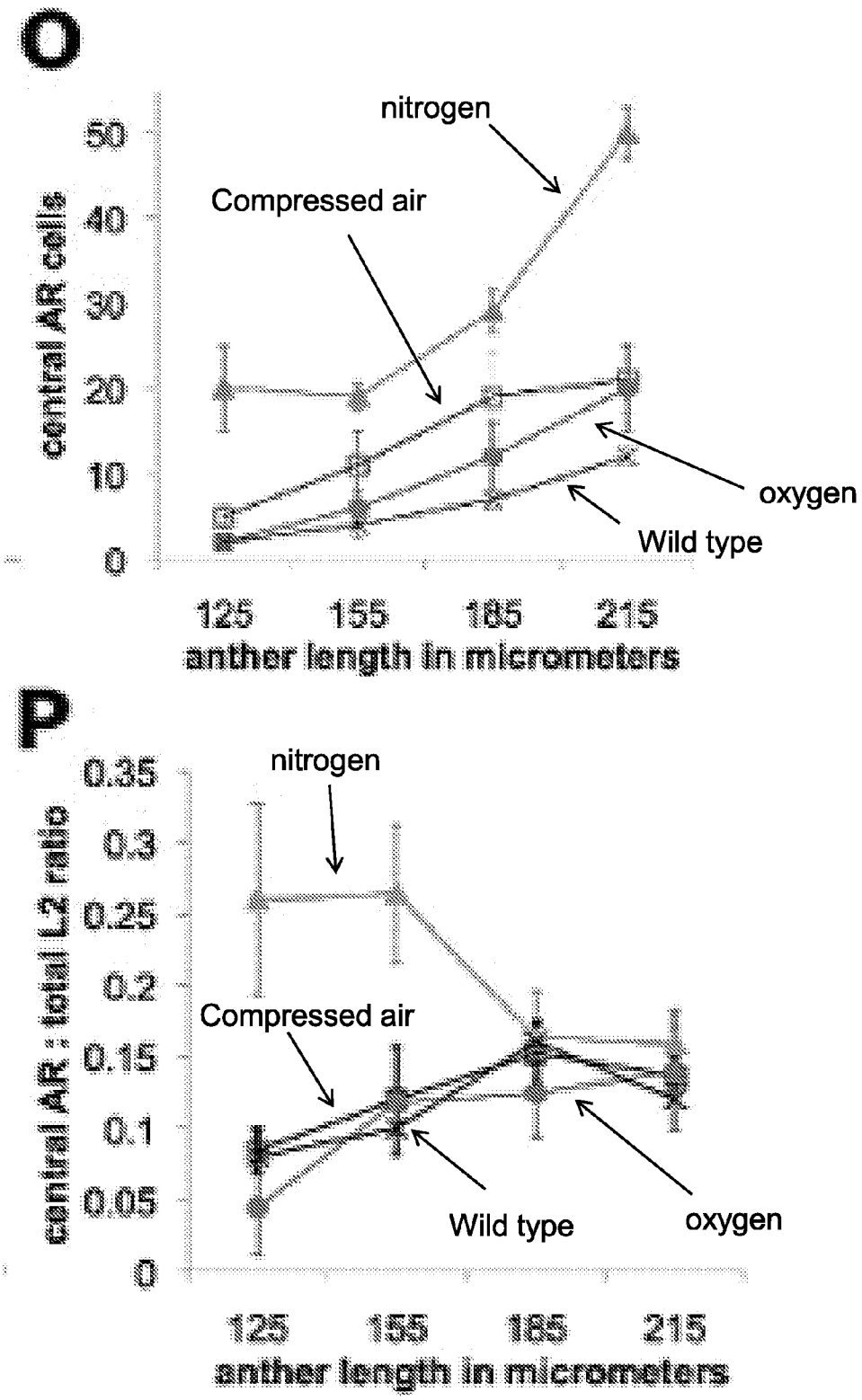
Figure 2:
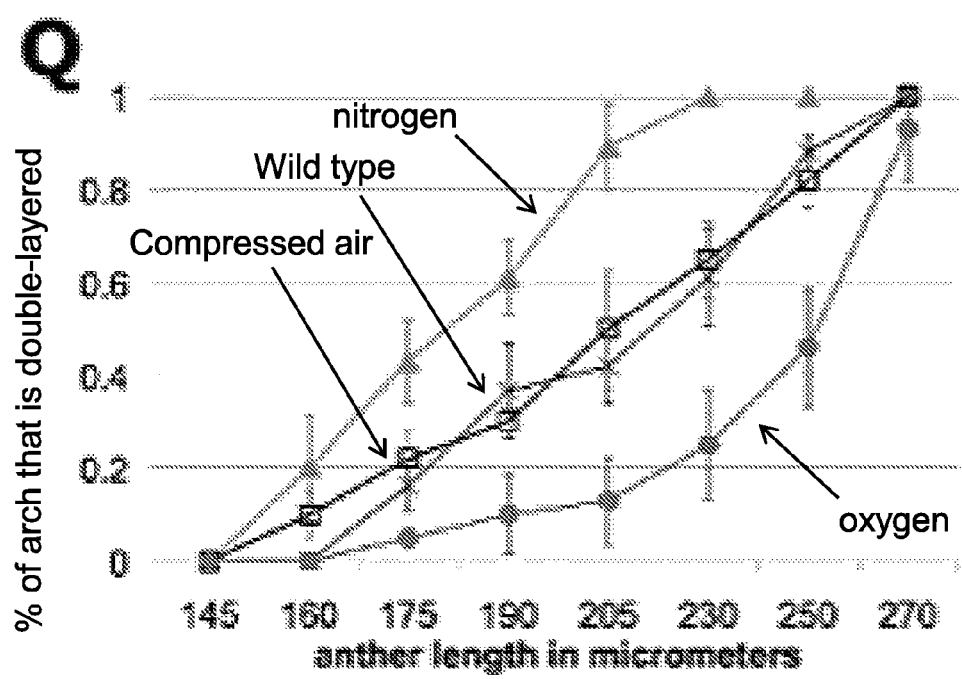

In contrast, the hose $O_2$ treatment repressed AR specification: central AR counts were far lower than $N_2$ after 48 hour treatment (FIGS. 2, A and D); 24 hour exposure caused significantly fewer AR than either untreated or $N_2$ (FIG. 2J). Finally, AR counts were elevated in the needle trial, less than compressed air and dramatically less than nitrogen (FIG. 2O and FIG. 16). Anthers from needle treatments were larger and had excess L2-d cells (FIG. 2N), reflecting increased proliferation throughout the locule caused by wounding (data not shown). The hose treatment also increased peripheral somatic cells in the late stages after 48 (FIG. 2C), but not 24 hours (FIG. 2H). These extra somatic cells resulted from excess anticlinal not periclinal divisions from 175-225 μm (FIG. 2A); somatic niche formation was delayed (FIGS. 2, F, L, and Q). In summary, hypoxia stimulated proliferation of the progenitors, causing precocious and excess AR specification and rapid somatic development, while excess $O_2$ inhibited both events.

Figure 3:
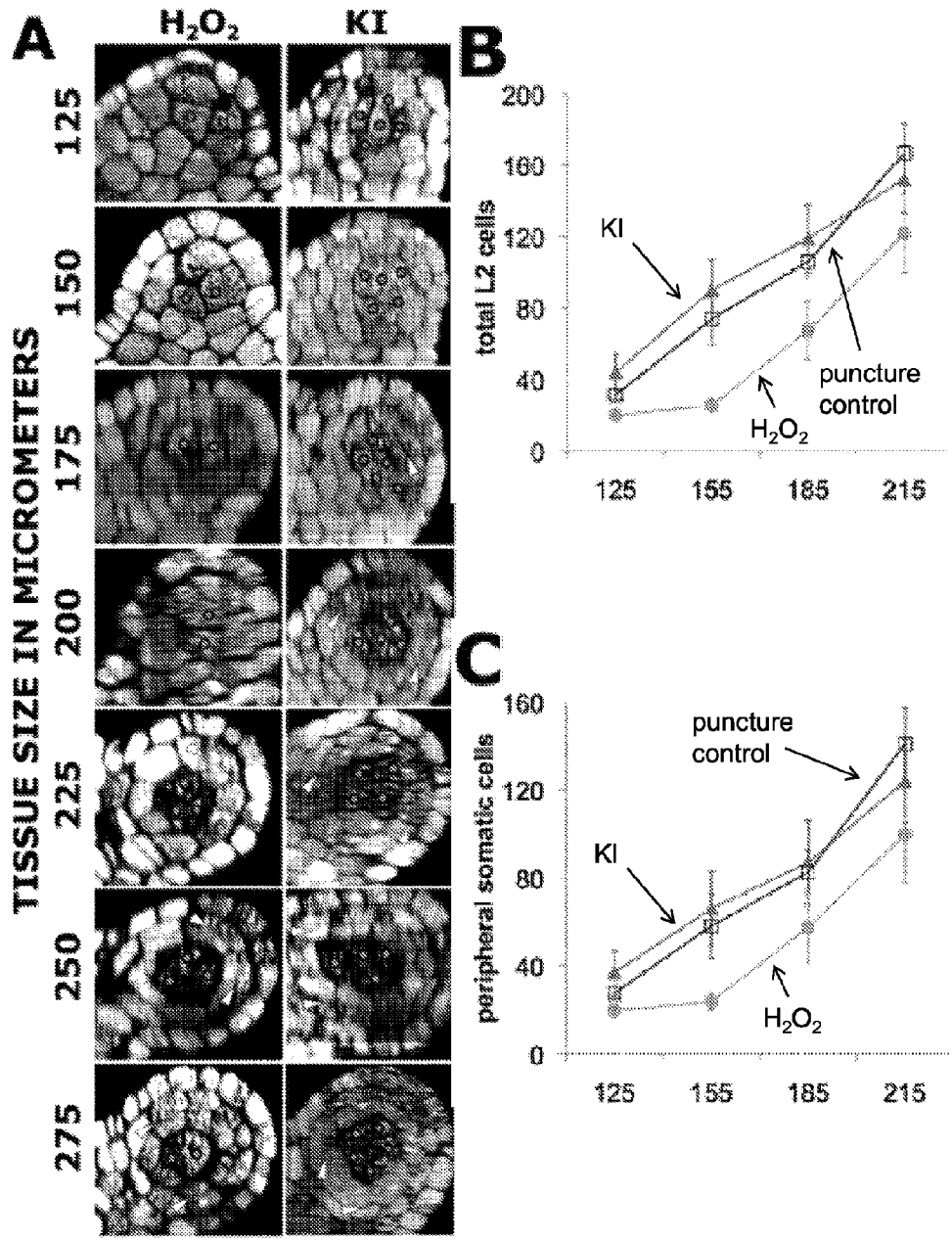
FIG. 3. ROS manipulation. (A) Transverse reconstructions of single locules in treatments (dots indicate AR cells; arrowheads indicate somatic divisions). (B) Total L2 counts. (C) Peripheral counts. (D) AR counts. (E) AR:total L2 ratio. (F) Progression of SPL/EN bilayer formation on locule arch.
Figure 3:
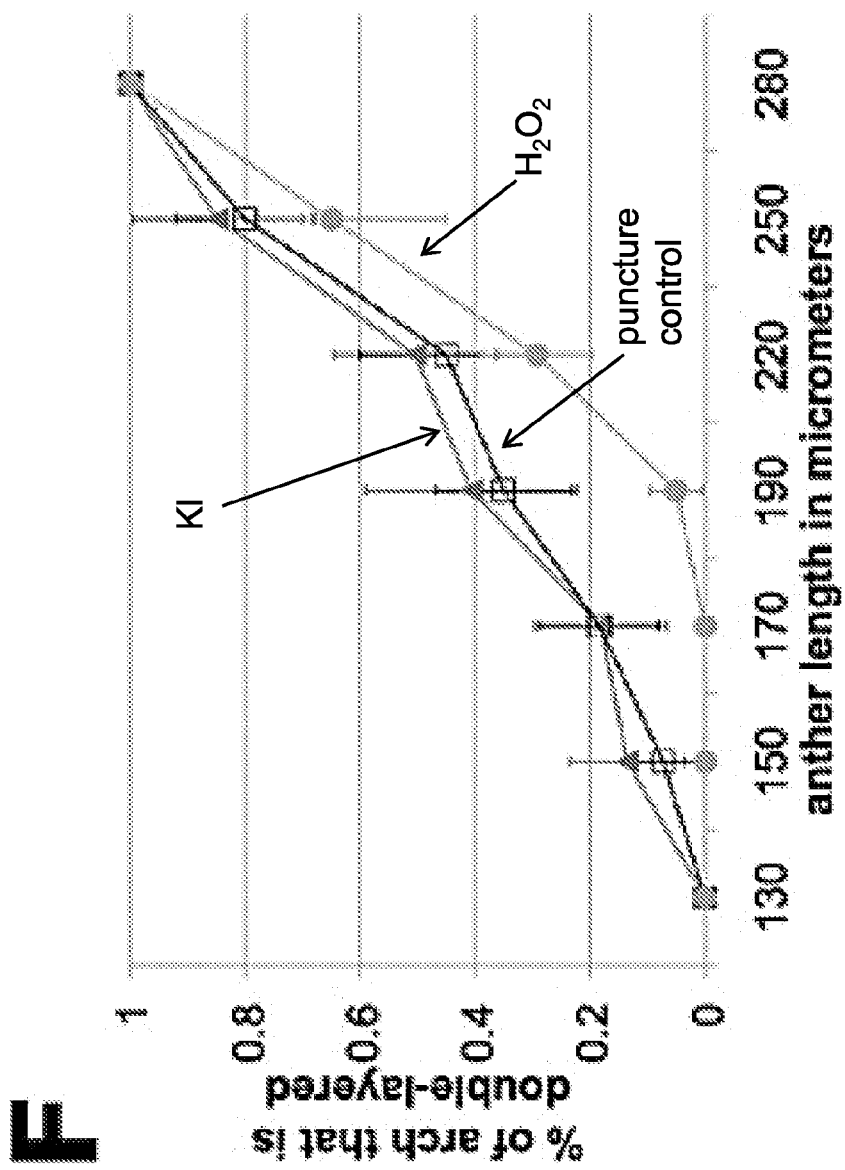
Figure 17:
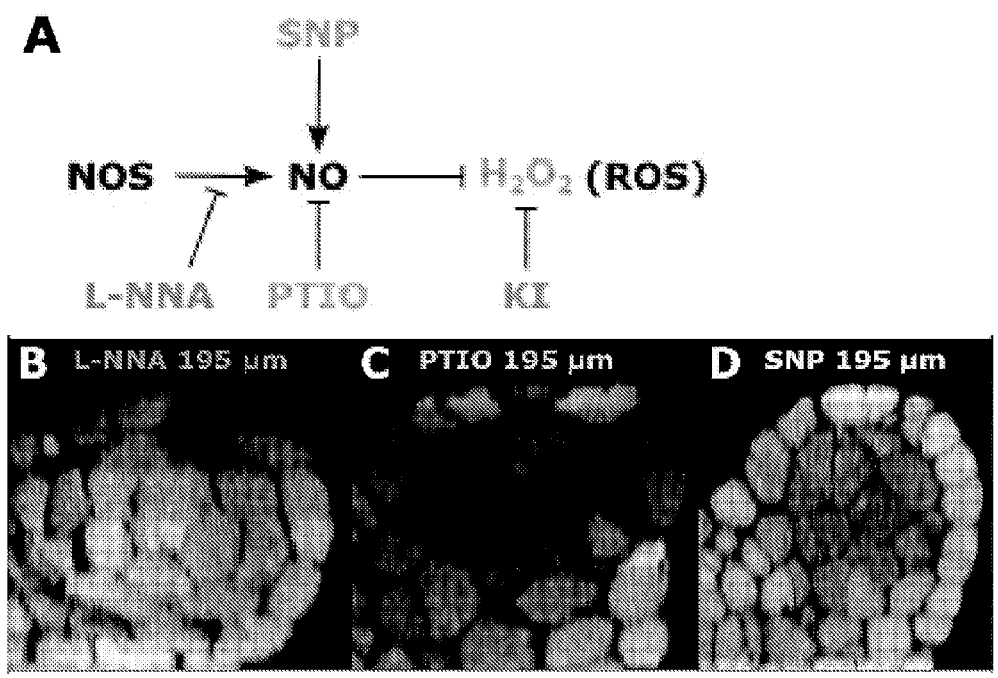
FIG. 17. NO(ROS inhibitor) pushes cells towards an AR fate. (A) $N^G$-nitro-L-Arginine (L-NNA) (NO synthase inhibitor), 2-Phenyl-4,4,5,5-tetramethylimidazoline-1-oxyl-3-oxide (PTIO) (NO scavenger), and sodium nitroprusside (SNP) (NO donor) were injected into the tassel airspace during the critical AR specification period 48 h prior to anther dissection. NO suppresses methyl jasmonate-induced $H_2O_2$ production (32) and reduces $O_2$ consumption (44). (B-D) All three treatments slowed the morphological differentiation of central AR cells. Central cells were present but anthers did not achieve the normal somatic ring/central germinal cell organization until ~250 μm. (E) Central AR counts were slightly repressed in PTIO and L-NNA treatments, and slightly promoted in SNP at all three stages checked. (F) However, the progression of somatic bilayer formation was dramatically delayed in all three treatments compared to the puncture control and untreated plants, with SNP being the most delayed (green). Diphenylene iodonium (DPI) (inhibits NADPH oxidase and other flavin-containing enzymes) was also administered, but this treatment caused complete degeneration of the tassel tissues.
Figure 17:
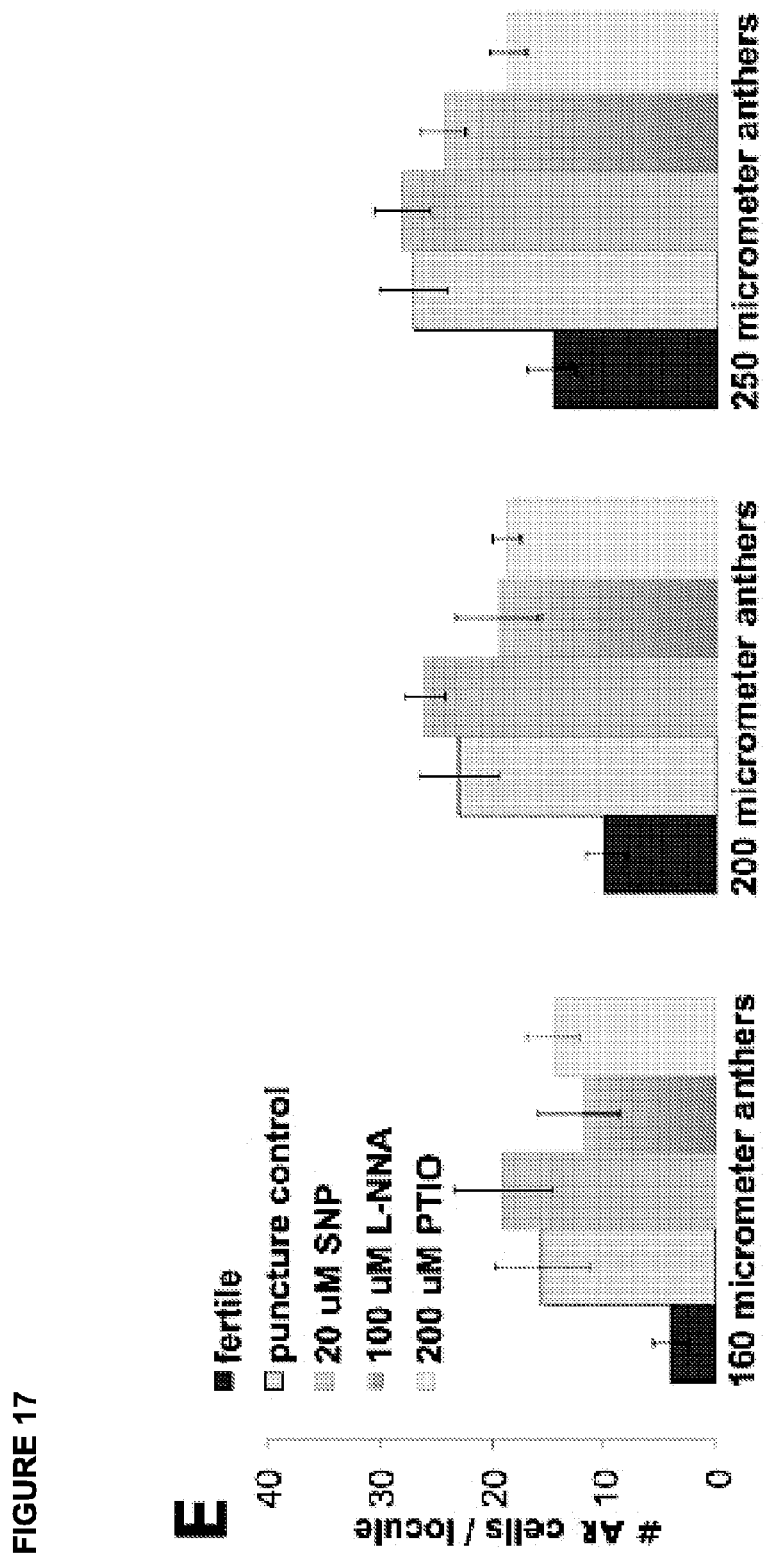
Figure 17:
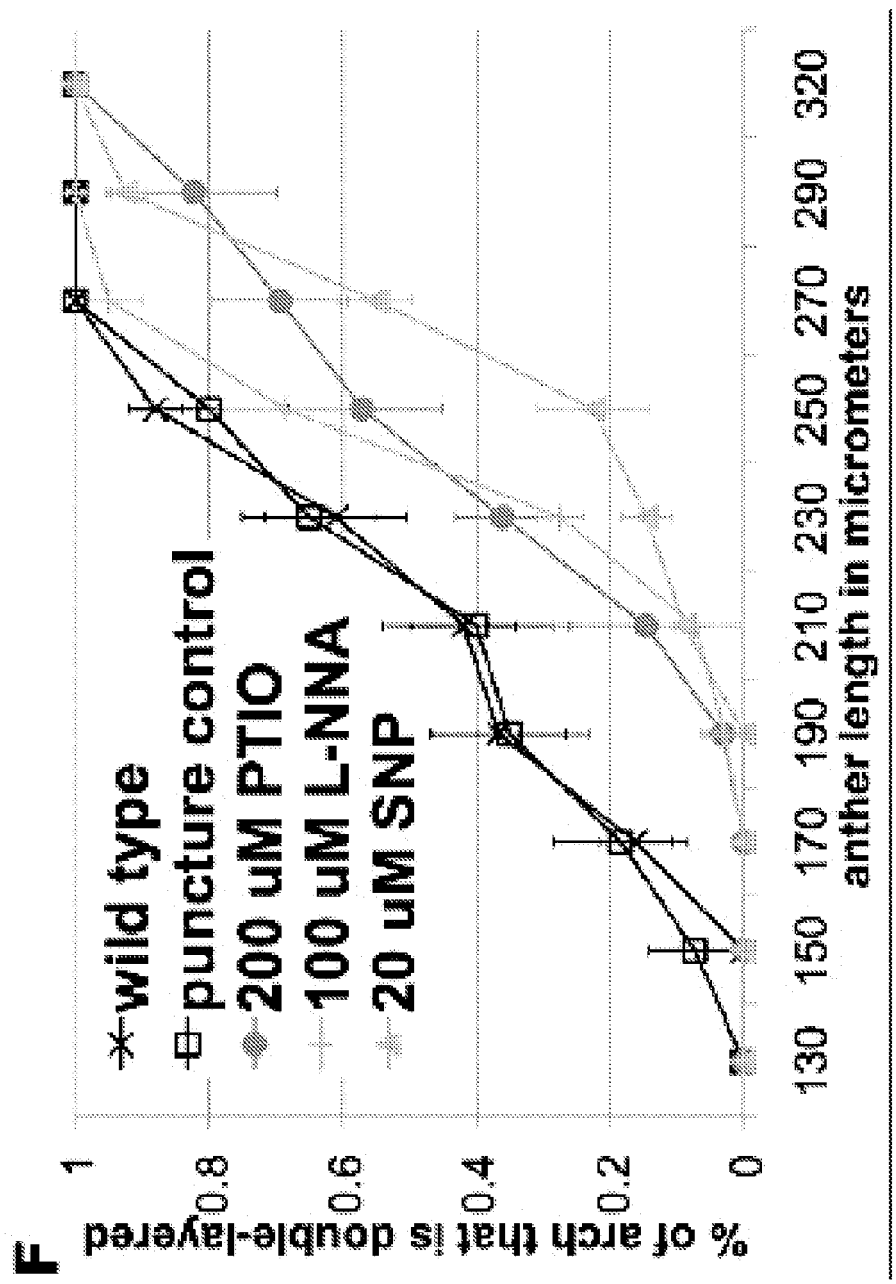

Cellular redox was perturbed chemically by injecting 1 mL of 1 mM $H_2O_2$ or 10 mM KI (a peroxide scavenger). While KI did not alter total L2 or peripheral counts, $H_2O_2$ treatment greatly reduced these cell numbers (FIG. 3A-C) compared to a needle puncture control. KI dramatically promoted AR specification (FIG. 3D) and increased AR:total L2 ratios (FIG. 3E). Conversely, $H_2O_2$ lowered AR cell counts and inhibited subsequent somatic bilayer formation (FIG. 3D-F). Two promoters of ROS, 200 μM PTIO or 100 μM L-NNA, slightly suppressed AR counts; 20 μM SNP, a ROS inhibitor, increased AR cells slightly compared to puncture controls (FIGS. 17, A and E). Interestingly, all three chemicals delayed AR morphological differentiation (FIG. 17B-D) and somatic bilayer development, particularly SNP (FIG. 17F).

Collectively, these treatments highlight the key role played by redox in the specification of AR cells in that the L2-d cells are poised for a redox-dependent signal relayed through MSCA1 to establish AR fate. In this developmental context, hypoxia increases cell proliferation, placing more L2-d cells in central positions earlier where AR fate specification normally starts; conversely treatments that increased oxygen/ROS suppressed AR specification and hence also delayed somatic niche formation.

Example 6

Manipulation of Redox Leads to Ectopic AR Specification

Figure 4:
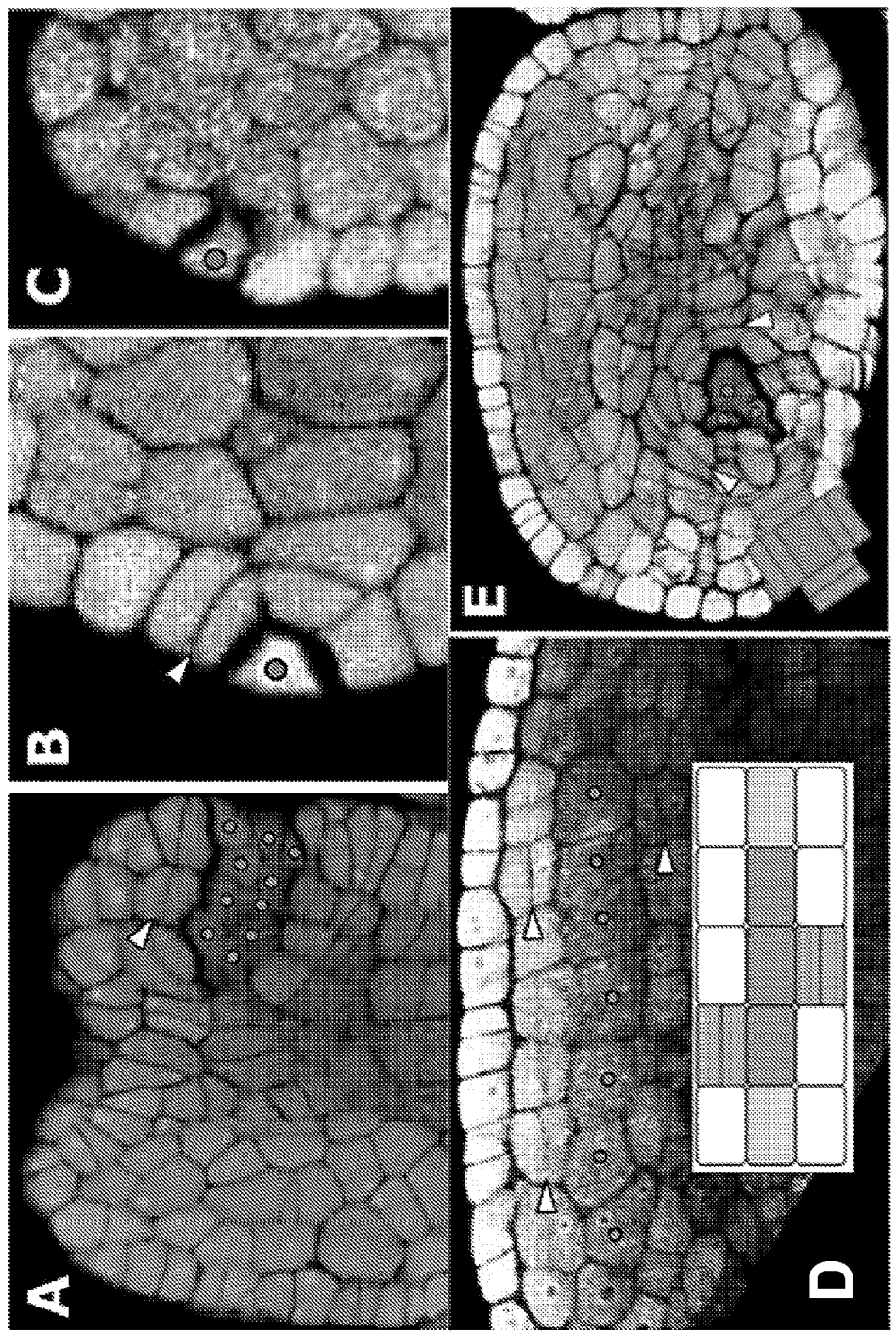
FIG. 4. Ectopic archesporial cell formation. (A-C) $N_2$ needle treatment with (A) multiple AR, (B) a single epidermal AR, and (C) an epidermal AR in a mac1 anther missing somatic niche. (D) Fertile untreated anther with diagram showing normal development. (E) $O_2$ needle treatment with three ectopic inner-locule AR; diagram emphasizes instructive role of AR in niche formation. (F-I) 20 µM SNP injected into msca1 caused ectopic AR. (F) Left: Transverse reconstruction showing locule AR. Central: Longitudinal section with AR embedded in locule vasculature. Right: Transverse reconstruction showing vascular bundle (defining msca1 phenotype). (G,H) Subepidermal AR surrounded by niche. (I) AR cell cluster.
Figure 4:
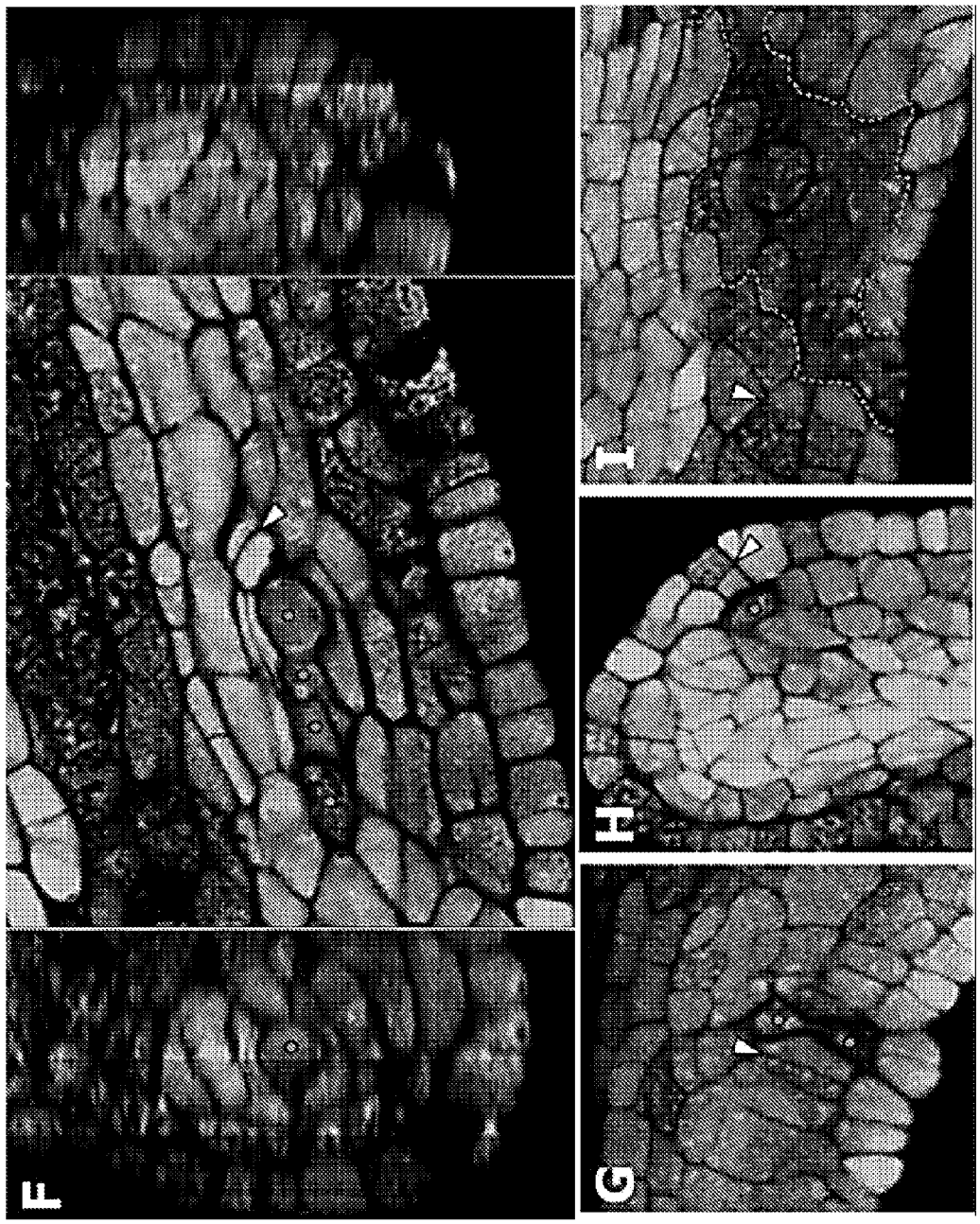

Ectopic AR were identified based on characteristic morphology and ability to direct periclinal divisions locally (FIG. 4). Singular AR cells occurred but more commonly an AR chain wove through the tissue, without regard to body axes. These AR were originally non-locule floral cells that acquired a germinal fate upon treatment. Oriented, periclinal divisions in surrounding somatic cells reminiscent of SPL/EN layer ontogeny were observed, adjacent to AR in connective, vasculature, and epidermis (FIG. 4A, B, E). In addition to organizing a somatic niche, ectopic AR cells can be inferred to be self-promoting, organizing a file similar to the normal locular column (FIG. 4A).

Figure 18:
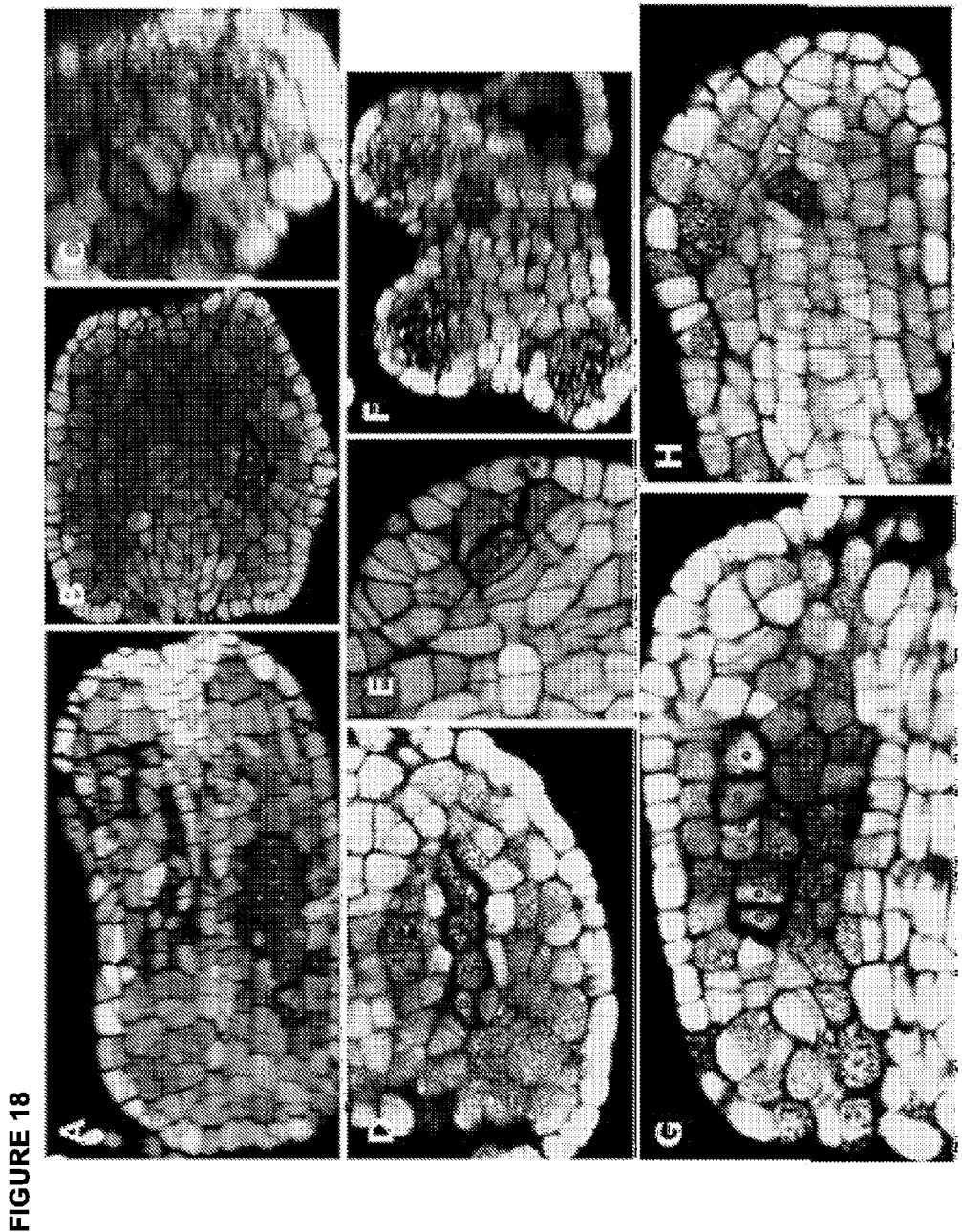
FIG. 18. Ectopic AR in oxidizing treatments. (A-E) $O_2$ needle treatments. (A) Large cluster of ectopic AR in locule and adjacent vasculature in a fertile anther. (B) Anther with ectopic AR near the vasculature. (C) Ectopic AR cell near connective/locule boundary in a fertile anther with neighboring cell making a double layer. (D) Column of ectopic AR in connective tissue surrounding by cells dividing orthogonal to a source of MAC1 signal from the AR column. (E) Four AR cells near the epidermis surrounded by the double-layered somatic niche. (F-H) $H_2O_2$ treatment. (F) AR cell specified adjacent to the vasculature as viewed in transverse reconstruction. (G) Column of AR in connective tissue. (H) Single AR in connective tissue.
Figure 19:
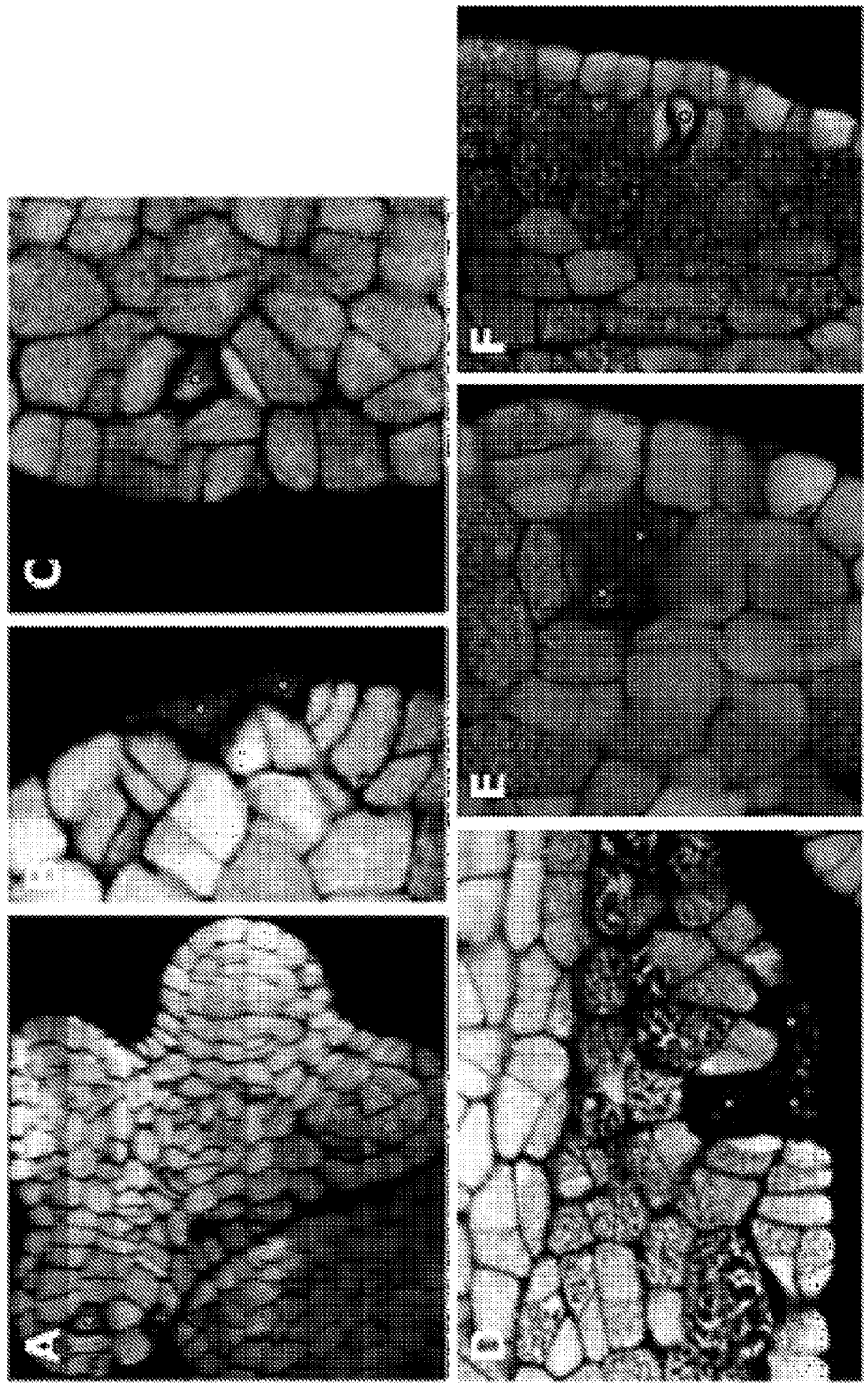
FIG. 19. Ectopic AR in $N_2$ needle treatments. (A,C) Subepidermal ectopic AR in a fertile anther with niche-making divisions in epidermal and subepidermal neighbors. (B) Two epidermal AR accompanied by layer-adding divisions in neighboring cells of two layers. (D) Ectopic AR in epidermal and subtending tissues, surrounded by dividing cells. (E) Duet of ectopic AR on the epidermis surrounded by divisions orthogonal to the putative MAC1 signal source. (F) Newly differentiated subepidermal AR cell with a small niche.

In total, 4.3% of 1490 anthers imaged had ectopic AR cells; 3.0% and 6.2% in oxidizing and reducing treatments, respectively (Table 2 and 3). AR location was biased depending on treatment. In oxidizing treatments, 70% of ectopic AR were near the VT (FIG. 1E and FIG. 18) and 30% were epidermal or subepidermal (Table 3). This bias for internal locations may reflect an intrinsic capacity for deeper tissues to achieve hypoxia despite oxidizing conditions. Reducing treatments showed the opposite bias: 17% of ectopic AR were internal while 83% were more superficial (FIG. 4A-C; FIG. 19; Table 2). We hypothesize that normally, the hypoxic airspace and cellular properties achieve MSCA1-mediated activation of AR specification first in the centrally located L2-d cells surrounded by L2-d. Quickly these pre-AR increase MAC1 expression to direct neighbor cell periclinal division. Ectopic AR distribution supports the earlier morphometric observation that AR cells, once specified, are organizing centers (FIGS. 4D and 4E) and that AR specification is an emergent property independent of lineage.

Example 7

Inhibition of ROS Formation Rescues Anther Cell Fate Specification in Msca1

Gas and chemical treatments caused ectopic AR cells in mac1 anthers, but there was no subsequent stimulation of periclinal division in neighboring L2-d, confirming that somatic niche formation requires MAC1 (FIG. 4C). In oxidizing treatments ($H_2O_2$, PTIO, L-NNA) msca1 lacked AR, however, reductive treatments (KI, SNP) caused AR specification (FIG. 4F-J). 20 µM SNP was strongest: 37% of treated msca1 anthers had AR cells. Two anthers out of 30 were rectified—locules had full AR columns surrounded by differentiated SPL and EN. With KI treatment, 9.5% of msca1 anthers contained AR. These data indicate show that a reductive environment is sufficient to activate the unidentified target(s) of MSCA1, causing AR specification.

Example 8

Immature Anthers Use Alternative Metabolism to Maintain Low ROS and Activate Hormone Biosynthetic Genes after AR Specification Many thioredoxins are required during floral organ development, suggesting excessive ROS cause sterility. Genes that lower ROS and support reducing capacity are expressed in young anthers by microarray analysis (Table 4). Many of these are specifically enriched in laser microdissected AR at later stages (Table 5) and absent in msca1 (Table 6), suggesting they are important in the germline. Genes involved in energy generation that bypass the mitochondrial electron transport chain, a major source of ROS (36) are highly represented. Five of seven glyoxylate shunt enzymes are enriched in AR cells (Table 5) and two are missing in msca1, suggesting an increased capacity in this peroxisomal/cytoplasmic process in AR cells. These alternative pathways avoid ROS production, facilitating maintenance of cellular hypoxia.

AR specification activates cascades of gene expression in hormone pathways—up-regulation of enzymes for making growth regulators ethylene, gibberellins, and cytokinin and jasmonic acid controlling selective abortion of female floral parts in maize tassel florets. Transcripts for controlling cytokinin and jasmonic acid production are absent in msca1 (Table 6). Conversely, abscisic-aldehyde oxidase, which produces the hormone abscisic acid and $H_2O_2$, is upregulated in msca1 anthers and missing from AR cells (data not shown).

Figure 5:
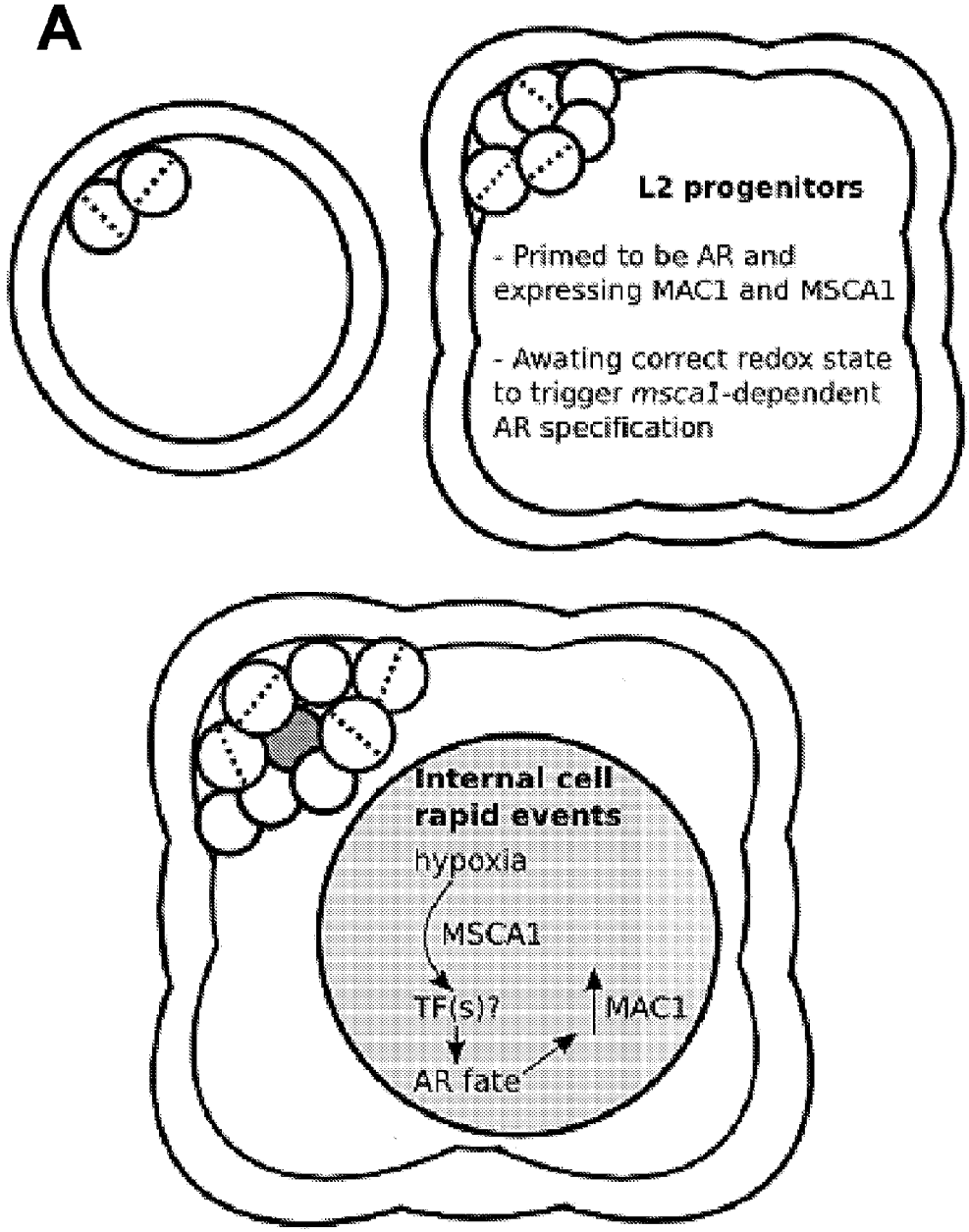
FIG. 5. (A-C) Model of germinal and somatic niche specification.
Figure 5:
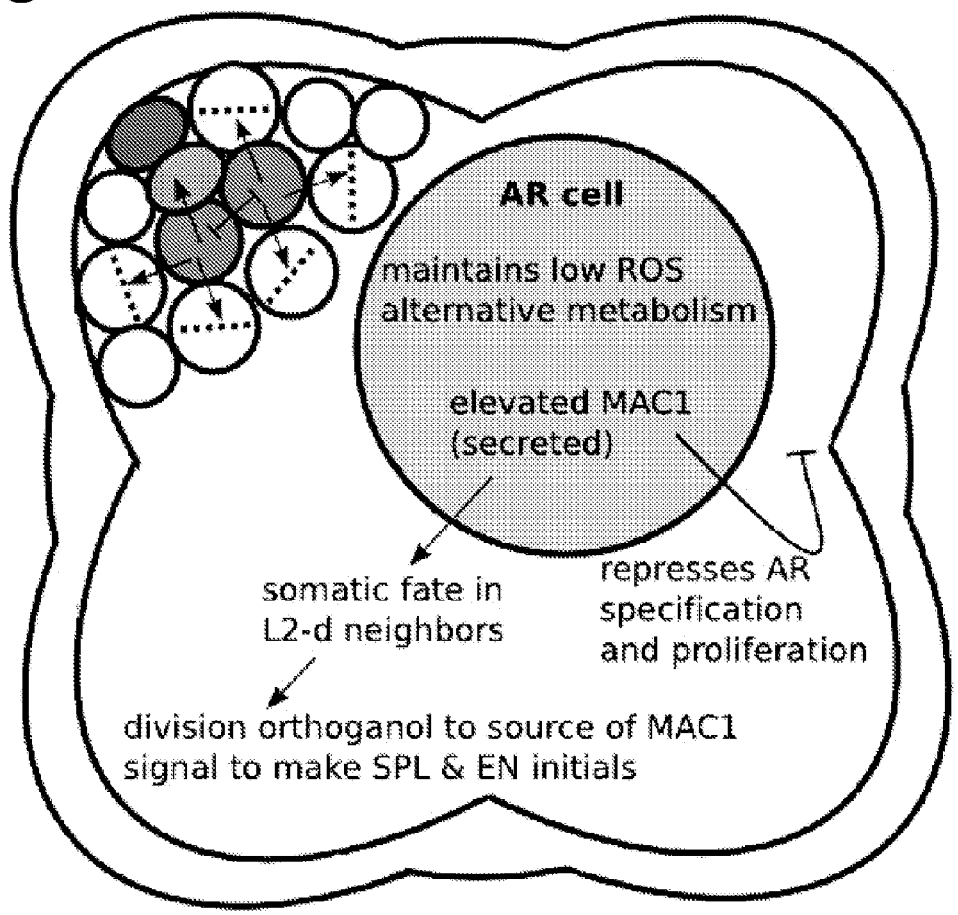

In conclusion, the analysis described above has debunked the lineage model through discovery that multiclonal AR arise within a field of pluripotent cells all expressing the MAC1 proliferation regulator. It is proposed that the central locular cells—those with only L2-d neighbors where locules are widest—achieve a hypoxic threshold to trigger MSCA1 glutaredoxin-mediated activation of the AR specification pathway. MAC1 production may be rapidly elevated in AR, which become signaling centers to repress their own proliferation and to activate neighboring L2-d cells to conduct a single periclinal cell division to establish the EN and SPL. These events proceed from the center towards the anther base and tip, resulting within 40 hours in locules with a column of central AR cells encircled by two somatic rings (FIG. 5). Concomitantly, anthers have more than doubled in length from both continual anticlinal cell division in somatic cells and substantial AR cell expansion.

The capacity to differentiate as an AR cell is not restricted to central L2-d cells. When a more reducing environment is imposed, subepidermal cells can become AR; in an oxidizing environment, internal connective cells adjacent to the vasculature can differentiate as AR. These observations reinforce the conclusion that AR differentiation is an emergent property dependent on physiological conditions and not the consequence of lineage or unique cell division patterns. Our results illustrate the inherent plasticity in plant development and capacity to reprogram cellular fate. In contrast to animals, plant germinal cells arise first and organize their somatic support tissues and can mature to functional meiocytes in the absence of normal soma.

The tables discussed above are described in more detail below.

Table 1. Pre-meiotic (1000 µm) AR-enriched transcripts in fertile and mac1. Laser microdissected AR cells from mutant and fertile sibling were compared on microaffay in duplicate (dye swap). Expression of 297 genes found to be enriched in AR cells was nearly identical (96.4% similar) between the two sample types according to ON/OFF categorization. 3.3% of transcripts were present and low in fertile but absent in mac1.

TABLE 1

| | mac1 vs fertile laser microdissected AR cells | |
| --- | --- | --- |
| GeneName | Fertile 1.0 mm AR | mac1 1.0 mm AR |
| TC307437 | 95.67712983 | 84.07312067 |
| TC306331 | 1079.548402 | 264.9401618 |
| AI944295 | 34.37626419 | 51.05627326 |
| TC311757 | 111.1946916 | 183.8111666 |
| TC313596 | 49.40334534 | 163.1255793 |
| TC313657 | 63.72220656 | 70.12026157 |
| TC305266 | 2382.71292 | 980.4346796 |
| TC308593 | 55.49287126 | 46.52063661 |
| TC287318 | 53.18202525 | 52.92950293 |
| TC301402 | 500.5313976 | 220.3197659 |
| TC294630 | 58.84547306 | 138.4968808 |
| TC308047 | 175.3424341 | 150.4634954 |
| CO533393 | 59.78950946 | 54.36291023 |
| TC289712 | 897.6810892 | 509.4528295 |
| BQ163730 | 797.997094 | 757.363686 |
| CN844996 | 0 | 0 |

TABLE 1-continued mac1 vs fertile laser microdissected AR cells

| GeneName | Fertile 1.0 mm AR | mac1 1.0 mm AR |
|---|---|---|
| TC279560 | 99.85672768 | 71.99330928 |
| TC296845 | 272.519121 | 130.0773545 |
| TC289757 | 0 | 0 |
| TC281079 | 397.274983 | 229.0728002 |
| TC284042 | 214.9946237 | 336.0149013 |
| TC310354 | 2602.038545 | 1751.558065 |
| TC283445 | 526.5235604 | 424.6700257 |
| TC279480 | 170.6815735 | 264.7150863 |
| TC296658 | 58.80599881 | 48.10159373 |
| TC309174 | 74.41210637 | 60.93695761 |
| TC284552 | 82.90374255 | 64.00463337 |
| TC302598 | 94.97989361 | 51.86412996 |
| TC282176 | 393.5655129 | 226.8877806 |
| CF633046 | 77.46883347 | 59.10070713 |
| TC308051 | 40.09309021 | 51.02610788 |
| TC284526 | 0 | 0 |
| TC284637 | 633.7723397 | 259.7908228 |
| TC314658 | 162.4711963 | 84.99540484 |
| TC289172 | 407.7935434 | 459.7894971 |
| TC312972 | 101.5536767 | 93.75086208 |
| TC313076 | 45.29763146 | 58.73100873 |
| TC284770 | 51.77705382 | 75.51744347 |
| TC289461 | 212.5565746 | 54.76266694 |
| BM378145 | 388.0556647 | 98.10863633 |
| TC279550 | 2383.754992 | 599.9313944 |
| TC311769 | 53.64284348 | 47.81585362 |
| TC310843 | 404.1735725 | 439.6208285 |
| BM259506 | 55.3958742 | 91.92204209 |
| TC310187 | 6915.72564 | 2443.667318 |
| TC296799 | 80.73118854 | 68.57995674 |
| TC300972 | 53.16208068 | 59.10668133 |
| TC295938 | 52.95327142 | 46.29008046 |
| CF635716 | 0 | 0 |
| TC307997 | 331.6539139 | 209.0008309 |
| TC315563 | 64.93181013 | 59.26792709 |
| DT643307 | 143.2447593 | 161.9392299 |
| CB278279 | 134.2521954 | 82.22318366 |
| TC300898 | 68.32740785 | 50.08753141 |
| DT645987 | 78.12198158 | 79.47638579 |
| TC294308 | 58.36503218 | 62.93727412 |
| TC287640 | 360.2878165 | 583.3513772 |
| BM500607 | 0 | 0 |
| DR813132 | 0 | 0 |
| TC289774 | 124.2232303 | 189.8817892 |
| TC293138 | 70.98848559 | 67.92631777 |
| TC295272 | 346.614401 | 335.4050998 |
| TC301356 | 1253.35691 | 736.7954656 |
| DT943054 | 84.42370603 | 66.54232099 |
| DT943053 | 206.9546781 | 80.71916298 |
| TC305979 | 247.3254306 | 147.8693308 |
| TC302216 | 51.7588177 | 57.19684965 |
| TC284771 | 466.1638402 | 361.8391664 |
| TC303615 | 72.00143998 | 62.54195767 |
| TC311135 | 354.4349431 | 136.5067298 |
| TC309440 | 50.42079153 | 55.06625832 |
| TC289387 | 214.8070811 | 145.3531013 |
| TC281453 | 727.1751514 | 408.216641 |
| TC286486 | 124.2140839 | 61.33957075 |
| TC288800 | 313.5672954 | 150.7640256 |
| TC297030 | 0 | 0 |
| TC303749 | 0 | 0 |
| TC282058 | 233.2122551 | 348.1096016 |
| TC287674 | 76.2907731 | 62.88739834 |
| TC293448 | 326.1380076 | 596.2198778 |
| TC283790 | 0 | 0 |
| TC312974 | 70.6465045 | 77.51260887 |
| CF019406 | 155.8051816 | 182.908681 |
| TC280500 | 125.7041044 | 135.4374108 |
| CD447985 | 100.6876167 | 287.1474575 |
| CF626131 | 31.40707802 | 81.79162576 |
| TC313491 | 414.7050964 | 329.1983123 |
| TC292774 | 11471.68654 | 8276.248443 |
| TC314580 | 77.34701508 | 0 |
| TC283173 | 46.52889371 | 43.80438018 |
| TC298797 | 332.8585625 | 153.4906492 |
| DR906542 | 81.28372364 | 93.96024521 |
| TC283852 | 139.99457 | 178.3741784 |
| TC305717 | 0 | 0 |
| TC309747 | 304.0202017 | 136.1177695 |
| TC301790 | 157.8096888 | 113.7832625 |
| TC285165 | 272.5942657 | 114.6821327 |
| TC311526 | 2093.383438 | 2001.152863 |
| TC306072 | 771.8521974 | 366.9940536 |
| TC293449 | 43.62793519 | 49.83722401 |
| TC283691 | 959.7017959 | 487.3918758 |
| TC305158 | 324.4745786 | 328.1548585 |
| DR829208 | 56.41507104 | 48.88664055 |
| TC310683 | 0 | 0 |
| DT647788 | 59.71662611 | 60.01717154 |
| TC306026 | 127.481958 | 77.9935347 |
| AW231811 | 45.86857187 | 44.69558492 |
| TC289354 | 138.2341078 | 160.2965611 |
| TC294269 | 59.85998257 | 50.31586216 |
| TC308574 | 0 | 0 |
| CD995275 | 94.09345226 | 83.18669616 |
| TC315488 | 58.59414412 | 52.92950293 |
| TC314126 | 0 | 0 |
| TC283431 | 42.92411634 | 123.9750306 |
| TC310688 | 651.9157536 | 493.1097966 |
| TC296255 | 54.1247332 | 71.3270713 |
| TC307982 | 59.840481 | 300.6115267 |
| DR795221 | 521.2205201 | 345.3780759 |
| TC295193 | 59.3735292 | 0 |
| TC297828 | 0 | 0 |
| TC294408 | 130.0954093 | 63.65029147 |
| TC294126 | 92.1462186 | 64.2339567 |
| TC302695 | 0 | 0 |
| AM1 | 77.23125706 | 79.71967102 |
| TC283097 | 696.3844869 | 429.9270135 |
| CO440202 | 73.59899731 | 57.05783345 |
| TC299943 | 1544.125229 | 492.583773 |
| TC280985 | 428.2558912 | 178.5307879 |
| TC302095 | 1305.837448 | 1327.126582 |
| TC284035 | 56.57214291 | 52.56340443 |
| TC297465 | 792.188638 | 321.6562161 |
| TC310988 | 112.8858766 | 49.82815996 |
| TC309808 | 59.21096637 | 87.84509547 |
| CF040072 | 191.5676404 | 77.14493736 |
| TC298200 | 136.9230345 | 71.611406 |
| TC311848 | 2245.461026 | 3165.842307 |
| TC313084 | 810.8961131 | 250.7503366 |
| DT647408 | 102.0221782 | 56.51616669 |
| TC307549 | 178.5069027 | 102.600739 |
| CF629011 | 92.99569652 | 170.5018618 |
| TC292387 | 336.0413612 | 224.952393 |
| TC286746 | 915.494291 | 868.6519043 |
| TC282507 | 505.0306969 | 557.7312494 |
| CD436448 | 90.87758729 | 52.00198386 |
| TC295587 | 132.9112592 | 62.78669449 |
| TC286055 | 546.517299 | 331.3216798 |
| TC285655 | 23238.03077 | 7972.935106 |
| TC314264 | 184.2125104 | 114.837095 |
| TC293287 | 187.5218337 | 168.980226 |
| TC282818 | 472.2628263 | 250.2614084 |
| TC308341 | 57.61498895 | 0 |
| TC279890 | 1393.585894 | 1004.123466 |
| TC304579 | 560.4364633 | 598.4057111 |
| TC301734 | 79.90131387 | 45.7298984 |
| TC301530 | 195.7874614 | 85.20835195 |
| TC280797 | 548.379991 | 178.6737783 |
| TC313063 | 193.1631408 | 159.7390261 |
| CO441573 | 408.3721866 | 615.5620625 |
| TC306070 | 95.25481482 | 90.29357019 |
| TC303407 | 0 | 0 |
| TC295047 | 646.1408063 | 446.6588772 |
| TC289727 | 53.95717285 | 47.27748914 |
| TC307255 | 713.944836 | 354.847537 |
| TC296050 | 74.20392083 | 60.60728999 |
| TC279580 | 166.0303249 | 163.7824891 |
| TC310105 | 55.60258895 | 0 |

TABLE 1-continued mac1 vs fertile laser microdissected AR cells

| GeneName | Fertile 1.0 mm AR | mac1 1.0 mm AR |
|---|---|---|
| TC312091 | 93.56727032 | 67.92631777 |
| CX725290 | 160.5580007 | 72.31739685 |
| TC292021 | 262.2396327 | 104.3311247 |
| TC283684 | 126.3624637 | 75.07417538 |
| TC295259 | 59.6055818 | 48.4806852 |
| TC301446 | 375.7085906 | 218.2557565 |
| BG837957 | 0 | 0 |
| TC313569 | 101.8307465 | 57.25324332 |
| TC305399 | 105.8639692 | 187.7092971 |
| DT943243 | 0 | 0 |
| TC315034 | 85.75561019 | 68.39939242 |
| TC287642 | 202.4879791 | 133.4871243 |
| BM340065 | 0 | 0 |
| TC314450 | 40.49991688 | 88.41546939 |
| TC295884 | 0 | 0 |
| TC301395 | 1042.845702 | 471.1871674 |
| TC295868 | 97.59639517 | 139.7266617 |
| TC295891 | 0 | 0 |
| TC302888 | 119.6313131 | 93.84405118 |
| TC307873 | 144.9868495 | 287.4749122 |
| TC303479 | 58.26322571 | 0 |
| TC302844 | 0 | 0 |
| TC284163 | 370.9992501 | 292.1683994 |
| TC308672 | 0 | 0 |
| TC284146 | 140.6033291 | 66.81754178 |
| TC289458 | 597.511027 | 288.1767591 |
| TC313835 | 139.7374381 | 186.5215453 |
| TC279806 | 3854.441637 | 4641.760037 |
| CD995946 | 0 | 0 |
| TC310318 | 98.26794261 | 0 |
| CB280793 | 1780.410599 | 352.5545267 |
| TC287858 | 0 | 0 |
| TC302617 | 132.4840843 | 63.03900082 |
| TC299289 | 56.71279289 | 47.46020494 |
| TC297564 | 69.56692916 | 83.51272341 |
| TC293567 | 3225.61385 | 2146.858904 |
| TC280737 | 41.16428165 | 93.0702871 |
| TC280740 | 42.70849558 | 51.58390231 |
| CK787298 | 0 | 0 |
| TC308668 | 58.15743262 | 57.0633758 |
| TC298179 | 92.32884142 | 67.45103963 |
| DT943270 | 0 | 0 |
| TC314427 | 75.62850535 | 56.87919119 |
| TC289341 | 291.6695136 | 331.2430558 |
| TC285412 | 76.48856188 | 59.55840406 |
| TC295182 | 178.3731746 | 99.50870209 |
| TC304232 | 47.9598774 | 45.57410277 |
| TC314544 | 2161.122647 | 876.2024627 |
| DT946613 | 159.4485855 | 80.83777758 |
| TC307673 | 446.9807695 | 407.0687669 |
| TC312497 | 0 | 0 |
| TC293566 | 2213.608777 | 1699.507901 |
| TC295697 | 42.27594089 | 47.65371298 |
| TC283769 | 0 | 0 |
| TC290945 | 46.73846168 | 48.32619184 |
| TC312299 | 69.99075634 | 53.29838683 |
| TC306976 | 368.8858385 | 260.7798613 |
| DR830496 | 0 | 0 |
| TC284316 | 52.86259854 | 0 |
| TC291853 | 66.66033897 | 56.58698627 |
| TC293263 | 1004.586223 | 1567.943611 |
| TC301331 | 225.7178044 | 187.1668671 |
| TC309875 | 219.0155963 | 107.7749231 |
| DN586214 | 33.60814539 | 62.44778633 |
| TC283905 | 0 | 0 |
| TC309993 | 650.7811934 | 519.0726696 |
| TC314530 | 0 | 0 |
| TC281589 | 80.21241157 | 53.09080657 |
| TC298798 | 1294.508678 | 612.3146423 |
| TC282924 | 302.4361836 | 182.515782 |
| CF059625 | 1028.631046 | 64.13388093 |
| TC304331 | 0 | 0 |
| TC314676 | 220.4652972 | 184.5969239 |
| TC289753 | 0 | 0 |
| TC307556 | 85.24776254 | 69.10679706 |
| TC305157 | 113.4204815 | 73.17745341 |
| TC288590 | 57.64982886 | 0 |
| TC287319 | 3140.509713 | 4312.286843 |
| TC284111 | 760.0155031 | 824.2716677 |
| TC291009 | 372.1974694 | 282.9471457 |
| TC307363 | 287.179738 | 106.7155498 |
| TC295705 | 176.0201768 | 236.3547719 |
| TC296253 | 0 | 0 |
| TC284639 | 111.2052415 | 203.3674004 |
| TC290471 | 2034.500262 | 1337.143831 |
| TC284496 | 68.86940923 | 82.31433628 |
| TC285351 | 116.7297869 | 87.88576065 |
| TC288463 | 51.90140882 | 46.54759213 |
| TC295239 | 375.7971006 | 149.1620124 |
| TC306328 | 60.13921057 | 51.139515 |
| CO526721 | 50.48071934 | 46.12864615 |
| DT652253 | 94.37622386 | 61.10986614 |
| TC306547 | 705.3559683 | 355.2970021 |
| TC287826 | 53.70407672 | 46.05780379 |
| TC297071 | 59.81638098 | 70.21785149 |
| AI692111 | 388.3118336 | 121.746282 |
| TC302041 | 57.12271273 | 79.44769786 |
| BG319836 | 208.1453481 | 228.8166057 |
| TC290304 | 81.35495105 | 52.75086823 |
| TC312257 | 134.1002277 | 55.99122179 |
| TC287864 | 183.2455121 | 114.9431138 |
| TC304530 | 80.36473667 | 93.52600123 |
| CD573220 | 54.53114671 | 0 |
| TC313810 | 0 | 0 |
| TC309689 | 51.34165473 | 51.8799893 |
| TC291467 | 187.3332856 | 115.280456 |
| TC286409 | 176.4090974 | 138.2014654 |
| TC298303 | 1230.223882 | 404.3580786 |
| TC279657 | 0 | 0 |
| DT650280 | 83.4421659 | 110.1795733 |
| TC292121 | 4238.092027 | 3467.75276 |
| TC283041 | 56.74662309 | 0 |
| TC297993 | 160.3011285 | 134.0209233 |
| TC283544 | 83.04142027 | 63.75903843 |
| DN559761 | 215.1132188 | 145.6597419 |
| TC280195 | 589.0162083 | 526.2160664 |
| TC284424 | 1326.708569 | 444.2494158 |
| CA827264 | 110.0607095 | 0 |
| TC293183 | 386.3492741 | 213.1727306 |
| TC296831 | 545.6933491 | 313.8870554 |
| TC294651 | 92.11170241 | 77.03576165 |
| TC304557 | 80.89938179 | 55.75657607 |
| TC283469 | 186.3072478 | 120.1745603 |
| TC310367 | 115.6898354 | 92.41224596 |
| BG841754 | 143.1032139 | 135.5543952 |
| TC306103 | 0 | 0 |
| TC311214 | 85.73207712 | 131.8975851 |
| TC292342 | 237.6728533 | 279.77182 |
| BG319898 | 0 | 0 |
| TC315043 | 136.2191327 | 129.9252727 |
| TC282918 | 191.530038 | 127.53082 |

Table 2. Ectopic AR formation in reducing treatments that increase hypoxia or lower $H_2O_2$. Ectopic AR cells were defined by their morphological similarities with normal AR cells combined with non-locular location. The first two rows give the treatment type and genotype, and the next two rows give the general effects of the treatments on AR counts and SPL/EN progression as presented in FIG. 2, FIG. 3, and FIG. 17 (plus other trials that were not discussed). The next two rows give the frequency of observing AR in each treatment/ genotype combination. By far the protocol that caused the highest frequency of ectopic AR was the SNP treatment on the msca1 mutant (37% of anthers had AR). KI on msca1 (9.5%) and SNP+N2 on fertile (16.2%) treatments also resulted in many ectopic AR. Exogenous $N_2$ application with the hose protocol did not cause ectopic AR in any anthers; we speculate that this is a gentler treatment than the direct application of gas through the needle. Next the ectopic AR location is tallied as being either superficial (near or on the EPI) or internal (near or in the CT and VT). In reducing treatments ectopic AR were biased for peripheral tissues. Finally, the characteristics of the ectopic AR are given in the final two rows, including the presence of periclinal divisions generating an EN/SPL-like bilayer surrounding the AR (which were absent in all mac1 ectopic AR) and the average count of AR cells in each instance. Totals are to the right.

TABLE 2

Ectopic AR in reducing treatments

| | TREATMENTS (REDUCING) | | | | | | | | | | | |
|---|---|---|---|---|---|---|---|---|---|---|---|---|
| | $N_2$ (direct) | $N_2$ (hose) | KI | SNP | $N_2$ + SNP | $N_2$ (direct) | KI | SNP | $N_2$ (direct) | KI | SNP | TOTAL |
| GENOTYPE | fertile | fertile | fertile | fertile | fertile | mac1 | mac1 | mac1 | msca1 | msca1 | msca1 | |
| TREATMENT EFFECTS | | | | | | | | | | | | |
| AR count | extra | extra | extra | extra | extra | extra | extra | extra | none | extra | extra | |
| SPL/EN timing | early | early | early | delayed | delayed | N/A | N/A | N/A | N/A | N/A | N/A | |
| COUNT | | | | | | | | | | | | |
| total anthers | 95 | 88 | 100 | 23 | 37 | 85 | 20 | 15 | 45 | 63 | 30 | 601 |
| # having ectopic AR | 4 | 0 | 2 | 1 | 6 | 7 | 0 | 0 | 0 | 6 | 11 | 37 (6.2%) |
| LOCATION | | | | | | | | | | | | |
| by EPI | 4 | 0 | 2 | 1 | 5 | 5 | 0 | 0 | 0 | 5 | 7 | 29 (83%) |
| by CT | 0 | 0 | 0 | 0 | 1 | 2 | 0 | 0 | 0 | 1 | 2 | 6 (17%) |
| CHARACTERISTICS | | | | | | | | | | | | |
| niche - forming | Y | N/A | Y | Y | Y | N | N/A | N/A | N/A | Y | Y | |
| AR per event | 5 | N/A | 7 | 17 | 4.2 | 3 | N/A | N/A | N/A | 3 | 7.5 | Avg = 5.4 |

Table 3. Ectopic AR formation in oxidizing treatments that increase oxygen and/or $H_2O_2$. Ectopic AR formation in oxidizing treatments was highly biased for the internal tissues. The organization of the table is the same as in Table 2.

TABLE 3

Ectopic AR in oxidizing treatments

| | TREATMENTS (OXIDIZING) | | | | | | | | | |
|---|---|---|---|---|---|---|---|---|---|---|
| | $O_2$ (direct) | $O_2$ (hose) | Air (direct) | Puncture | $H_2O_2$ | PTIO | L-NNA | $N_2$, PTIO | $N_2$, L-NNA | $O_2$ (direct) |
| GENOTYPE | fertile | fertile | fertile | fertile | fertile | fertile | fertile | fertile | fertile | mac1 |
| TREATMENT EFFECTS | | | | | | | | | | |
| AR count | extra | fewer | same | extra | fewer | fewer | fewer | normal | normal | extra |
| SPL/EN timing | delayed | late | same | same | delayed | delayed | delayed | delayed | delayed | N/A |
| COUNT | | | | | | | | | | |
| total anthers | 192 | 190 | 55 | 60 | 120 | 37 | 23 | 30 | 30 | 40 |
| # having ectopic AR | 18 | 0 | 3 | 0 | 0 | 4 | 1 | 2 | 0 | 0 |
| LOCATION | | | | | | | | | | |
| by EPI | 6 | 0 | 2 | 0 | 0 | 1 | 0 | 0 | 0 | 0 |
| by CT | 12 | 0 | 1 | 0 | 0 | 3 | 1 | 2 | 0 | 0 |
| CHARACTERISTICS | | | | | | | | | | |
| niche - forming | ~half | N/A | yes | N/A | N/A | yes | yes | yes | N/A | N/A |
| AR per event | 3.7 | N/A | 2 | N/A | N/A | 5 | 2 | 1.5 | N/A | N/A |

TABLE 3-continued

Ectopic AR in oxidizing treatments

| | TREATMENTS (OXIDIZING) | | | | | | | |
|---|---|---|---|---|---|---|---|---|
| | $H_2O_2$ | PTIO | L-NNA | $O_2$ (direct) | $H_2O_2$ | PTIO | L-NNA | TOTAL |
| GENOTYPE | mac1 | mac1 | mac1 | msca1 | msca1 | msca1 | msca1 | |
| TREATMENT EFFECTS | | | | | | | | |
| AR count | extra | extra | extra | none | N/A | N/A | N/A | |
| SPL/EN timing | N/A | N/A | N/A | N/A | N/A | N/A | N/A | |
| COUNT | | | | | | | | |
| total anthers | 18 | 12 | 11 | 29 | 21 | 12 | 9 | 889 |
| # having ectopic AR | 0 | 0 | 0 | 0 | 0 | 0 | 0 | 27 (3.0%) |
| LOCATION | | | | | | | | |
| by EPI | 0 | 0 | 0 | 0 | 0 | 0 | 0 | 8 (30%) |
| by CT | 0 | 0 | 0 | 0 | 0 | 0 | 0 | 19 (70%) |
| CHARACTERISTICS | | | | | | | | |
| niche - forming | N/A | N/A | N/A | N/A | yes | N/A | N/A | |
| AR per event | N/A | N/A | N/A | N/A | 2 | N/A | N/A | Avg = 4.2 |

Table 4. Ninety-eight transcripts found in early fertile anthers associated with redox regulation, metabolism, alternative energy metabolism, and hormone biosynthesis or signaling. A number of genes associated with the glyoxylate cycle (e.g. malate dehydrogenase, succinate dehydrogenase, pyruvate dehydrogenase) and ROS management (e.g. superoxide dismutase, glutathione S transferase, thioredoxin, and glutaredoxin-like) are highly expressed. These probes were chosen for inclusion here based on slight enrichment in mac1 mutant anthers (contains extra AR cells) to focus on genes that might be enriched or specifically expressed in AR cells.

TABLE 4

Early anther (alternative metabolism, ROS management, hormone biosynthesis)

| Public Annotation | ProteinID | Avg Intensity |
|---|---|---|
| glutathione transferase | GRMZM2G097989 | 40902.1016 |
| glutaredoxin-like, protein disulfide oxidoreductase | GRMZM2G118366 | 13410.5 |
| Acetyl-CoA C-acetyltransferase | GRMZM2G085474 | 10779.2998 |
| phosphatase | GRMZM5G836174 | 9445.04 |
| glyoxylase1 | GRMZM2G181192 | 8757.5 |
| lipoxygenase | GRMZM2G109056 | 5618.2998 |
| alpha trehalose phosphate synthase | GRMZM2G019183 | 4139.3599 |
| malate dehydrogenase | GRMZM2G154595 | 3351.1799 |
| phosphoenolpyruvate carboxykinase (ATP) | GRMZM5G870932 | 3032.53 |
| Ferritin-1, chloroplastic Precursor (EC 1.16.3.1) | GRMZM2G325575 | 3020.3799 |
| pyruvate kinase | GRMZM2G066290 | 2955.4099 |
| indole-3-acetic acid amido synthetase | GRMZM2G378106 | 2539.49 |
| indoel-3-acetic acid amido synthetase | GRMZM2G068701 | 2530.5701 |
| thioesterase family protein | GRMZM2G397661 | 2352.25 |
| DELLA protein Dwarf8 (giberellin response) | GRMZM2G14474 | 2329.95 |
| lipase | GRMZM2G080940 | 2042.47 |
| adenine phosphoribosyltransferase 2 | GRMZM2G071846 | 1956.67 |
| plastidic phosphate translocator-like protein1 | GRMZM2G130558 | 1931.9 |
| glucan endo-1,3-beta-glucosidase A6 | GRMZM2G458164 | 1919.5699 |
| Fructokinase-1 (EC 2.7.1.4)(ZmFRK1) | GRMZM2G086845 | 1814.39 |
| Fructokinase-2 (EC 2.7.1.4)(ZmFRK2) | GRMZM2G051677 | 1581.1801 |
| 2-C-methyl-D-erythritol 2,4-cyclodiphosphate synth | GRMZM5G835542 | 1553.8199 |
| glutaredoxin-like, protein disulfide oxidoreductase | GRMZM2G148867 | 1482.88 |
| palmitoyl protein thioesterase, palmitoyl-CoA hydrolase | GRMZM2G093880 | 1337.16 |
| Thiazole biosynthetic enzyme 1-1, chloroplastic Precursor | GRMZM2G018375 | 1143.49 |
| delta 1-pyrroline-5-carboxylate synthetase | GRMZM2G028535 | 1093.1899 |
| aldehyde oxidase | GRMZM2G141535 | 1061.72 |
| Sucrose synthase 1 (EC 2.4.1.13)(Sucrose-UDP glucose) | GRMZM2G089713 | 1009.43 |
| phosphoethanolamine; n-methyltransferase | GRMZM2G170400 | 1008.86 |
| fatty acid biosynthesis 1 | GRMZM2G099696 | 985.599 |
| N-acetyl-gamma-glutamyl-phosphate reductase | GRMZM2G038848 | 874.955 |
| alpha mannosidase | GRMZM2G172369 | 837.088 |
| beta-amylase | GRMZM2G082034 | 809.347 |
| mitochondrial membrane transport | GRMZM2G001915 | 777.19 |
| 1-deoxy-D-xylulose 5-phosphate synthase | GRMZM2G493395 | 762.93 |
| Phosphorylase (EC 2.4.1.1) | GRMZM2G074158 | 750.977 |
| 8-amino-7-oxononanoate synthase | GRMZM2G142030 | 650.977 |

TABLE 4-continued

Early anther (alternative metabolism, ROS management, hormone biosynthesis)

| Public Annotation | ProteinID | Avg Intensity |
| --- | --- | --- |
| flavonol synthase, flavanone 3-hydroxylase | GRMZM2G382569 | 643.543 |
| protochlorophyllide reductase B | GRMZM2G073351 | 594.071 |
| carbohydrate transporter | GRMZM2G336448 | 547.831 |
| glycerophosphodiester phosphodiesterase | GRMZM2G018820 | 532.703 |
| 3 oxoacyl synthase | GRMZM2G022563 | 527.998 |
| oxidoreductase activity | GRMZM2G099097 | 489.315 |
| ATP/ADP translocator | GRMZM2G359038 | 489.176 |
| lipoxygenase | GRMZM2G156861 | 481.988 |
| benzoxazinone synthesis9 | GRMZM2G161335 | 477.867 |
| proline oxidase | GRMZM2G117956 | 383.779 |
| succinate dehyrogenase | GRMZM2G064799 | 351.498 |
| 1-Cys peroxiredoxin PER1 (EC 1.11.1.15)(Thioredoxin) | GRMZM2G129761 | 351.4 |
| choline-phosphate cytidylyltransferase B | GRMZM2G132898 | 349.769 |
| dihydrolipoyllysine-residue acetyltransferase | GRMZM2G033644 | 338.432 |
| cis-zeatin-o-Beta-D-glucosyltransferase | GRMZM2G004858 | 320.143 |
| anthocyanidin-5-3-o-glucosyltransferase | GRMZM2G043295 | 271.983 |
| glutathione S-transferase GST 18 | GRMZM2G019090 | 268.51 |
| Acyl-CoA dehydrogenase | GRMZM2G052389 | 268.027 |
| triacylglycerol lipase like protein (LOC100281723) | GRMZM2G097704 | 256.52 |
| glutathione transferase19 | GRMZM2G335618 | 254.479 |
| UDP-glucose 6-hydrogenase | GRMZM2G328500 | 254.162 |
| propionyl-CoA carboxylase beta chain | GRMZM2G702490 | 250.399 |
| pyruvate dehydrogenase acetyl-transferring (NADH) | GRMZM2G127546 | 241.066 |
| adenosylmethionine-8-amino-7-oxononoate transanimase | GRMZM2G107739 | 237.93 |
| ABA-responsive protein | GRMZM2G106622 | 230.306 |
| transposon protein | GRMZM2G129540 | 209.502 |
| glutamate decarboxylase | GRMZM2G017110 | 201.038 |
| 3-beta-hydroxy-delta(5)-steroid dehydrogenase | GRMZM2G124434 | 189.517 |
| hydrolizing O-glycosyl compounds | GRMZM2G148176 | 189.42 |
| mannitol dehydrogenase | GRMZM2G167613 | 183.069 |
| myo-inositol kinase | GRMZM2G361593 | 182.398 |
| glutathioen S transferase | GRMZM2G129357 | 180.164 |
| ACC oxidase20 | GRMZM2G126732 | 179.766 |
| phospholipase C | GRMZM2G078650 | 179.49 |
| abscisic stress ripening protein2 | GRMZM5G854138 | 160.479 |
| aldehyde dehydrogenase NADP+ | GRMZM2G118800 | 158.511 |
| mitochondrial inner membrane protease subunit 1 | GRMZM5G833660 | 155.706 |
| phosphoenolpyruvate-carboxylase | GRMZM2G074122 | 149.124 |
| monoxygenase activity | GRMZM2G030831 | 132.602 |
| 4-coumarate coenzyme A ligase | GRMZM2G075333 | 132.191 |
| anther-specific proline-rich protein APG | GRMZM2G033566 | 128.784 |
| 40S ribosomal protein S28 | GRMZM2G455828 | 128.719 |
| pyrrolidone-carboxylate peptidase (LOC100281916) | GRMZM2G040515 | 128.623 |
| pfkB type carbohydrate kinase, denosine kinase, | GRMZM2G072091 | 122.442 |
| jasmonate induced protein | GRMZM2G172204 | 120.411 |
| steroleosin | GRMZM2G108338 | 117.447 |
| peroxidase 54 | GRMZM2G150893 | 116.016 |
| flavin like | GRMZM2G180251 | 104.022 |
| S-adenosylmethionine decarboxylase proenzyme Precursor | GRMZM2G154397 | 103.257 |
| glycerophosphodiester phosphodiesterase | GRMZM5G829946 | 92.6467 |
| phosphomevalonate kinase | GRMZM2G030839 | 90.1803 |
| alcohol dehydrogenase activity, oxidoreductase activity | GRMZM2G135277 | 89.5345 |
| protochlorophyllide reductase A | GRMZM2G084958 | 86.7847 |
| Cytochrome c oxidase subunit 2 (EC 1.9.3.1) | GRMZM5G862955 | 84.6176 |
| Sucrose-phosphate synthase (EC 2.4.1.14)(UDP-glucose) | GRMZM5G875238 | 83.2525 |
| hypothetical protein LOC100280278 | GRMZM2G071599 | 83.1616 |
| glucan endo-1,3-beta-glucosidase 3 | GRMZM5G824920 | 79.4262 |
| Glutamine synthetase root isozyme 1 (EC 6.3.1.2) | GRMZM2G050514 | 74.0272 |
| 1-Cys peroxiredoxin PER1 (EC 1.11.1.15)(Thioredoxin) | GRMZM2G129761 | 71.8648 |
| superoxide dismutase | GRMZM2G081585 | 65.4276 |
| myo-inositol transporter iolT | GRMZM2G060183 | 63.1028 |

Table 5. Pre-meiotic (650-750 μm) AR-enriched transcripts. Laser microdissected AR cells were compared in duplicate (dye swap) to whole anthers (WA) from the same tassel at the same stage. Genes that were expressed two-fold higher in AR versus WA have a log 2ratio>0.58 (p<0.05). Some genes just below the cutoff are listed because of their importance to either alternative metabolism or ROS handling. Along with many genes that scavenge ROS or manage reducing power (NADH enzymes and glutaredoxins, for example), 5 of the 7 genes of the glyoxylate cycle are enriched, suggesting AR cells are specifically using this alternative pathway to generate ATP without the side effect of endogenous ROS production.

TABLE 5

AR-enriched vs whole anthers at 700 μm

| annotation/description | ProteinMatchID | log2 ratio | p-value | AR intensity | WA intensity |
|---|---|---|---|---|---|
| aconitate hydratase | GRMZM2G020801 | 2.3593 | 5.466E−07 | 2344 | 451.4 |
| cytosolic glyceroldehyde-3-phosphate dehydrogenase | GRMZM2G176307 | 2.3410 | 3.656E−11 | 515 | 104.8 |
| NAD(P)H-quinone oxidoreductase subunit 5, chloroplast precursor | GRMZM5G894515 | 2.2645 | 3.098E−08 | 1604 | 309.8 |
| oxidoreductase, 2OG-Fe oxygenase family protein | GRMZM2G060079 | 2.1013 | 1.830E−12 | 235.7 | 57.5 |
| inositol hexaphosphate kinase (NADH metabolism) | GRMZM2G368799 | 2.0908 | 7.261E−14 | 2210.8 | 517 |
| NAD(P)H-quinone oxidoreductase subunit 4L, chloroplast precursor | GRMZM5G835775 | 1.8466 | 1.332E−08 | 1397.7 | 343.9 |
| Phosphoglucomutase, cytoplasmic 1 (PGM 1)(EC 5.4.2) | GRMZM2G109383 | 1.7508 | 1.078E−08 | 930.7 | 207.4 |
| NAD(P)H-dependent oxidoreductase | GRMZM2G415579 | 1.7465 | 8.852E−13 | 419.7 | 129.5 |
| Phosphoenolpyruvate carboxylase 2 (PEPCase 2)(PEPC) | GRMZM2G473001 | 1.7074 | 2.417E−12 | 306.2 | 91.2 |
| plastidic 2-oxoglutarate/malate transporter | GRMZM2G383088 | 1.6068 | 1.119E−12 | 1640.7 | 586.1 |
| NAD(P)H-quinone oxidoreductase subunit I, chloroplast precursor | GRMZM5G866223 | 1.5079 | 2.913E−08 | 13249.2 | 5437.1 |
| NAD(P)H-quinone oxidoreductase chain 4, chloroplast precursor | GRMZM5G800096 | 1.3949 | 1.126E−07 | 2048.7 | 638.5 |
| phosphoenolpyruvate carboxylase kinase 3 (PEPCK) | GRMZM2G096753 | 1.3686 | 8.897E−02 | 1308.5 | 1048.7 |
| dihydrolipoyl dehydrogenase | GRMZM5G806449 | 1.2499 | 1.187E−08 | 855.6 | 372.3 |
| S-adenosylmethionine decarboxylase proenzyme | GRMZM2G125635 | 1.2178 | 1.979E−09 | 4259.2 | 2545.2 |
| 3-isopropylmalate dehydrogenase | GRMZM2G120857 | 1.1363 | 1.066E−07 | 646.8 | 290.2 |
| isoamylase-type starch debranching enzyme ISO3 | GRMZM2G150796 | 1.0982 | 7.598E−08 | 160.7 | 78.4 |
| amylo-alpha-1,6-glucosidase | GRMZM2G040843 | 1.0850 | 1.535E−08 | 135.9 | 62.6 |
| NAD(P)H-quinone oxidoreductase subunit K, chloroplast precursor | GRMZM5G800980 | 0.9962 | 1.584E−03 | 2127.4 | 1081.6 |
| phosphatidate cytidylyltransferase | GRMZM2G062416 | 0.9907 | 6.525E−08 | 319.8 | 157.9 |
| peptidyl-prolyl cis-trans isomerase | GRMZM2G139210 | 0.9547 | 4.962E−08 | 256.4 | 127.5 |
| thiol oxidoreductase | GRMZM2G113216 | 0.9224 | 1.639E−08 | 192.4 | 97.4 |
| lipid phosphatase | GRMZM2G447433 | 0.9204 | 7.979E−10 | 216.4 | 107.2 |
| succinate dehydrogenase | GRMZM2G076524 | 0.8998 | 1.345E−09 | 1807.7 | 1129 |
| cytokinin-O-glucosyltransferase 2 | GRMZM2G363545 | 0.8642 | 1.727E−06 | 759.5 | 356.1 |
| polygalacturonate 4-alpha-galactonosyltransferase | GRMZM2G386971 | 0.8614 | 1.863E−05 | 218.5 | 129.2 |
| flavonol 3-O-glycosyltransferase; cytokinin biosynthesis | GRMZM2G111344 | 0.8592 | 1.893E−06 | 171.2 | 90 |
| glutaredoxin subgroup I; Grx_C3 | GRMZM2G004847 | 0.8169 | 6.697E−07 | 129.5 | 86 |
| tRNA - isopentenyl transferase IPT1 (cytokinin biosynthesis) | GRMZM2G097258 | 0.7952 | 3.735E−06 | 196.9 | 106.5 |
| WW oxidoreductase (alcohol dehydrogenase) | GRMZM2G018251 | 0.7419 | 8.582E−05 | 898.1 | 430.3 |
| polygalacturonate 4-alpha galactosyltransferase | GRMZM2G391000 | 0.7040 | 3.462E−05 | 244.9 | 152.2 |
| N-acetylglucosaminyltransferase (cytokinin) | GRMZM2G426275 | 0.7034 | 1.862E−07 | 142.6 | 86.6 |
| NADPH protochlorophyllide oxidoreductase | GRMZM2G073351 | 0.6914 | 1.343E−06 | 99.9 | 65.2 |
| glucan endo-1,3-beta-glucosidase 5 (cell wall) | GRMZM2G078566 | 0.6572 | 2.033E−06 | 103.1 | 63.9 |
| outer mitochondrial membrane protein porin | GRMZM2G055025 | 0.6170 | 2.273E−06 | 254.3 | 177.3 |
| glutathione peroxidase | GRMZM2G329144 | 0.6161 | 2.188E−04 | 1149.1 | 706.8 |
| S-adenosylmethionine decarboxylase proenzyme | GRMZM2G366392 | 0.5868 | 8.248E−03 | 585.5 | 384.2 |
| alcohol dehydrogenase | GRMZM2G051355 | 0.5769 | 5.079E−06 | 90.9 | 58.8 |
| NADP-dependent malic enzyme, chloroplastic precursor | GRMZM2G085019 | 0.5742 | 1.459E−03 | 545.1 | 466.7 |
| cytochrome c oxidoreductase | GRMZM2G107597 | 0.5711 | 3.520E−05 | 117.2 | 70.7 |
| cytokinin oxidase 3 | GRMZM2G167220 | 0.5596 | 2.432E−05 | 117.3 | 81 |

Table 6

Genes down-regulated in early msca1 versus fertile anthers. RNA extracted from fertile and msca1 whole anthers at the 200 m stage (just as the AR fate specification period is ending) were compared by microarray in duplicate (dye swap). Genes that were expressed two-fold lower in msca1 versus fertile have a log 2 ratio<−0.58 (p<0.05) and are expected to be either early AR genes (because this is the only differentiated cell type present in fertile, and it is absent in msca1), or just early anther genes that are turned off in msca1. Some genes just above the cutoff are listed because of their importance to either alternative metabolism or ROS handling. Included in this list are glutathione S-transferases, genes involved in alternative metabolism (including 2 genes from the glyoxylate cycle), and a number of hormone biosynthesis genes, most notably, the lipoxygenase protein mutated in the tassel seed1 loss of function mutant, in which no jasmonic acid is produced and the result is femininization of the tassel. Collectively, these data indicate that MSCA1-dependent specification of AR cells activates genes that are responsible for sex determination, ROS management, and organ identity.

TABLE 6

Downregulated in mscal vs fertile at 200 μm

| annotation/description | ProteinMatchID | log2 ratio | p-value | mscal intensity | fertile intensity |
|---|---|---|---|---|---|
| cytokinin-O-glucosyltransferase 2 | GRMZM2G041699 | −2.5513 | 1.091E−02 | 73.95 | 414.90 |
| sugar carrier protein C | GRMZM5G801949 | −2.0531 | 2.593E−04 | 201.42 | 593.17 |
| 1-aminocyclopropane-1-carboxylate synthase | GRMZM2G164405 | −1.7086 | 1.096E−02 | 70.85 | 272.67 |
| 1-deoxy-D-xylulose 5-phosphate synthase (isoprenoid biosynthesis) | GRMZM2G493395 | −1.7029 | 9.285E−03 | 275.74 | 762.93 |
| proline oxidase | GRMZM2G053720 | −1.5545 | 4.714E−04 | 2289.74 | 4789.97 |
| gibberellin 20 oxidase 2 | GRMZM2G099467 | −1.5378 | 5.118E−03 | 159.73 | 396.89 |
| thiazole biosynthetic enzyme 1-1, chloroplastic Precursor | GRMZM2G018375 | −1.3920 | 2.033E−02 | 407.60 | 1143.49 |
| NADP-dependent malic enzyme, chloroplastic Precursor | GRMZM2G085019 | −1.3571 | 1.045E−03 | 514.89 | 1280.96 |
| endo-1,4-beta-glucanase Cell (cell wall remodeling) | GRMZM2G147849 | −1.3102 | 2.025E−05 | 166.74 | 370.18 |
| 1-aminocyclopropane-1-carboxylate oxidase 1 | GRMZM2G013448 | −1.3086 | 4.265E−02 | 265.05 | 1392.82 |
| Beta-fructofuranosidase, cell wall isozyme Precursor | GRMZM2G139300 | −1.2865 | 1.610E−03 | 104.96 | 181.37 |
| glutathione S-transferase - GSTU6 | GRMZM2G330635 | −1.1997 | 3.112E−03 | 149.60 | 227.41 |
| gibberellin 2-beta-dioxygenase | GRMZM2G051619 | −1.1696 | 3.165E−02 | 637.94 | 1161.43 |
| phosphoenolpyruvate carboxylase kinase 3 (PEPCK) | GRMZM2G096753 | −1.0962 | 1.621E−04 | 699.39 | 1360.75 |
| cinnamyl alcohol dehydrogenase (CAD)(EC 1) | GRMZM5G844562 | −0.9915 | 8.686E−03 | 198.10 | 309.35 |
| glucan endo-1,3-beta-glucosidase 7 | GRMZM5G805609 | −0.9862 | 8.619E−03 | 179.31 | 275.28 |
| lipoxygenase oxidoreductase activity | GRMZM2G156861 | −0.9183 | 2.746E−02 | 210.05 | 481.99 |
| secretion - in golgi, responsible for secretion | GRMZM2G132898 | −0.8321 | 9.107E−03 | 236.71 | 349.77 |
| 6-phosphofructokinase 2 | GRMZM2G132069 | −0.8302 | 5.305E−03 | 417.74 | 638.72 |
| S-adenosylmethionine decarboxylase proenzyme | GRMZM2G125635 | −0.8178 | 4.294E−02 | 2591.88 | 5126.82 |
| cytosolic glyceroldehyde-3-phosphate dehydrogenase | GRMZM2G176307 | −0.8017 | 1.925E−02 | 76.35 | 150.80 |
| glucan endo-1,3-beta-glucosidase 7 | GRMZM2G046101 | −0.7727 | 8.261E−03 | 583.66 | 866.33 |
| transferase, transferring glycosyl groups | GRMZM2G149024 | −0.7254 | 7.771E−03 | 1107.45 | 1722.66 |
| outer mitochondrial membrane protein porin | GRMZM2G059937 | −0.7212 | 7.939E−03 | 117.96 | 197.64 |
| glutamate dehydrogenase (GDH)(EC 1.4.1.3) | GRMZM2G178415 | −0.6901 | 4.671E−03 | 148.17 | 201.28 |
| tassel seed1 (lipoxygenase) | GRMZM2G104843 | −0.6492 | 4.192E−02 | 62.31 | 88.83 |
| glutaredoxin subgroup I - Grx_C4 | GRMZM2G172357 | −0.6343 | 3.209E−03 | 925.91 | 1310.44 |
| S-adenosylmethionine decarboxylase proenzyme | GRMZM2G366392 | −0.5936 | 5.201E−03 | 410.37 | 542.65 |
| myristoyl-acyl carrier protein thioesterase | GRMZM2G406603 | −0.5874 | 5.150E−02 | 539.12 | 778.91 |
| phosphoenolpyruvate carboxylase kinase 4 (PEPCK) | GRMZM2G049541 | −0.5773 | 3.695E−02 | 5073.81 | 6819.54 |
| 3-isopropylmalate dehydrogenase | GRMZM2G120857 | −0.5423 | 1.585E−02 | 1674.58 | 2241.53 |

Example 9

Just-Committed Germinal Cells are Hypoxic and Precociously Express Meiotic Genes Multicellular sexual life cycles initiate with the dedication of cells to a meiotic fate. Such germinal cells commonly conduct several mitoses preceding meiotic entry, however relatively little is known about what characterizes meiotic commitment in these initially fated cells. To redress this, a precisely staged cohort of germinal cells was isolated from maize anthers and compared to somatic niche layers, just 36 hours following their shared derivation from somatic stem cells and six days prior to meiosis. Microarray hybridization provided the earliest transcriptomes of such cell types for any organism: 2529 germinal and 4551 somatic transcripts were either specific (ON/OFF) or differentially regulated (UP/DOWN). There is strong support for the concept that plant germinal cells are hypoxic and curtail reactive oxygen through alternative energy-generating pathways, circumventing mitochondrial respiration. The pre-meiotic set included 116 genes previously classified as meiosis-specific, along with ribosomal components, RNA helicases, pumilio translational repressors and other genes involved in post-transcriptional gene regulation. Additionally, three novel ARGONAUTE genes putatively involved in genome surveillance or chromatin remodeling characterized the germinal cells. These findings establish new properties of just-specified germinal cells, including precocious expression of meiosis-associated functions, and implicate new roles for transcriptional and translational control defining the commitment to meiosis in plants.

A fundamental difference between the kingdoms is the existence of a germ-line in animals and its absence in plants. In most animal phyla, germ-line stem cells are sequestered during early embryogenesis and dedicated to continuous gamete production in adulthood. Male reproductive organs resemble an assembly line, with diploid germ-line stem cells at one end, haploid gametes at the other, and a continuous developmental gradient in between. In contrast, most plants and fungi produce cohorts of germinal cells late in life from a pool of somatic stem cells. In anthers, the male reproductive organ of seed plants, pluripotent floral stem cells rapidly acquire a germinal or somatic fate, exhausting the entire stem cell reservoir. In maize this process yields about 12 archesporial (AR) initials per anther lobe. These enlarge and cycle through 3-4 mitoses before synchronously initiating meiosis; the somatic cells form three layers that provide nutritional and structural support (FIG. 20a).

Transcriptome profiling has illuminated aspects of anther development at pre-meiotic, meiotic, and post-meiotic stages in rice, maize, and *Arabidopsis*. Mixed populations of meiotic cells and male gametophytes have been profiled, however, no studies have analyzed isolated, just-committed, pre-meiotic cells, reflecting their inaccessibility within flowers. By exploiting large anther size, reliable staging, and a bulls-eye organ structure that facilitates laser-capture microdissection (LCM) (FIG. 20b,c), we directly compared maize anther germinal and somatic transcriptomes on day three of anther development, 36 hours post-specification. Because both germinal and subepidermal somatic cells originate from the Layer2-derived (L2-d) pluripotent cells (FIG. 20a) and have, at most, undergone one mitotic division since specification, transcriptomic differences represent changes fundamental to setting germinal and somatic fate from common stem cell progenitors.

Figure 21:
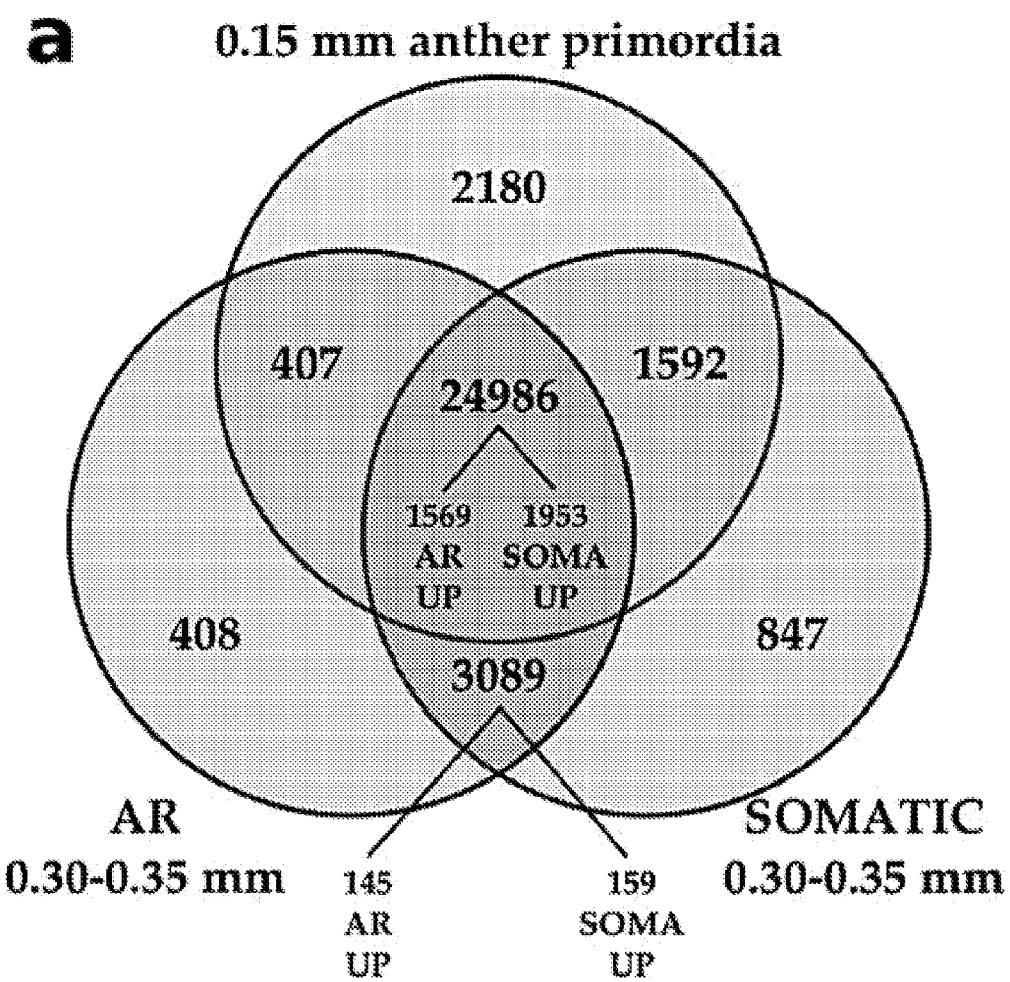
FIG. 21. VENN diagram comparisons of LCM-dissected tissues contrasted with anther primordia, and two alternative metabolic pathways. (a) Counts denote presence/absence in indicated samples. Among the 28075 transcripts shared between germinal (AR) and somatic tissues, 3826 (1569+1953+145+159) were significantly differentially expressed. (b,c) Alternative metabolic pathways adapted from Pathway Tools/maizecyc ("maizecyc." followed by "maizegdb.org") showing transcripts for enzymes that are AR-specific or -enriched highlighted in bronze. Both of these pathways start with pyruvate diverted from the TCA by pyruvate dehydrogenase kinase2, which is highly enriched in germinal cells. (b) Production of ethanol and $NAD^+$ from pyruvate by pyruvate decarboxylase and alcohol dehydrogenase. (c) Production of lactate and $NAD^+$ from pyruvate by malate dehydrogenase.

Maize AR cell expansion signifying fate acquisition initiates in late day one anthers, but the only AR marker, *Sporocyteless* of *Arabidopsis*, is not expressed until the equivalent of maize day five. To identify genes critical to reproductive fate acquisition, the LCM-collected samples were first contrasted with anther primordia, which contain the L2-d stem cells in addition to presumptive vasculature and epidermis (FIG. 20a). On day three, 1280 of the 4344 newly expressed transcripts were above the median representing abundant stage-specific markers (FIG. 21a); 71% of these were common to AR and somatic tissues. Additionally, 1999 transcripts present in primordia were quenched in one tissue, and 2180 were absent from both. In the direct tissue comparison, 815 and 2439 transcripts were exclusive to the germinal and somatic tissues, respectively, and a further 1714 AR and 2112 somatic transcripts were differentially expressed (log fold change>0.58, p<0.05); 92.1% of these cell-specific transcripts were also found in primordia (FIG. 21a). Collectively these data illustrate massive transcriptional reprogramming during reproductive fate acquisition; 78% of changes refine the transcriptional palette of anther primordia rather than activate new gene expression.

Figure 22:
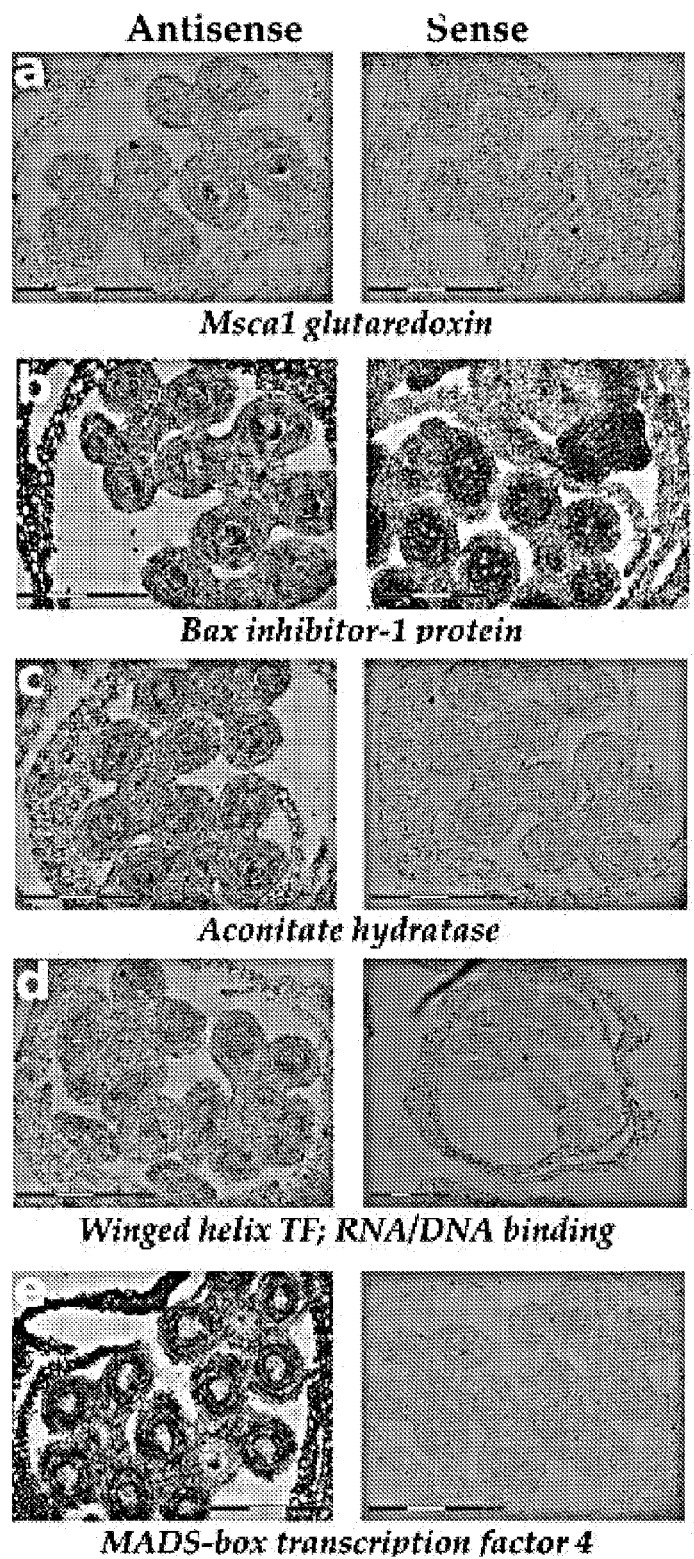
FIG. 22. (a-e) RNA In situ hybridizations for the genes: (a) Msca1 glutaredoxin; (b) Bax inhibitor-1 protein; (c) Aconitate hydratase; (d) Winged helix TF; RNA/DNA binding; and (e) MADS-box transcription factor 4.
Figure 23:
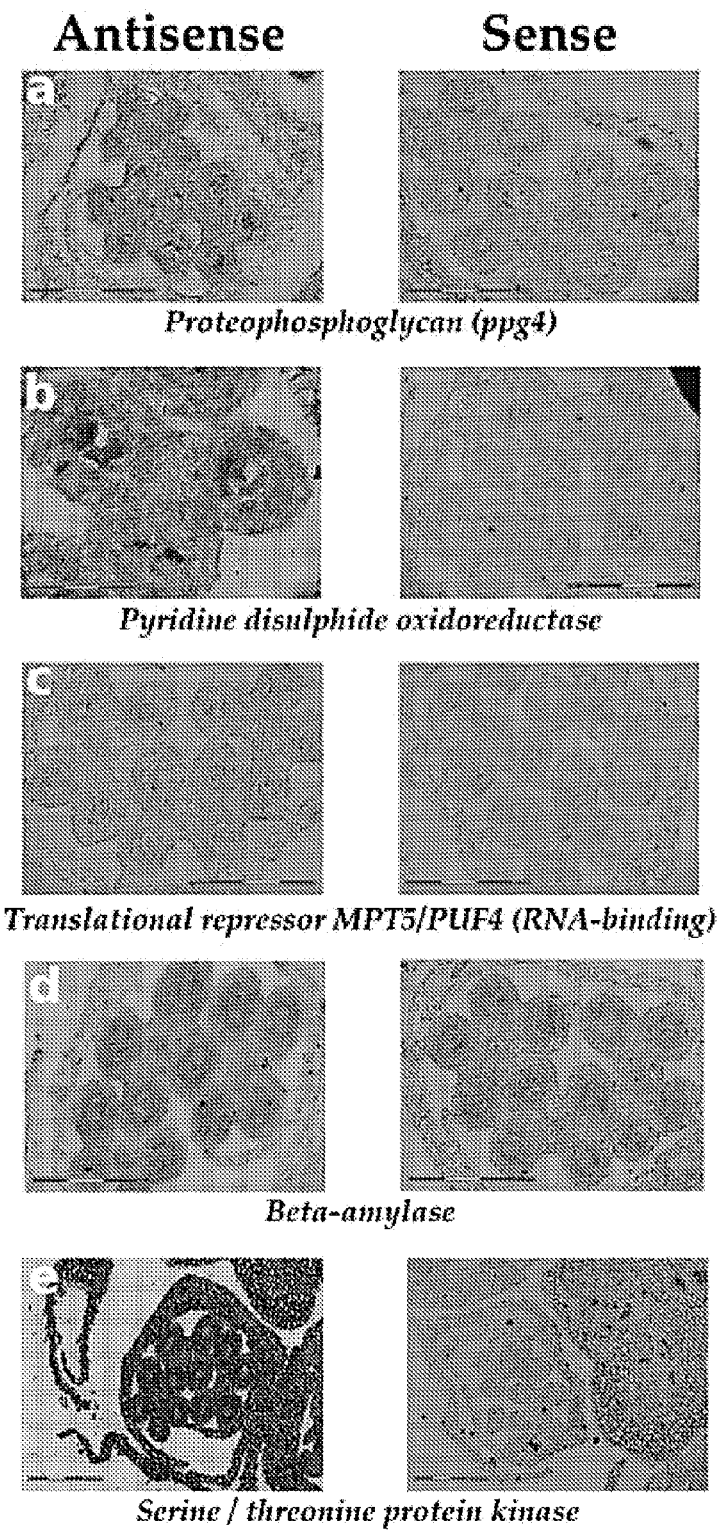
FIG. 23. In situ hybridizations of germinal (a-c) and somatic (d-j) cell-specific candidate markers. The antisense probes hybridize to sense transcripts, while the sense probes hybridize to antisense transcripts, if they are present, or otherwise serve as a negative control. (a) Proteophosphoglycan (ppg4) has no defined role, but it is the third most highly enriched AR transcript and is clearly specific to germinal cells. The sense probe gave no signal. (b) Pyridine disulphide osidoreductase. The sense probe gave no signal. (c) Translational repressor MPT5/PUF4 (RNA-binding). The sense probe gave no signal. (d) The beta-amylase transcript is clearly specific to the secondary parietal layer (SPL), while the sense control probe hybridized to both AR and SPL cells and lightly to the endothecium, indicative of antisense transcription at this locus in all L2-d cells. (e) The serine/threonine protein kinase is highly enriched in SPL, endothecium and epidermis, while the sense control probe gave no signal. (f) The MADS-box transcription factor antisense probe hybridized to SPL and endothecium as expected from categorization of this transcript as somatic-specific, while the sense probe detected antisense transcription in AR and, to a lesser extent, SPL cells. (g) A similar reciprocal phenomenon was found for the antisense and sense probes of the protein tyrosine phosphatase (PTPLA). (h-j) The final three tested transcripts encoding transcription factors confirmed their classification as somatic markers, while the sense probes either indicated (h,i) epidermal antisense transcription or (j) nonspecific accumulation of probe in the gaps between the rectilinear epidermal and endothecial cells.niche.
Figure 23:
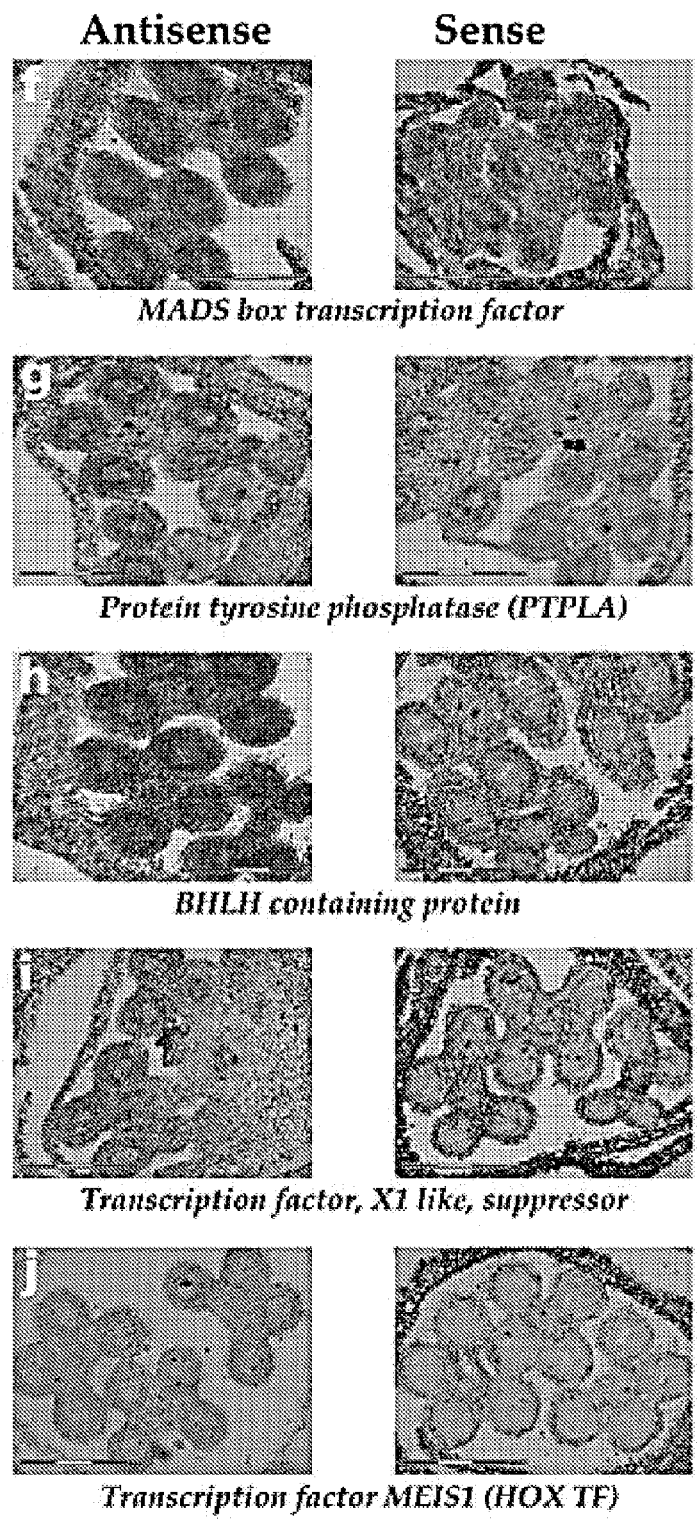
Figure 24:
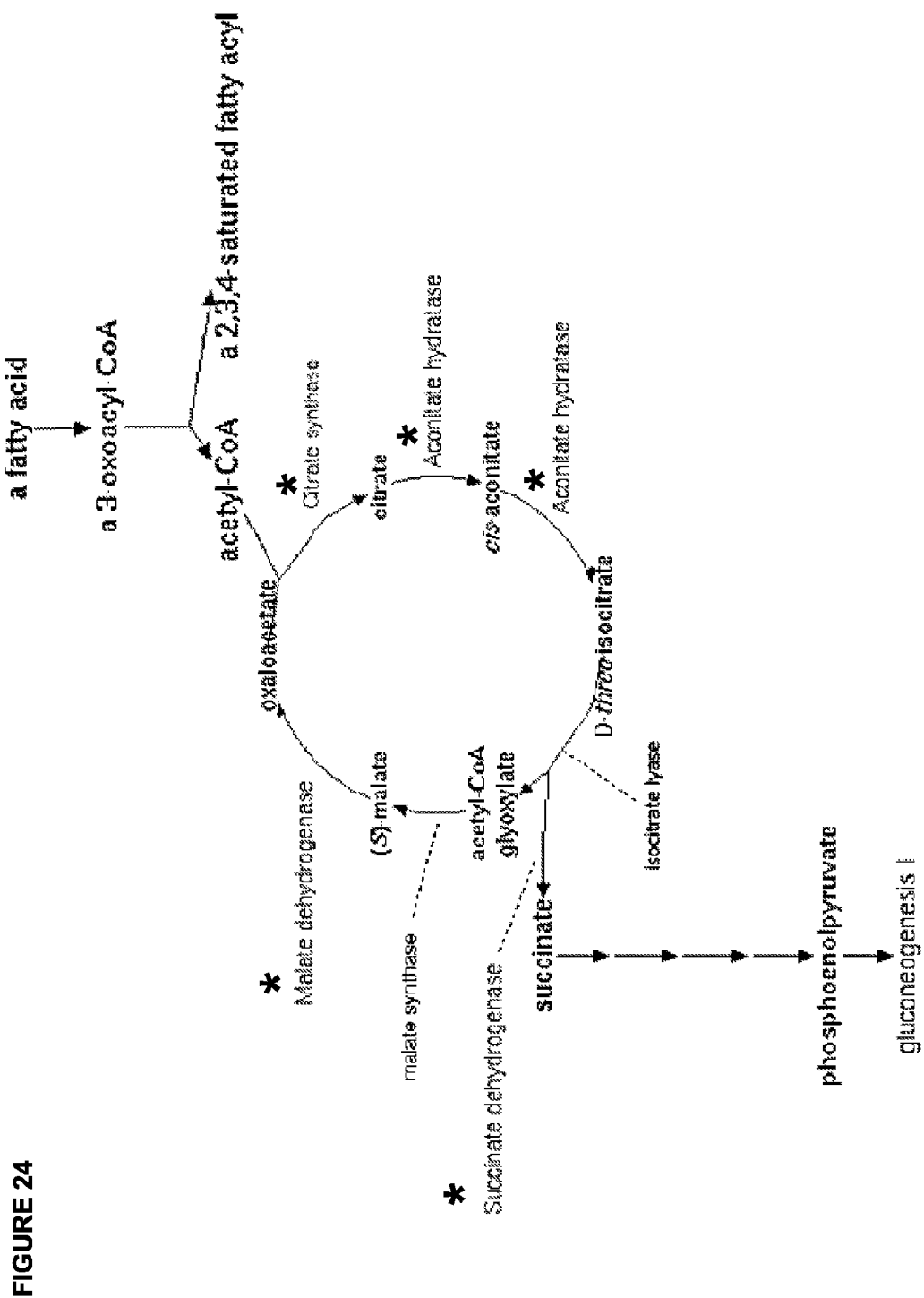
FIG. 24. The cytosolic glyoxylate shunt pathway converting fatty acids to sugar, as adapted from Pathway Tools/maizecyc ("maizecyc." followed by "maizegdb.org"). Transcripts for enzymes that are AR specific or -enriched are marked with asterisks.
Figure 25A:
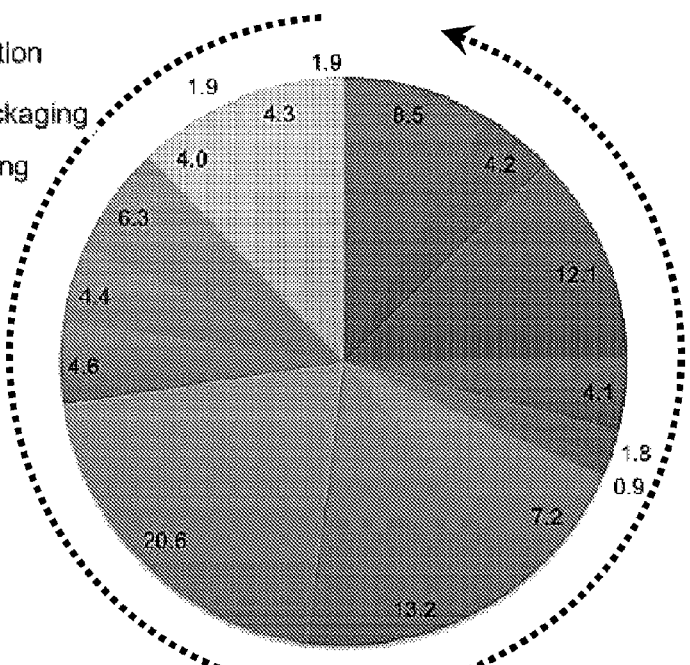
FIG. 25. Distribution of GO terms within AR and somatic sets (2529 and 4551 genes, respectively). (a) The AR cells are enriched in the categories of RNA binding and RNP biogenesis (4.2% of all terms versus 1.8% for the somatic cells), and translation (including ribosomal proteins this accounts for 12.1% of all terms versus 1.4% for the somatic cells). (b) Somatic tissues were enriched for catalytic activity (10.7% of all terms versus 4.1% for the AR cells), cell communication (4.0% of all terms versus 1.8% for the AR cells), and transcriptional regulation including DNA polymerase II subunits and DNA binding transcription factors (9.2% of all terms versus 4.0% for the AR cells).
Figure 25:
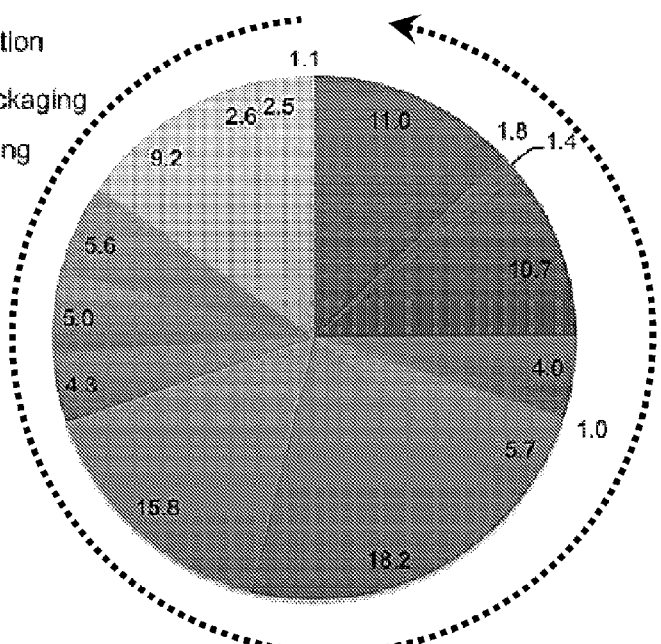

Filtering for high enrichment and abundance (log fold change>2, expression>median) we identified 49 (3 newly expressed) germinal and 244 (16 new) somatic transcripts as promising cell- and stage-specific markers. A subset was selected for validation of cell-type specificity by qRT-PCR ($^{52}/_{59}$ confirmed) (Table 8) and RNA in situ hybridization ($^{15}/_{17}$ confirmed, 2 gave no signal). Six probes that hybridized to AR cells are the first monocot and earliest plant germinal cell markers reported (FIG. 22a-c and FIG. 23a-c), including the glutaredoxin Msca1 critical for hypoxia-mediated AR specification (FIG. 22a), the anti-apoptotic Bax inhibitor-1 (FIG. 22b), and the glyoxylate cycle enzyme aconitate dehydratase (FIG. 22c). One AR candidate hybridized to both AR and secondary parietal layer (SPL) cells (FIG. 22d). Successful hybridizations confirmed eight somatic markers (FIG. 22e and FIG. 23d-j), including a beta-amylase specific to the bipotent SPL (FIG. 23d), the first marker for this cell type that yields the middle layer and tapetum. Seven out of fifteen sense probes gave a patterned signal (FIG. 22b and FIG. 23d,f-j). Sense and antisense hybridization patterns were complimentary or partially overlapping, supporting a hypothesis that antisense transcripts are suppressors, facilitating rapid cell differentiation.

We demonstrate that germinal cells utilize multiple routes for generating ATP and reducing power without respiration. Germinal cells were significantly enriched in phosphoenolpyruvate (PEP) carboxylase kinase, which is regulated by hypoxia and phosphorylates PEP carboxylase, also AR-enriched, to activate cytosolic ATP production. The germinal set also included pyruvate dehydrogenase kinase2 diverting pyruvate away from the citric acid cycle (TCA) towards other AR-specific or -enriched enzymes that convert it to ethanol (pyruvate decarboxylase and alcohol dehydrogenase) or lactate (malate dehydrogenase) and regenerate $NAD^+$ (FIG. 21b,c). Additionally, four of the six components of the glyoxylate shunt converting lipids to sugar were enriched in germinal cells (FIG. 22). Both somatic and germinal sets included TCA and electron transport components. Germinal cells prioritize ROS cleanup by expressing superoxide dismutase, many thioredoxins, and factors critical to regenerating glutathione. The emphasis on non-mitochondrial ATP production and ROS clearance highlights the importance of genome integrity to reproductive success, and indicates that hypoxia is not only a mechanism of AR fate specification, but also a persistent physiological feature of the reproductive niche.

Having established morphological and now molecular and metabolic properties of pre-meiotic cells, we asked whether these cells were preparing for meiosis. AR cells were specifically enriched for 34.3% ($^{102}/_{297}$) of genes assigned to maize anther meiotic progression, along with 14 others with defined roles in meiosis (Table 9). These included genes responsible for chromosomal pairing, synapsis, and recombination, including DYAD/SWI1, AFD1, PHS1, homologs of RAD51 and ZYP1, and nine transcripts for DNA repair or double stranded break formation. Therefore, meiotic factors are synthesized just following germinal specification, ~3 mitoses prior to canonical "pre-meiosis", challenging current dogma that the meiosis decision point is after pre-meiotic S phase. Precocious expression may permit gradual dilution of mitotic chromatin components during the AR transit amplifying divisions, a hypothesis gaining support for the animal germ-line.

An alternative explanation is that some mRNAs encoding meiotic proteins are stored pre-meiotically, perhaps in the AR cells' conspicuous nucleoli, known sites of ribonucleoprotein (RNP) complex biogenesis and function. RNP-based mRNA protection and storage is a well-established aspect of animal germ-lines. While RNPs have been described in plants, reproductive roles remain undefined. Our data indicate that plant germinal cells express numerous transcripts encoding RNP complex components (6 germinal versus 0 somatic), RNA helicases (14 versus 2), PUF/Pumilio translational repressors (5 versus 0), ribosomal proteins (97 versus 14), and translation initiation or elongation factors (18 versus 6). Collectively these transcripts account for 16.3% of AR cell GO terms, compared to 3.2% of somatic cell GO terms. The abundance of ribosomal components suggests that germinal cells are acquiring the ability to boost translational capacity or build functionally distinct ribosomes. These findings may explain how maize meiocytes constitute just 1.5% of anther cells but contain 20% of anther RNA, much of which will contribute to haploid cell cytoplasm (either as stored RNA or translated protein) following meiosis. Although the mechanism(s) underlying germinal fate specification are widely divergent among animal phyla and plants, RNA-binding proteins are a common feature of pre-meiotic cells.

AR cells also are enriched for numerous genes that affect epigenetic transformations required for reproduction. This is of interest because the timing of de novo DNA methylation, transposable element suppression, and epigenetic reprogramming during the germinal progression is not well understood. Maize has 18 AGO proteins, and we find germinal cells are enriched for five, including AGO105 and AGO121, which cluster with AtAGO4/6/9 involved in RNA-directed DNA methylation. Together with IDN2 and DRD1, genes key to non-CG methylation and also in the AR set. AR cells also precociously express two maize homologs of OsMEL1 (AGO5a and AGO5b) regulating meiotic chromosome condensation. The fifth-most enriched germinal cell marker is the highly expressed AGO18a, a strong candidate for interaction with a non-coding class of phased siRNAs (termed phasiRNAs) because of their contemporaneous expression in anthers and specificity to grasses.

TABLE 7

Counts of differentially expressed transcripts, sorted for expression intensity by quartile (columns) and log-fold change between samples (rows).

| | | Expression Intensity by Quartile | | | | |
|---|---|---|---|---|---|---|
| | | 1st | 2nd | 3rd | 4th | total |
| Germinal | | | | | | |
| AR ON, SOMA OFF | | 758 | 53 | 4 | 0 | 815 |
| Differential | <1.0 | 1 | 126 | 364 | 757 | 1248 |
| Log ratio | 1.0-1.5 | 0 | 11 | 87 | 223 | 321 |
| | 1.5-2.0 | 0 | 0 | 38 | 58 | 96 |
| | 2.0-3.0 | 0 | 0 | 8 | 36 | 44 |
| | >3.0 | 0 | 0 | 0 | 5 | 5 |
| | total | 759 | 190 | 501 | 1079 | 2529 |
| Somatic | | | | | | |
| SOMA ON, AR OFF | | 2097 | 309 | 28 | 5 | 2439 |
| Differential | <1.0 | 0 | 144 | 421 | 534 | 1099 |
| Log ratio | 1.0-1.5 | 0 | 12 | 235 | 260 | 507 |
| | 1.5-2.0 | 0 | 0 | 79 | 183 | 262 |
| | 2.0-3.0 | 0 | 0 | 6 | 199 | 205 |
| | >3.0 | 0 | 0 | 0 | 39 | 39 |
| | total | 2097 | 465 | 769 | 1220 | 4551 |

TABLE 8

Confirmation of cell-type specificity of high quality markers with qRT-PCR.

| | Probe ID | Protein ID | array log fold change | qRT AR Ct | qRT Somatic Ct | qRT log fold change | Validated? | in situ expression? | antisense probe localization | sense probe localization |
|---|---|---|---|---|---|---|---|---|---|---|
| AR Markers (Description) | | | | | | | | | | |
| Cyanase (control gene for qRT-PCR normalization) | N/A | [CONTROL] | N/A | 25.19 | 25.84 | N/A | N/A | N/A | N/A | N/A |
| Proteophosphoglycan ppg4 | 27996 | GRMZM2G032528 | 3.292 | 22.02 | 24.98 | 3.070 | yes | yes (FIG. S1a) | AR | no signal |
| Leafbladeless1 (supressor of gene silencing 3) | 6692 | GRMZM2G163514 | 3.09 | 27.94 | 30.18 | 2.176 | yes | not done | N/A | N/A |
| Argonaute18a (AGO18a) | 24515 | GRMZM2G105250 | 3.013 | 23.92 | 29.48 | 4.535 | yes | not done | N/A | N/A |
| Ubiquitin 10 | 20294 | GRMZM2G087870 | 2.782 | 25.85 | 28.43 | 2.671 | yes | not done | N/A | N/A |
| Glycosyltransferase | 39220 | GRMZM2G140107 | 2.566 | 30.62 | 32.73 | 1.782 | yes | no signal | N/A | N/A |
| Bax1 inhibitor-1 family | 27254 | GRMZM2G095898 | 2.497 | 28.18 | 30.6 | 2.433 | yes | yes (FIG. 3b) | AR | AR & SPL (strong) |
| RNA-binding protein Sam68 and related KH proteins | 28011 | AC218972.3_FGT007 | 2.408 | 30.62 | 31.79 | 1.064 | yes | not done | N/A | N/A |
| Molecular chaperone (DnaJ superfamily) | 35081 | GRMZM2G029385 | 2.217 | 31.03 | 32.83 | 1.646 | yes | not done | N/A | N/A |
| Pyridine disulfide oxidoreductase | 36685 | GRMZM2G563190 | 2.143 | 28.04 | 30.83 | 2.558 | yes | yes (FIG. S3b) | AR | no signal |
| Prohibitin | 8540 | GRMZM2G410710 | 2.028 | 30.56 | 32.24 | 1.556 | yes | not done | N/A | N/A |
| Ca2+/calmodulin-dependent protein phosphatase | 24368 | GRMZM2G125838 | 2.025 | 29.8 | 32.42 | 2.414 | yes | not done | N/A | N/A |

TABLE 8-continued

Confirmation of cell-type specificity of high quality markers with qRT-PCR.

| | Probe ID | Protein ID | array log fold change | qRT AR Ct | qRT Somatic Ct | qRT log fold change | Validated? | in situ expression? | antisense probe localization | sense probe localization |
|---|---|---|---|---|---|---|---|---|---|---|
| Emp24/gp25L/p24 family of membrane trafficking proteins | 26591 | GRMZM2G134502 | 2.016 | 33.86 | 33.22 | −0.556 | no | not done | N/A | N/A |
| Alcohol dehydrogenase, class III | 6913 | GRMZM2G135526 | 1.97 | 32.07 | 33.47 | 1.345 | yes | not done | N/A | N/A |
| Inositol polyphosphate multikinase, ARGR transcriptional component | 4288 | GRMZM2G368799 | 1.956 | 30.16 | 31.73 | 1.454 | yes | not done | N/A | N/A |
| Transcription factor, subunit of SRB subcomplex of RNA polymerase II | 714 | GRMZM2G110500 | 1.87 | 28.61 | 30.13 | 1.406 | yes | not done | N/A | N/A |
| Involved in cell differentiation/sexual development | 12943 | AC191251.3_FGT005 | 1.826 | 29.35 | 30.63 | 1.350 | yes | not done | N/A | N/A |
| SAUR-like auxin-responsive; enriched in AR always | 8105 | GRMZM2G466229 | 1.586 | 34.65 | 0 | ON/OFF | yes | not done | N/A | N/A |
| Alkyl hydroperoxide reductase, thioredoxin peroxidase | 30360 | GRMZM5G864335 | 1.512 | 26.66 | 28.27 | 1.700 | yes | not done | N/A | N/A |
| RNA-binding translational regulator IRP (aconitase hydratase) | 33303 | GRMZM2G176397 | 1.476 | 29.59 | 30.78 | 1.245 | yes | yes (FIG. 3c) | AR | no signal |
| LRR protein, may contain F-box | 33129 | GRMZM2G155849 | 1.384 | 26.64 | 28.42 | 1.795 | yes | not done | N/A | N/A |
| MAM33, mitochondrial matrix glycoprotein | 23695 | GRMZM2G085932 | 1.292 | 27.6 | 28.82 | 1.293 | yes | no signal | N/A | N/A |
| Glucose-6-phosphate & PEP antiporter | 16225 | GKMZM2G047404 | 1.291 | 34.28 | 0 | ON/OFF | yes | not done | N/A | N/A |
| AGO121 | 41571 | GRMZM2G589579 | 1.289 | 23.05 | 25.99 | 2.358 | yes | not done | N/A | N/A |
| Homology to IDN2 (involved in de novo 2), dsRNA-binding protein involved in RdDM | 36073 | GRMZM2G096367 | 1.286 | 27.35 | 30.01 | 2.653 | yes | not done | N/A | N/A |
| Translational repressor MPT5/PUF4 & related RNA-binding proteins | 29573 | GRMZM2G160279 | 1.184 | 27.77 | 28.99 | 1.192 | yes | yes (FIG. S1c) | AR (weak) | no signal |
| Predicted E3 ubiquitin ligase | 7622 | GRMZM2G423956 | 1.181 | 33.6 | 32.57 | −0.943 | no | not done | N/A | N/A |
| Winged-helix DNA-binding TF; RNA binding | 10216 | GRMZM2G140339 | 1.117 | 27.13 | 28.81 | 1.731 | yes | yes (FIG. 3d) | AR & SPL | no signal |
| Meristem disorganization1; stem cell maintenance via DNA repair | 23532 | GRMZM2G002910 | 1.007 | 33.48 | 32.5 | −0.916 | no | not done | N/A | N/A |
| RNA-dependent RNA polymerase 1 (RDR1) | 4610 | GRMZM2G481730 | 0.945 | 26.58 | 28.33 | 1.256 | yes | not done | N/A | N/A |
| Argonaute5a (AGO5a); OsMEL1-homolog | 9040 | GRMZM2G461936 | 0.923 | 25.47 | 27.13 | 1.642 | yes | not done | N/A | N/A |
| Histone deacetylase complex, catalytic component HDA1 | 28981 | GRMZM2G005205 | 0.864 | 29.65 | 30.86 | 1.281 | yes | not done | N/A | N/A |
| Msca1 (male sterile converted anther1) (glutaredoxin) | N/A | N/A (not on array) | N/A | not tested | not tested | N/A | no | yes (FIG. 3a) | AR | no signal |
| Somatic markers (Description) | | | | | | | | | | |
| Mevalonate pyrophosphate decarboxylase | 13031 | GRMZM2G095798 | 2.678 | 32.52 | 27.02 | 6.089 | yes | not done | N/A | N/A |
| MADS box transcription factor | 2978 | GRMZM2G359952 | 2.639 | 33.42 | 28.55 | 5.286 | yes | yes (FIG. S1f) | SPL & EN | AR |
| Transcription factor, bHLH-domain | 13965 | GKMZM2G139371 | 2.557 | 32.56 | 30.55 | 3.134 | yes | yes (FIG. S1h) | SPL & EN | EPI & EN |
| Glycosyl endocellulase | 13880 | GRMZM2G165633 | 2.455 | 0 | 34.45 | ON/OFF | yes | not done | N/A | N/A |

TABLE 8-continued

Confirmation of cell-type specificity of high quality markers with qRT-PCR.

| | Probe ID | Protein ID | array log fold change | qRT AR Ct | qRT Somatic Ct | qRT log fold change | Validated? | in situ expression? | antisense probe localization | sense probe localization |
|---|---|---|---|---|---|---|---|---|---|---|
| Transcription factor, Myb superfamily | 5001 | GRMZM2G000818 | 2.419 | 0 | 34.45 | ON/OFF | yes | not done | N/A | N/A |
| Methylenetetrahydrofolate reductase protein | 24477 | GRMZM2G053720 | 2.414 | 29.76 | 25.22 | 5.557 | yes | not done | N/A | N/A |
| Kinase | 24709 | GRMZM5G800211 | 2.413 | 34.92 | 31.61 | 3.856 | yes | not done | N/A | N/A |
| Saposin-related | 44921 | GRMZM5G877259 | 2.342 | 32.93 | 28.41 | 5.223 | yes | not done | N/A | N/A |
| Beta-amylase | 18382 | GRMZM2G450125 | 2.315 | 31.84 | 28.82 | 3.491 | yes | yes (FIG. S1d) | SPL | AR, SPL, & EN |
| Serine/threonine protein kinase | 33159 | GRMZM2G086577 | 2.307 | 34 | 28.65 | 5.957 | yes | yes (FIG. S1e) | SPL, EN, & EPI | no signal |
| Transcription factor MEIS1 (HOX domain containing) | 31491 | GRMZM2G154641 | 2.119 | 32.83 | 30.18 | 3.485 | yes | yes (FIG. S1j) | SPL, EN | EPI & EN |
| Kelch repeat-containing proteins | 24060 | GRMZM2G038152 | 2.115 | 31.65 | 28.89 | 3.614 | yes | not done | N/A | N/A |
| Protein tyrosine phosphatase-like protein PTPLA | 8204 | GRMZM2G151087 | 2.092 | 28.48 | 25.69 | 3.678 | yes | yes (FIG. S1g) | SPL (strong), EN, & EPI | AR & SPL |
| RNA-binding translational regulator IRP (aconitase superfamily) | 31880 | GRMZM5G858454 | 1.923 | 25.88 | 24.22 | 2.506 | yes | not done | N/A | N/A |
| Serine/threonine protein kinase | 13743 | GRMZM5G871520 | 1.848 | 29.49 | 27.01 | 3.488 | yes | not done | N/A | N/A |
| Calmodulin-binding | 17791 | GRMZM5G828487 | 1.781 | 31.26 | 31.98 | 0.379 | no | not done | N/A | N/A |
| Duf593-containing protein | 12983 | GRMZM2G035839 | 1.667 | 32.55 | 30.04 | 3.472 | yes | not done | N/A | N/A |
| D-3-phosphoglycerate dehydrogenase, | 38310 | GRMZM2G073814 | 1.655 | 30.48 | 28.36 | 3.018 | yes | not done | N/A | N/A |
| Ralf-like; (rapid alkalinization factor) | 7046 | GRMZM2G171394 | 1.615 | 31.69 | 28.89 | 3.731 | yes | not done | N/A | N/A |
| Chitinase | 38372 | GRMZM2G090441 | 1.563 | 30.44 | 28.77 | 2.774 | yes | not done | N/A | N/A |
| SMAD/FHA (forkhead) domain-containing protein; chloroplast | 39018 | GRMZM2G172021 | 1.38 | 0 | 0 | N/A | no | not done | N/A | N/A |
| Lil3, light harvesting complex (LHC) | 10276 | GRMZM2G477236 | 1.343 | 32.87 | 33.49 | 0.379 | no | not done | N/A | N/A |
| Sphingolipid fatty acid hydroxylase | 41310 | GRMZM2G038964 | 1.29 | 28.98 | 28.88 | 1.084 | yes | not done | N/A | N/A |
| MADS box TF | 6868 | GRMZM2G099522 | 1.282 | 25.67 | 24.77 | 1.895 | yes | not done | N/A | N/A |
| MADS box TF | 25416 | GRMZM2G097059 | 1.269 | 25.88 | 23.8 | 3.208 | yes | yes (FIG. 3e) | SPL (strong), EN, & EPI | no signal |
| Glutaredoxin-related protein | 22544 | GRMZM2G041809 | 1.217 | 0 | 0 | N/A | no | not done | N/A | N/A |
| Transcription factor, X1 like, supressor | 4136 | GRMZM2G020187 | 1.204 | not tested | not tested | N/A | N/A | yes (FIG. S1i) | SPL, EN, & EPI | EPI |
| Argonaute10a (AGO10a) | 28292 | AC189879.3_FGT003 | 1.172 | 26.14 | 24.47 | 2.489 | yes | not done | N/A | N/A |
| Double-stranded RNA-binding domain-containing protein; Dicer-like4 | 23966 | GRMZM2G160473 | 0.598 | 29.13 | 28.06 | 1.828 | yes | not done | N/A | N/A |

For Table 8, the reactions were performed on cDNA made from the same tissue samples as were used for the microarray. qRT-PCR confirmed cell-type specificity for 28/31 germinal transcripts, including two that were classified by qRT-PCR as ON in AR cells and OFF (no amplification) in somatic cells. Six out of nine AR markers tested by in situ hybridization gave the expected AR-localized pattern, one hybridized to both AR and SPL. A further 24/28 somatic transcripts were confirmed, including two that were classified by qRT-PCR as ON in somatic and OFF in AR cells. Eight out of eight somatic markers tested by RNA in situ hybridization gave the expected somatic-specific pattern. In the "validated?" column, a 'yes' indicated confirmation of cell-type specificity by qRT-PCR. The requirements for confirmation was that the log 2 ratio of Ct values for the two samples had to be >0.58 in the expected direction. This calculation was made from Ct values that were adjusted for primer efficiency using PCR miner ("www." followed by "ewindup.info" followed by "/miner/version2/") and adjusted for starting cDNA amounts by comparison with the housekeeping gene cyanase. All primers were designed to bridge introns and all passed a gDNA and cDNA test with the expected intron size differences between amplified products analyzed by gel electrophoresis. Also indicated on the table are the array log-fold change values for comparison to qRT-PCR results, and the RNA in situ hybridization result, if that experiment was performed for the given transcript.

Table 9. These genes have defined functions in meiosis or were assigned to meiotic progression7 by differential expression in both ameiotic1-pra1 and ameiotic1-489 alleles in meiotic anthers (1.5 mm anther length). The ameiotic1-1 mutant and most other ameiotic1 (am1) alleles in maize have a dramatic phenotype: AR cells look and act normal until meiosis, when they conduct mitosis instead. Am1-pra1 permits meiotic entry but pollen mother cells arrest at the leptotene/zygotene transition, defining the roles of the AMEIOTIC1 protein in two distinct steps of meiosis.

TABLE 9

AR-enriched or -specific transcripts involved in meiosis.

| AR-characteristic transcripts involved in meiosis (Description) | Probe ID | Protein ID | Log-fold change | AR Avg Intensity | Somatic Avg Intensity | Ratio |
| --- | --- | --- | --- | --- | --- | --- |
| Leafbladeless1, Clone 370919 mRNA sequence | 6692 | TC299943 | 3.09 | 1342.4 | 153.6 | 8.74 |
| AGO18a | 24515 | GRMZM2G105250 | 3.013 | 1306.2 | 137.2 | 9.52 |
| FOG: RRM domain, CID11, nucleic acid binding | 22809 | GRMZM2G173428 | 2.898 | 28279 | 3849.1 | 7.35 |
| Chorismate mutase | 29929 | GRMZM2G124365 | 2.722 | 5184.8 | 646.9 | 8.01 |
| EGG APPARATUS-1 protein | 20458 | GRMZM2G157505 | 2.549 | 2434 | 343.8 | 7.08 |
| GTPase Rab6/YPT6/Ryh1, small G protein superfamily | 6678 | TC284111 | 2.391 | 587.6 | 101.7 | 5.78 |
| Porin/voltage-dependent anion-selective channel protein, alpha amylase activity, carbohydrate metabolism, calcium binding | 16651 | TC309747 | 2.255 | 304.6 | 66 | 4.62 |
| Molecular chaperone (DnaJ superfamily), mitochondrial import inner membrane translocate subunit TIM14 | 35081 | GRMZM2G029385 | 2.217 | 525.5 | 110.8 | 4.74 |
| NADH-dehydrogenase (ubiquinone); FAD, NADP, NADPH binding | 36685 | GRMZM2G563190 | 2.143 | 433.5 | 104.5 | 4.15 |
| Monodehydroascorbate/ferredoxin reductase | 32175 | GRMZM2G134708 | 2.108 | 509.5 | 110.9 | 4.59 |
| Serine/threonine-protein kinase SAPK4 | 30206 | GRMZM2G063961 | 2.069 | 381.3 | 82.2 | 4.64 |
| Collagen; f-box; glutamine; pqe-1 | 28230 | GRMZM2G119523 | 2.054 | 301 | 67.9 | 4.43 |
| Secretory carrier membrane protein, SC3, transport | 5387 | GRMZM2G011078 | 2.053 | 324.1 | 76.6 | 4.23 |
| Prohibitin, Mitochondrial prohibitin complex protein 1, membrane, PHB3 | 8540 | GRMZM2G410710 | 2.028 | 718.6 | 171.1 | 4.20 |
| Emp24/gp25L/p24 family of membrane trafficking proteins, calcium binding, phospholipid binding | 26591 | GRMZM2G134502 | 2.016 | 459.7 | 111.9 | 4.11 |
| SWI1/DYAD involved in meiotic recombination | 28072 | GRMZM2G300786 | 2.044 | 461.7 | 103 | 4.48 |
| QBI25h06.xg QBI Zea mays cDNA clone QBI25h06, mRNA sequence | 7578 | TC297465 | 1.976 | 268.9 | 67.3 | 4.00 |
| Serine/threonine protein phosphatase, protein amino acid dephosphorylation | 35049 | GRMZM2G109496 | 1.729 | 210.7 | 60.7 | 3.47 |
| RecA like, recombination; Dmc1 protein type B, (ARLIM15, ATDMC1, DMC1): DNA repair (Rad51) family protein | 30014 | TC313913 | 1.691 | 238.5 | 57.2 | 4.17 |
| D-ribulose-5-phosphate3-epimerase (pentose phosphate pathway) | 27497 | TC310688 | 1.682 | 418.6 | 128 | 3.27 |
| Triosephosphate isomerase | 43441 | GRMZM2G146206 | 1.628 | 1310.4 | 412.7 | 3.18 |
| NADP dependent malic enzyme | 42148 | TC305158 | 1.622 | 198.2 | 63 | 3.15 |
| Homologue to UP: Q7Y1V3_ORYSA (Q7Y1V3) Eukaryotic translation initiation factor 1A, complete | 12101 | TC306331 | 1.619 | 558.9 | 159 | 3.52 |
| 60S ribosomal protein L41 | 28944 | TC286055 | 1.579 | 700.9 | 235 | 2.98 |
| Ste20-like serine/threonine protein kinase | 24104 | GRMZM2G135073 | 1.561 | 335.2 | 104.2 | 3.22 |
| Weakly similar to PRF: NP_198523.1: 15240103: NP_198523 expressed protein (Arabidopsis thaliana), complete | 23515 | GRMZM2G032047 | 1.529 | 227.3 | 66.1 | 3.44 |
| Transcription initiation factor IIF, large subunit (RAP74), transcription initiation from RNA polymerase II promoter | 7458 | CB278279 | 1.525 | 201.2 | 71.6 | 2.81 |
| Similar to UP: O91332_9GAMA (O91332) EBNA-1, partial (5%) | 19140 | GRMZM2G329710 | 1.47 | 657.1 | 217.1 | 3.03 |
| GTPase Rab1/YPT1, small G protein superfamily, and related GTP-binding proteins | 20664 | TC280797 | 1.463 | 211.2 | 71.6 | 2.95 |
| Predicted K+/H+-antiporter | 36959 | GRMZM2G136710 | 1.45 | 136.9 | 46.7 | 2.93 |
| UTP--glucose-1-phosphate uridylyltransferase | 43055 | GRMZM5G889299 | 1.424 | 391.5 | 145.4 | 2.69 |
| Voltage-gated K+ channel, subunit beta/KCNAB | 22676 | TC280985 | 1.418 | 1025 | 390.6 | 2.62 |
| Similar to PRF: NP_850280.1: 30687109: NP_850280 splicing factor RSZ33 (RSZ33) (Arabidopsis thaliana), partial (51%) | 22646 | CO441573 | 1.405 | 1468.8 | 524.2 | 2.80 |
| Gi\|212724002\|ref\|NP_001132875.11: hypothetical protein LOC100194368 [Zea mays] (IDPct: 99.47/Score: 379.8) | 8252 | GRMZM2G169931 | 1.342 | 488.1 | 171.6 | 2.84 |
| Similar to GB: AAT36215.1: 47606403: AY550923 DNA repair and transcription factor XPB1 (Arabidopsis thaliana), partial (70%) | 38195 | TC312637 | 1.276 | 1401.7 | 546.4 | 2.57 |
| Predicted transporter/transmembrane protein | 31457 | TC305399 | 1.139 | 216.8 | 96.1 | 2.26 |
| Alpha/beta; esterase/lipase/thioesterase; fold; hydrolase; | 27137 | GRMZM2G115504 | 1.131 | 185.8 | 85.6 | 2.17 |
| Mitochondrial processing peptidase, alpha subunit | 26753 | GRMZM2G005036 | 1.126 | 1994.3 | 947.8 | 2.10 |
| SCF ubiquitin ligase, SKP1-like protein 1B (SKP1a is involved in recombination, SKP1b is also meiotic, see Nan, et al. 2011) | 42998 | GRMZM2G032562 | 1.095 | 163.7 | 77.7 | 2.11 |

TABLE 9-continued

AR-enriched or -specific transcripts involved in meiosis.

| AR-characteristic transcripts involved in meiosis (Description) | Probe ID | Protein ID | Log-fold change | AR Avg Intensity | Somatic Avg Intensity | Ratio |
|---|---|---|---|---|---|---|
| Splicing factor 3b, subunit 4 | 857 | TC307873 | 1.093 | 338.7 | 156.8 | 2.16 |
| Similar to UP: Q8KAP1_CHLTE (Q8KAP1) Malonyl CoA-acyl carrier protein transacylase, partial (5%) | 2438 | TC301402 | 1.079 | 383 | 179 | 2.14 |
| NADP+-dependent malic enzyme | 7972 | GRMZM2G159724 | 1.051 | 138.4 | 64.7 | 2.14 |
| Absence of first division1 (AFD1), nuclear chromosome; Rad21-4 protein, partial (64%) | 21701 | GRMZM2G059037 | 1.045 | 160.5 | 80.1 | 2.00 |
| FOG: Predicted E3 ubiquitin ligase, RHC1A | 25750 | TC283691 | 1.035 | 753.9 | 374.5 | 2.01 |
| Apospory-associated protein: aldose 1-epimerase | 575 | GRMZM2G103287 | 1.022 | 3484.2 | 1634.4 | 2.13 |
| HSP90 co-chaperone p23 | 3779 | TC289458 | 1.019 | 757.7 | 369 | 2.05 |
| Prohibitin4 | 5645 | TC298303 | 1.015 | 3299.7 | 1596 | 2.07 |
| Glyceraldehyde 3-phosphate dehydrogenase (GAPC3) | 26457 | GRMZM2G071630 | 1.007 | 119.6 | 59.7 | 2.00 |
| Similar to UP: Q5N7N1_ORYSA (Q5N7N1) MATE efflux protein-like, partial (16%) | 29463 | TC295868 | 1 | 353.1 | 162.7 | 2.17 |
| Similar to UP: T2AG_ORYSA (Q94HL5) Transcription initiation factor IIA gamma chain (TFIIA-gamma), partial (98%) | 320 | GRMZM5G832378 | 0.987 | 108.2 | 55.2 | 1.96 |
| 5/6-kinase; inositol; phosphate; 134-trisphosphate; kinase; 134-triphosphate; amppnp; chain; | 30813 | GRMZM2G456626 | 0.982 | 4572.6 | 2263 | 2.02 |
| Plasma membrane localization, nuclear gene encoding mitochondrial protein | 6255 | GRMZM2G116427 | 0.975 | 497.9 | 255.7 | 1.95 |
| Wound; wound-responsive; proteinprotein; responsive; uvrb/uvrc; | 15045 | GRMZM2G006468 | 0.968 | 468.2 | 234.8 | 1.99 |
| DNA repair protein RAD51/RHP5b, single stranded DNA repair | 40178 | GRMZM2G058954 | 0.968 | 186.9 | 96.3 | 1.94 |
| Predicted 3'-5' exonuclease, Werner syndrome DNA helicase, nucleosidase | 14753 | GRMZM2G111436 | 0.959 | 104.6 | 53.5 | 1.96 |
| Weakly similar to UP: Q4NUK4_9DELT (Q4NUK4) LigA, partial (5%) | 25980 | TC297993 | 0.953 | 213.7 | 104.2 | 2.05 |
| Similar to UP: Q6AVF2_ORYSA (Q6AVF2) Expressed protein, partial (28%) | 2660 | GRMZM2G107495 | 0.949 | 183 | 84.6 | 2.16 |
| Similar to UP: Q8S9J9_ARATH (Q8S9J9) At1g14000: F7A19_9, partial (89%) | 21937 | GRMZM2G159034 | 0.94 | 139.5 | 68.8 | 2.03 |
| Poor homologous synapsis 1 (PHS1) protein (meiosis chromosome pairing) | 37135 | GRMZM2G100103 | 0.928 | 126.7 | 67.5 | 1.88 |
| GI|219362991|ref|NP_001136933.1|: hypothetical protein LOC100217097 [Zea mays] (IDPct: 55.56/Score: 107.1) | 24284 | GRMZM2G019596 | 0.917 | 753.4 | 397.5 | 1.90 |
| 1-acylglycerol-3-phosphate O-acyltransferase | 28601 | GRMZM2G116243 | 0.914 | 469.5 | 237.7 | 1.98 |
| Peptidyl-prolyl; cis-trans; ppic-type; glycoprotein; isomerase; hyp-rich; histidine; kinase; | 2497 | GRMZM2G047204 | 0.913 | 325.4 | 174.9 | 1.86 |
| Weakly similar to PRF: NP_175779.1: 15220931: NP_175779 expressed protein (Arabidopsis thaliana), partial (64%) | 31983 | GRMZM2G153899 | 0.902 | 756.8 | 358.2 | 2.11 |
| Homologue to UP: O24560_MAIZE (O24560) Ubiquitin carrier protein, complete | 5629 | GRMZM2G007300 | 0.901 | 2006.3 | 1006.8 | 1.99 |
| NADH-dehydrogenase (ubiquinone) | 42463 | GRMZM2G041418 | 0.858 | 90.6 | 48.9 | 1.85 |
| Similar to PIR: S38958: S38958 chorismate mutase precursor (Arabidopsis thaliana), partial (75%) | 20990 | GRMZM2G028369 | 0.855 | 361.6 | 187.6 | 1.93 |
| Similar to UP: Q4VWY7_ORYSA (Q4VWY7) Monoglyceride lipase isoform 2-like, partial (90%) | 3565 | GRMZM2G042477 | 0.836 | 120.2 | 54.4 | 2.21 |
| Calcium-binding; polymerase; EF hand family | 30217 | GRMZM2G000397 | 0.811 | 2202 | 1272.5 | 1.73 |
| Myo-inositol-1-phosphate synthase, inositol-3-phosphate synthase | 31461 | GRMZM2G177461 | 0.808 | 90.4 | 51.5 | 1.76 |
| Predicted membrane protein, contains two CBS domains | 1881 | GRMZM2G050684 | 0.801 | 855.5 | 491.2 | 1.74 |
| DNA repair protein related to RAD51/RHP55 | 5043 | GRMZM2G058954 | 0.8 | 2155.7 | 1230.8 | 1.75 |
| Similar to UP: Q40211_LOTJA (Q40211) RAB7A, complete | 22438 | TC306072 | 0.788 | 511 | 267.4 | 1.91 |
| DNA mismatch repair protein MSH2 (MUS1) | 31864 | GRMZM2G056075 | 0.78 | 2523.6 | 1413.3 | 1.79 |
| Homologue to UP: Q9SAU8_WHEAT (Q9SAU8) HSP70, complete | 31883 | TC279806 | 0.76 | 9417.9 | 6084.6 | 1.55 |
| N-methyltransferase | 24878 | BM259506 | 0.759 | 85.1 | 53.1 | 1.60 |
| Alanine aminotransferase | 31998 | TC310367 | 0.756 | 182.8 | 108.5 | 1.68 |
| RecA family protein, NTP binding, DNA repair, single stranded DNA binding | 21435 | GRMZM2G700757 | 0.752 | 1379.6 | 773.2 | 1.78 |
| Synaptonemal complex central region protein ZYP1-1, similar to UP: Q4TWG2_ARATH (Q4TWG2) partial (7%) | 17004 | TC283445 | 0.751 | 521.7 | 301.9 | 1.73 |
| Endonuclease III, 4Fe4S cluster, base excision repair | 12222 | GRMZM2G113223 | 0.751 | 376.4 | 224.2 | 1.63 |
| PIR: PQ0178: PQ0178 glyceraldehyde-3-phosphate dehydrogenase 2 - (Zea mays), partial (28%) | 38000 | TC286409 | 0.748 | 167.7 | 92.5 | 1.81 |
| ZmAGO121, (AtAGO6 homolog) putatively involved in RdDM) Zwille: pinhead-like protein (Fragment), partial (74%) | 21908 | GRMZM2G432075 | 0.745 | 449.4 | 240.9 | 1.87 |
| Rhomboid domain containing 1 | 30829 | GRMZM2G140994 | 0.734 | 114.7 | 62 | 1.85 |
| Homologue to UP: Q7F8W1_ORYSA (Q7F8W1) OJ000315_02.12 protein, partial (14%) | 36643 | TC295705 | 0.724 | 573.2 | 315.9 | 1.81 |
| Acyl-CoA synthetase | 24579 | GRMZM2G174574 | 0.722 | 236.4 | 141.3 | 1.67 |
| Similar to UP: Q40490_TOBAC (Q40490) Cyclin A-like protein, partial (10%) | 24894 | AW231811 | 0.719 | 68.3 | 46.1 | 1.48 |

TABLE 9-continued

AR-enriched or -specific transcripts involved in meiosis.

| AR-characteristic transcripts involved in meiosis (Description) | Probe ID | Protein ID | Log-fold change | AR Avg Intensity | Somatic Avg Intensity | Ratio |
|---|---|---|---|---|---|---|
| Weakly similar to UP: Q93W01_ARATH (Q93W01) At2g01080: F23H14.5, partial (75%) | 22034 | TC306070 | 0.715 | 136.5 | 83.2 | 1.64 |
| Apospory-associated protein: aldose 1-epimerase | 14667 | GRMZM2G103287 | 0.714 | 251.7 | 154.3 | 1.63 |
| Similar to UP: Q4LDR0_LYCES (Q4LDR0) Heat shock protein, partial (13%) | 7491 | GRMZM2G162968 | 0.71 | 491.6 | 310.2 | 1.58 |
| SNF2 domain-containing protein/helicase domain-containing protein (P31244) DNA repair protein RAD16, partial (9%) | 15367 | TC309700 | 0.701 | 100.6 | 58.9 | 1.71 |
| Similar to UP: Q8W0R0_SORBI (Q8W0R0) 3-glucanase, partial (16%) | 36870 | GRMZM2G310739 | 0.691 | 114.9 | 53.7 | 2.14 |
| Similar to UP: Q69UI4_ORYSA (Q69UI4) Kinesin 1-like, partial (7%) | 20913 | GRMZM5G878823 | 0.674 | 217.3 | 129.3 | 1.68 |
| Similar to UP: Q4RMN6_TETNG (Q4RMN6) Chromosome 10 SCAF15019, whole genome shotgun sequence. (Fragment) | 12769 | GRMZM2G034631 | 0.66 | 146 | 89 | 1.64 |
| Similar to UP: Q6MWV6_MYCTU (Q6MWV6) PE-PGRS FAMILY PROTEIN, partial (5%) | 132 | AI692111 | 0.653 | 375.1 | 236.6 | 1.59 |
| Weakly similar to UP: Q9FFG8_ARATH (Q9FFG8) Selenium-binding protein-like, partial (15%) | 3653 | GRMZM2G474929 | 0.645 | 105.8 | 66.1 | 1.60 |
| UDP-glucuronic acid decarboxylase, 3-beta-hydroxy-Delta(5)-steroid dehydrogenase//dTDP-4-dehydrorhamnose reductase | 36611 | GRMZM2G347717 | 0.628 | 163.4 | 105.4 | 1.55 |
| DSB repair, DNA helicase - NHEJ (non homologous end joining) double stranded break | 22116 | GRMZM2G137968 | 0.626 | 731.7 | 454.4 | 1.61 |
| Homologue to GB: BAD66930.1: 54650506: AB193582 GDP-mannose-3,5-epimerase (Oryza sativa (japonica)), partial (97%) | 26592 | GRMZM2G138907 | 0.616 | 109.5 | 68.2 | 1.61 |
| Similar to UP: Q9XYX5_9ASCI (Q9XYX5) Homeobox protein Otx, partial (5%) | 16279 | TC284770 | 0.603 | 100.3 | 58.3 | 1.72 |
| Histone; binding; htta-Aspergillus niger; Histone H2A | 37982 | GRMZM2G046055 | 0.602 | 12864.2 | 8447.5 | 1.52 |
| Similar to UP: Q6ED63_OLEEU (Q6ED63) Acyl-CoA: diacylglycerol acyltransferase 1, partial (21%) | 18807 | GRMZM2G169089 | 0.601 | 148.9 | 89.9 | 1.66 |
| Galactosyltransferase | 3083 | GRMZM2G153760 | 0.597 | 198.5 | 130.9 | 1.52 |
| Weakly similar to PRF: NP_194332.2: 42567155: NP_194332 expressed protein (Arabidopsis thaliana), partial (30%) | 27957 | GRMAM2G067350 | 0.589 | 136.7 | 91.8 | 1.49 |
| DNA repair; recA family protein (Arabidopsis thaliana), partial (57%) | 39122 | GRMZM2G700757 | 0.588 | 166.9 | 112.1 | 1.49 |
| Similar to UP: Q9SSZ6_ORYSA (Q9SSZ6) Cyclin, partial (18%) | 17125 | TC296255 | ON/OFF | 149 | 0 | N/A |
| Gi\|226498058\|ref\|NP_001145298.11: hypothetical protein LOC100278599 [Zea mays] (IDPct: 99.42/Score: 322) | 15154 | GRMZM2G162497 | ON/OFF | 114.4 | 0 | N/A |
| Similar to PRF: NP_201225.1: 15237641: NP_201225 arginine: serine-rich splicing factor SC35 (Arabidopsis thaliana), partial (45%) | 37432 | GRMZM2G077823 | ON/OFF | 91.5 | 0 | N/A |
| Weakly similar to UP: Q9V3V0_DROME (Q9V3V0) CG10203-PA (DX16 protein) (SR family splicing factor 9G8), partial (7%) | 29353 | TC284035 | ON/OFF | 90.1 | 0 | N/A |
| UP: Q4VJ26_MAIZE (Q4VJ26) Laccase 1, complete (oxygen binding - quinone associated) | 41886 | GRMZM5G842071 | ON/OFF | 79.5 | 0 | N/A |
| Similar to UP: Q6QA26_ORYSA (Q6QA26) Phosphoethanolamine N-methyltransferase, partial (15%) | 27442 | GRMZM2G169709 | ON/OFF | 76.5 | 0 | N/A |
| Weakly similar to PRF: NP_200047.2: 42568485: NP_200047 exocyst subunit EXO70 family protein (Arabidopsis thaliana) | 1688 | GRMZM2G464382 | ON/OFF | 73.2 | 0 | N/A |
| Similar to OMNI: GMSORF0554::: COG2252: Permeases (Mycobacterium smegmatis str. MC2 155), partial (4%) | 10936 | CD436448 | ON/OFF | 65 | 0 | N/A |
| AGO18b, 650 similar to UP: Q69VD5_ORYSA (Q69VD5) ZLL: PNH homologous protein, partial (8%) | 39042 | GRMZM2G457370 | ON/OFF | 58.3 | 0 | N/A |
| Similar to OMNI: NTL01CG2231: NP_601565.1: 19553563: ribonuclease E (Corynebacterium glutamicum ATCC 13032) | 1137 | DR830496 | ON/OFF | 54.3 | 0 | N/A |
| 40S ribosomal protein S7e | 22250 | GRMZM2G458974 | ON/OFF | 52.1 | 0 | N/A |
| UP: Q9VNS7_DROME (Q9VNS7) CG14454-PA (CG32433-PA) (RE01153p), partial (8%) | 27619 | GRMZM2G133006 | ON/OFF | 49.9 | 0 | N/A |
| Weakly similar to UP: Q8J0S5_EMENI (Q8J0S5) Meiotic recombination protein, partial (3%) | 42970 | GRMZM5G856297 | ON/OFF | 49.8 | 0 | N/A |

Materials and Methods

RNA extraction: RNA was extracted with TRIzol reagent (Ambion, Austin, Tex.) from anthers snap frozen on liquid nitrogen within 20 min of dissection, except in the case of laser microdissected cell types (described below). Extraction was followed by chloroform/isopropanol precipitation and resuspension in RNase-free H$_2$O. All RNA samples were DNase treated with RNase-free DNase Set (Qiagen, Venlo, The Netherlands, #79254), purified on a RNAeasy mini spin column (Qiagen, #74104), and quantified on a Nanodrop 1000 spectrophotometer (Thermo Scientific, Waltham, Mass.).

Laser microdissection: Anthers were fixed in 3:1 ethanol: acetic acid solution, then cryoprotected in 15% sucrose/PBS and embedded in optimal cutting temperature compound (Ted Pella Inc., Redding, Calif. 96069) and frozen, cryosectioned and attached to slides with a Cryojane (Electron Microscopy Sciences, Hatfield, Pa. 19440). After an ethanol to xylenes dehydration series, 10-12 µm sections were laser microdissected using the Zeiss P.A.L.M. Laser Microbeam ("www." followed by "palm-microlaser." followed by "com") for recovery of cell types. RNA was isolated using the PicoPure RNA extraction kit (Arcturus Molecular Devices).

qRT-PCR: mac1 was cloned and the gene encodes the closest maize homolog to TPD1, a putative secreted ligand. We designed primers to the gene for qRT-PCR. We synthesized cDNA using the SuperScript III First-Strand Synthesis System for RT-PCR (kit #18080, Invitrogen, Carlsbad, Calif. 92008) using oligo $(dT)_{20}$. Each reaction was performed in technical triplicate on cDNA derived from 8-10 ng starting mRNA with SYBRGreenER qPCR SuperMix (Invitrogen, #11762) on an Opticon 2 thermocycler (Bio-Rad, Richmond, Calif. 94547) and fluorescent values were analyzed using PCR miner to account for primer efficiencies. Mac1 transcript was detected using a forward primer in exon 1 (5'-AACCCTACTGCGAAACAACT-3'; SEQ ID NO:1), and a reverse primer that spans exon 2 and 3 (5'-CGAGAATCCTGCGTCCTGAT-3; SEQ ID NO:2) so as to avoid amplifying contaminating genomic DNA. Cyanase was used as a control gene (Forward: 5'-GGTGGTCACATTTGATGGG-3'; SEQ ID NO:3; Reverse: 5'-CTGAGCCCGATACCAACC-3'; SEQ ID NO:4). The ratio of Mac1 to Cyanase was used to normalize expression among biological samples. Each sample type was tested in biological triplicate.

Microarray analysis: For the msca1 and fertile comparison (200 µm anthers), two rounds of RNA amplification and the hybridization were performed as described previously (43). For the laser microdissected AR versus whole anther comparison, two different procedures were used: after RNA extraction, DNase treatment, and RNAeasy column purification, whole anther RNA was quantified and 50 ng of RNA was used for amplification. For AR cell RNA, after laser microdissecction, PicoPure extraction and DNase treatment (described above), RNA was resuspended in water and quantified and 50 ng was used for amplification. Both sample types were amplified according to the Agilent Two-Color Microarray-Based Gene Expression Analysis Low Input Quick Amp Labeling Protocol (version 6.5, May 2010) (Santa Clara, Calif.) and hybridized in 4×44K format (Part number: G2519F; Design ID: 016047). Two biological replicates were taken for each sample type for dye swap. Background fluorescence cut off was set and data was normalized. Genes were identified as being above background based on expression at least 3 standard deviations above the mean intensity of negative control probes (false discovery rate $p<0.001$).

Confocal imaging, and EdU and PI staining were performed as described previously (6). Oxygen probe was an Oxygraph Tx3 (NTH-Pst1-L5-NS40-0.8-YOP) obtained from Presens (Regensburg, Germany). All chemicals were obtained from Sigma Chemical Co. (St. Louis, Mo.) and dissolved in water at the indicated molarities and injected using a 26 gauge needle into the airspace surrounding the immature tassel.

W23 bz2 (deficient in vacuolar anthocyanin accumulation) inbred lines were greenhouse grown in Stanford, Calif. as described previously. Anther length is a reliable indicator of developmental stage1. AR and somatic cells were isolated by LCM and total RNA was extracted from each biological replicate as described previously. We used 0.30-0.35 mm anthers, measured at dissection from the central spike of 2.5 cm tassels. Total RNA was extracted from anther primordia (<0.15 mm), and all samples were amplified and hybridized in 4×44K format (Agilent Part number: G2519F; Design ID: 016047).

Slides were scanned and data were processed. Briefly, the resulting median foreground values for the red and green channels were normalized in two steps using the limma package in R: "within arrays" using the lowess method and "between arrays" using the quartile method. Probes with expression values greater than 3.0 standard deviations above the average foreground of the array's negative controls were considered "ON", resulting in an estimated false discovery rate of 0.13%. Probes with fewer than 75% of the replicate measurements scored as "ON" were then excluded from further analysis. Significance for differential expression was set at ~1.5-fold (log 2~0.58) with a p-value≤0.05. As confirmation, normalized intensities averaged across replicates were compared and presented in supplementary tables as ratios. Anther primordia expression was analyzed in comparisons between <0.15 mm and 0.25 mm and 0.4 mm mac1 mutant anthers.

qRT-PCR was performed as described previously. In situ hybridizations were performed with probe transcribed using the DIG RNA Labeling Kit (T7/SP6). Sense and antisense probes were synthesized from PCR fragments amplified from cDNA clones obtained from the Arizona maize cDNA collection ("http://" followed by "maizecdna." followed by "org/"). RNA in situ hybridizations were performed on 0.30-0.35 mm anthers residing on the central spike of ~2.5 cm tassels.

What is claimed is:

1. A method of altering the amount of pollen in a developing anther of a plant, comprising:
   (a) identifying a plant comprising an immature anther at a stage of development in which archesporial cells are being specified or are not yet specified;
   (b) locally exposing the immature anther of the plant of (a) to redox-modulatory conditions prior to or during specification of archesporial cells in the anther, thereby changing the redox potential of cells in said anther and altering the number of progenitor cells that differentiate into archesporial cells in said anther, and
   (c) growing the plant such that the immature anther develops into a mature anther that has at least epidermal cells, subepidermal cells, and either an increase in pollen or a decrease in pollen, relative to a control anther of the same stage as the immature anther of (a) that has not been exposed to the redox-modulatory conditions and
   (i) wherein a plant having increased pollen production and/or enlarged anther size is the result of locally exposing said anther to hypoxic conditions or to a reducing agent at a concentration that lowers the amount of reactive oxygen species in cells of said anther, as compared to a control plant not expose to said hypoxic conditions or reducing agent; or
   (ii) wherein a plant having reduced pollen production is the result of locally exposing said anther to an oxidizing agent at a concentration that increases the amount of reactive oxygen species in cells of said anther, as compared to a control plant not exposed to said oxidizing agent.

2. The method of claim 1, wherein the exposing step (b) comprises locally exposing the anther to hypoxic conditions or to a reducing agent at a concentration that lowers the amount of reactive oxygen species in said cells of the anther, thereby lowering the amount of reactive oxygen species in said cells and increasing the number of archesporial cells.

3. The method of claim 2, wherein increasing the number of archesporial cells in said anther results in a plant having larger anther size and/or higher pollen production, relative to a control plant that has not been exposed to hypoxic conditions or to said reducing agent.

4. The method of claim 2, wherein said exposing comprises placing said anther in an environment that contains less than 10% oxygen.

5. The method of claim 1, wherein the exposing step (b) comprises contacting said anther with an oxidizing agent at a concentration that increases the amount of reactive oxygen species in said cells, thereby increasing the amount of reactive oxygen species in said cells and decreasing the number of archesporial cells.

6. The method of claim 5, wherein decreasing the number of archesporial cells in said anther results in a plant having smaller anther size and/or lower pollen production than a control plant that has not been subjected to said applying.

7. The method of claim 5, wherein decreasing the number of archesporial cells results in a male sterile plant.

8. The method of claim 5, wherein said oxidizing agent is a peroxide.

9. The method of claim 1, wherein the exposing step (b) comprises exposing said developing anther to a gas.

10. The method of claim 1, wherein the exposing step (b) comprises spraying said developing anther with a liquid that comprises a redox-modulatory compound.

11. The method of claim 10, wherein said redox-modulatory compound is dissolved in said liquid.

12. The method of claim 10, wherein said redox-modulatory compound is in or on a particle that is present in said liquid.

13. The method of claim 1, wherein said exposing comprises placing a solid form of a redox-modulatory compound on said developing anther.

14. The method of claim 1, wherein said plant is a monocot.

15. The method of claim 1, wherein said plant is a dicot.

16. A method of making a male sterile plant comprising:
(a) identifying a plant comprising one or more immature anthers at a stage of development in which archesporial cells are being specified or are not yet specified;
(b) locally exposing the anthers of the plant of (a) to an oxidizing agent at a concentration that increases the amount of reactive oxygen species in cells in said anthers prior to or during specification of archesporial cells in the anthers, wherein the oxidizing agent increases the amount of reactive oxygen species in said cells and decreases the number of progenitor cells that differentiate into archesporial cells; and
(c) cultivating a male sterile plant, wherein the male sterile plant contains a mature anther that has at least epidermal cells, subepidermal cells, and no pollen, wherein male sterility of said plant results from the treatment of step (b).

17. The method of claim 16, further comprising crossing said male sterile plant with another plant to produce a hybrid plant.

18. The method of claim 17, wherein said hybrid plant has hybrid vigor relative to its parents.

19. The method of claim 18, wherein said plant is rice or corn.

\* \* \* \* \*